US012629445B2

(12) United States Patent
Addison et al.

(10) Patent No.: US 12,629,445 B2
(45) Date of Patent: May 19, 2026

(54) REACTIVE HYDROGEL FORMING FORMULATIONS AND RELATED METHODS, INCLUDING METHODS OF PREPARATION

(71) Applicant: Bard Peripheral Vascular, Inc., Tempe, AZ (US)

(72) Inventors: Jordan Addison, Chandler, AZ (US); Heather Storm, Phoenix, AZ (US); Ethan Blank, Tempe, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 813 days.

(21) Appl. No.: 17/942,536

(22) Filed: Sep. 12, 2022

(65) Prior Publication Data

US 2023/0094351 A1 Mar. 30, 2023

Related U.S. Application Data

(63) Continuation-in-part of application No. PCT/US2021/023359, filed on Mar. 19, 2021.

(60) Provisional application No. 63/247,039, filed on Sep. 22, 2021, provisional application No. 62/992,881, filed on Mar. 20, 2020.

(51) Int. Cl.
*A61M 5/19* (2006.01)
*A61L 24/00* (2006.01)
*A61L 24/04* (2006.01)

(52) U.S. Cl.
CPC ......... *A61L 24/0031* (2013.01); *A61L 24/043* (2013.01); *A61M 5/19* (2013.01)

(58) Field of Classification Search
None
See application file for complete search history.

(56) References Cited

U.S. PATENT DOCUMENTS

| | | | |
|---|---|---|---|
| 4,002,173 | A | 1/1977 | Manning et al. |
| 4,101,380 | A | 7/1978 | Rubinstein et al. |
| 4,537,767 | A | 8/1985 | Rothman et al. |

(Continued)

FOREIGN PATENT DOCUMENTS

| | | | |
|---|---|---|---|
| AU | 2007296056 | A1 | 3/2008 |
| CA | 2451624 | A1 | 12/2002 |

(Continued)

OTHER PUBLICATIONS

International Search Report and Written Opinion mailed Jul. 8, 2021 for International Application No. PCT/US2021/023359.

(Continued)

*Primary Examiner* — Peter A Salamon
(74) *Attorney, Agent, or Firm* — Wolf, Greenfield & Sacks, P.C.

(57) ABSTRACT

Compositions and methods related to hydrogel tissue sealants are generally described. In certain embodiments, a hydrogel forming composition is provided in dry form (e.g., as one or more powder mixtures) and comprises at least an electrophilic polymer crosslinking agent and a nucleophilic polymer such as a protein that is capable of crosslinking with the crosslinking agent. One or more solvents able to dissolve the crosslinking agent and the protein can be provided and used to dissolve the hydrogel forming composition to facilitate crosslinking.

9 Claims, 15 Drawing Sheets

(56) References Cited

U.S. PATENT DOCUMENTS 4,664,105 A 5/1987 Dautzenberg et al.
4,775,622 A 10/1988 Hitzeman et al.
4,839,345 A 6/1989 Doi et al.
4,909,251 A 3/1990 Seelich
4,913,897 A 4/1990 Chvapil et al.
4,914,027 A 4/1990 Knapp et al.
4,937,193 A 6/1990 Hinchliffe et al.
4,990,447 A 2/1991 Konig et al.
5,037,744 A 8/1991 Knapp et al.
5,100,784 A 3/1992 Latta et al.
5,118,794 A 6/1992 Grangeorge et al.
5,132,404 A 7/1992 Ohtani et al.
5,187,261 A 2/1993 Latta et al.
5,209,776 A 5/1993 Bass
5,250,662 A 10/1993 Chang
5,260,202 A 11/1993 Clarke et al.
5,277,818 A 1/1994 Matsuoka et al.
5,292,362 A 3/1994 Bass et al.
5,302,697 A 4/1994 Goodey et al.
5,324,775 A 6/1994 Rhee et al.
5,369,020 A 11/1994 Sumi et al.
5,380,712 A 1/1995 Ballance et al.
5,409,815 A 4/1995 Nakagawa et al.
5,410,016 A 4/1995 Hubbell et al.
5,440,018 A 8/1995 Ohmura et al.
5,476,909 A 12/1995 Kim et al.
5,502,042 A 3/1996 Gruskin et al.
5,503,993 A 4/1996 Hayasuke et al.
5,514,379 A 5/1996 Weissleder et al.
5,514,380 A 5/1996 Song et al.
5,521,287 A 5/1996 Ohmura et al.
5,571,801 A 11/1996 Segall et al.
5,583,114 A * 12/1996 Barrows ............... A61L 24/046 424/193.1
5,593,858 A 1/1997 Fleer et al.
5,605,255 A 2/1997 Reidel et al.
5,612,196 A 3/1997 Becquart et al.
5,612,197 A 3/1997 Ohda et al.
5,616,691 A 4/1997 Takahashi et al.
5,627,046 A 5/1997 Falcone et al.
5,627,052 A 5/1997 Schrader
5,631,145 A 5/1997 Kobayashi et al.
5,633,146 A 5/1997 Fleer et al.
5,643,792 A 7/1997 Okabayashi et al.
5,648,243 A 7/1997 Hurwitz et al.
5,656,729 A 8/1997 Fuluhata et al.
5,667,986 A 9/1997 Goodey et al.
5,677,424 A 10/1997 Rucheton et al.
5,679,543 A 10/1997 Lawlis
5,691,451 A 11/1997 Ohya et al.
5,728,553 A 3/1998 Goodey et al.
5,733,563 A 3/1998 Fortier
5,752,974 A 5/1998 Rhee
5,756,313 A 5/1998 Okabayashi et al.
5,759,819 A 6/1998 Kobayashi et al.
5,770,229 A 6/1998 Tanihara et al.
5,783,423 A 7/1998 Wood et al.
5,791,352 A 8/1998 Reich et al.
5,846,930 A 12/1998 Ristol Debart et al.
5,849,874 A 12/1998 van der Laken et al.
5,874,500 A 2/1999 Rhee et al.
RE36,259 E 7/1999 Tenold
5,919,907 A 7/1999 Shanbrom
5,962,649 A 10/1999 Noda et al.
5,965,386 A 10/1999 Kerry-Williams et al.
5,986,062 A 11/1999 Ohmura et al.
5,994,507 A 11/1999 Pilotti et al.
6,001,974 A 12/1999 Demmer et al.
6,022,954 A 2/2000 Dernis et al.
6,034,221 A 3/2000 Berezenko et al.
6,043,213 A 3/2000 Tsubota
6,051,248 A 4/2000 Sawhney et al.
6,060,461 A 5/2000 Drake
6,063,061 A 5/2000 Wallace
6,113,629 A 9/2000 Ken
6,150,504 A 11/2000 Van Der Laken et al.
6,165,201 A 12/2000 Sawhney et al.
6,166,130 A 12/2000 Rhee et al.
6,177,095 B1 1/2001 Sawhney et al.
6,179,862 B1 1/2001 Sawhney
6,183,498 B1 2/2001 Devore et al.
6,217,894 B1 4/2001 Sawhney et al.
6,312,725 B1 11/2001 Wallace et al.
6,328,229 B1 12/2001 Duronio et al.
6,362,254 B2 3/2002 Harris et al.
6,371,975 B2 4/2002 Cruise
6,437,025 B1 8/2002 Harris et al.
6,458,147 B1 10/2002 Cruise et al.
6,458,889 B1 10/2002 Trollsas et al.
6,475,508 B1 11/2002 Schwartz et al.
6,495,127 B1 12/2002 Wallace et al.
6,504,011 B1 1/2003 Van Der Laken et al.
6,514,534 B1 2/2003 Sawhney
6,521,431 B1 2/2003 Kiser et al.
6,534,591 B2 3/2003 Rhee et al.
6,541,543 B2 4/2003 Harris et al.
RE38,158 E 6/2003 Barrows et al.
6,576,263 B2 6/2003 Truong et al.
6,613,884 B1 9/2003 Johansson
6,617,133 B1 9/2003 Noda et al.
6,624,245 B2 9/2003 Wallace et al.
6,629,947 B1 10/2003 Sahatjian et al.
6,638,740 B1 10/2003 Goodey et al.
6,648,852 B2 11/2003 Wirt et al.
6,685,727 B2 2/2004 Fisher et al.
6,703,047 B2 3/2004 Sawhney et al.
6,706,690 B2 3/2004 Reich
6,708,847 B2 3/2004 Ljungquist
6,733,472 B1 5/2004 Epstein et al.
6,818,018 B1 11/2004 Sawhney
6,830,756 B2 12/2004 Hnojewyj
6,831,157 B2 12/2004 Van Der Laken et al.
6,833,408 B2 12/2004 Sehl et al.
6,874,657 B2 4/2005 Metzner et al.
6,887,974 B2 5/2005 Pathak
6,899,889 B1 5/2005 Hnojewyj et al.
6,908,749 B2 6/2005 Nouchi et al.
RE38,827 E * 10/2005 Barrows ................ C09J 189/00 424/193.1
6,969,400 B2 11/2005 Rhee et al.
6,989,192 B2 1/2006 Husemann et al.
6,994,686 B2 2/2006 Cruise et al.
7,001,885 B2 2/2006 Adachi et al.
7,008,635 B1 3/2006 Coury et al.
7,009,034 B2 3/2006 Pathak et al.
7,025,990 B2 4/2006 Sawhney
7,030,278 B2 4/2006 Harris et al.
7,057,019 B2 6/2006 Pathak
7,074,425 B2 7/2006 Constantine et al.
7,077,339 B2 7/2006 Leach
7,094,872 B2 * 8/2006 Tjoeng ...................... A61P 5/10 548/542
7,119,124 B2 10/2006 Hegedus et al.
7,151,135 B2 12/2006 Rhee et al.
7,166,577 B2 1/2007 Otagiri et al.
7,176,256 B2 2/2007 Rhee et al.
7,223,561 B2 5/2007 Goodey et al.
7,223,803 B2 5/2007 Harris et al.
7,238,364 B2 7/2007 Sawhney et al.
7,247,314 B2 7/2007 Hnojewyj et al.
7,279,001 B2 10/2007 Addis et al.
7,304,208 B2 12/2007 Huang et al.
7,307,148 B2 12/2007 Bousquet-Gagnon et al.
7,318,933 B2 1/2008 Hnojewyj
7,320,962 B2 1/2008 Reich
7,332,566 B2 2/2008 Pathak et al.
7,335,220 B2 2/2008 Khosravi et al.
7,347,850 B2 3/2008 Sawhney et al.
7,351,249 B2 4/2008 Hnojewyj et al.
7,423,124 B2 9/2008 Belew et al.
7,459,542 B2 12/2008 Sang et al.
7,485,719 B2 2/2009 Abe et al.
7,490,738 B2 2/2009 Crews
7,501,455 B2 3/2009 Hegedus et al.

(56) References Cited

U.S. PATENT DOCUMENTS 7,516,872 B2 4/2009 Boone et al.
7,528,202 B2 5/2009 Harris et al.
7,592,418 B2 9/2009 Pathak et al.
7,597,882 B2 10/2009 Pathak et al.
7,601,515 B2 10/2009 Goodey et al.
7,641,075 B2 1/2010 Crews
7,648,713 B2 1/2010 Sawhney
7,714,088 B2 5/2010 Harris et al.
7,718,851 B2 5/2010 Huang et al.
7,727,547 B2 6/2010 Fortune et al.
7,799,767 B2 9/2010 Lamberti et al.
7,883,693 B2 2/2011 Sehl et al.
7,914,819 B1 3/2011 Wen et al.
7,943,570 B2 5/2011 Nakajou et al.
7,963,937 B2 6/2011 Pauser et al.
7,972,357 B2 7/2011 Bettuchi
7,993,877 B2 8/2011 Van Urk et al.
8,003,742 B2 8/2011 Harris et al.
8,034,367 B2 10/2011 Hnojewyj
8,067,031 B2 11/2011 Daniloff et al.
8,084,580 B2 12/2011 Jorquera Nieto et al.
8,088,416 B2 1/2012 Jorquera Nieto et al.
8,092,837 B2 1/2012 Enyart et al.
8,100,294 B2 1/2012 May et al.
8,105,622 B2 1/2012 Sawhney
8,119,604 B2 2/2012 Gombotz et al.
RE43,331 E 5/2012 Samaritani et al.
8,231,599 B2 7/2012 Jorquera Nieto et al.
8,236,527 B2 8/2012 Chen et al.
8,236,927 B2 8/2012 Stange
8,241,656 B2 8/2012 Chudzik et al.
8,252,551 B2 8/2012 Sleep et al.
8,257,690 B2 9/2012 Chenault
8,258,102 B2 9/2012 Sleep
8,258,264 B2 9/2012 Tagawa et al.
8,288,477 B2 10/2012 Hadba et al.
8,309,680 B2 11/2012 McManus et al.
8,314,195 B2 11/2012 Elisseeff
8,323,262 B2 12/2012 D'Alessio et al.
8,409,249 B2 4/2013 Hnojewyj et al.
8,410,189 B2 4/2013 Carnahan et al.
8,460,695 B2 6/2013 Greenawalt
8,460,708 B2 6/2013 Daniloff et al.
8,481,073 B2 7/2013 Daniloff et al.
8,512,749 B2 8/2013 Sawhney et al.
8,535,705 B2 9/2013 Pathak et al.
8,545,864 B2 10/2013 Morris et al.
8,545,871 B2 10/2013 Arthur et al.
8,563,037 B2 10/2013 Rappleye et al.
8,623,842 B2 1/2014 Roberts et al.
8,673,335 B2 3/2014 Jones et al.
8,703,170 B2 4/2014 Hedrich et al.
8,703,176 B2 4/2014 Zhu et al.
8,741,832 B2 6/2014 Acharya et al.
8,802,652 B2 8/2014 Myntti et al.
8,846,022 B2 9/2014 Carnahan et al.
8,912,168 B2 12/2014 Ji et al.
8,968,716 B2 3/2015 Park et al.
8,968,783 B2 3/2015 Bennett et al.
8,980,295 B2 3/2015 Kao et al.
9,023,379 B2 5/2015 Pathak et al.
9,040,093 B2 5/2015 Wagner
9,061,087 B2 6/2015 Roberts et al.
9,114,172 B2 8/2015 Rhee et al.
9,345,662 B2 5/2016 Sinko et al.
9,345,809 B2 5/2016 Falcone et al.
9,375,505 B2 6/2016 Hedrich et al.
9,393,344 B2 7/2016 Stockman et al.
9,492,376 B2 11/2016 Seliktar et al.
9,616,088 B2 4/2017 Diehn et al.
9,662,400 B2 5/2017 Smith et al.
9,700,650 B2 7/2017 Gong et al.
9,707,252 B2 7/2017 Hadba et al.
9,708,416 B2 7/2017 Malmsjo et al.
9,844,597 B2 12/2017 Chau et al.
9,878,066 B2 1/2018 Stockman et al.
9,895,465 B2 2/2018 Lamberti et al.
9,993,577 B2 6/2018 Grinstaff et al.
10,172,938 B2 1/2019 Kiick et al.
10,314,937 B2 6/2019 Ji et al.
10,517,988 B1 12/2019 Modak et al.
10,584,184 B2 3/2020 Tramontano et al.
10,595,978 B2 3/2020 Lavigne et al.
10,905,792 B2 2/2021 Laub et al.
11,154,665 B2 10/2021 Goodman et al.
11,208,530 B2 12/2021 Zhao et al.
11,326,022 B2 5/2022 Delaney, Jr. et al.
11,739,166 B2 8/2023 Greenawalt et al.
12,151,045 B2 11/2024 Greenawalt et al.
12,161,777 B2 12/2024 Greenawalt et al.
2002/0009492 A1 1/2002 Truong et al.
2002/0022588 A1* 2/2002 Wilkie .................... A61L 24/10
424/94.64
2002/0106409 A1 8/2002 Sawhney et al.
2003/0008011 A1 1/2003 Mershon
2003/0023209 A1 1/2003 Gruskin et al.
2003/0187387 A1 10/2003 Wirt et al.
2003/0223957 A1 12/2003 Schwartz et al.
2005/0118238 A1 6/2005 Zhu et al.
2005/0123588 A1 6/2005 Zhu et al.
2005/0271727 A1 12/2005 Yao
2006/0078536 A1 4/2006 Kodokian et al.
2006/0088570 A1 4/2006 Cruise et al.
2006/0093648 A1 5/2006 Coury et al.
2006/0222622 A1* 10/2006 Faure ........................ A61K 8/64
514/13.2
2006/0228416 A1* 10/2006 Faure ................. A61K 38/1709
514/2.3
2006/0273109 A1 12/2006 Keller
2007/0065481 A1 3/2007 Chudzik et al.
2007/0086958 A1 4/2007 Drake et al.
2007/0213768 A1 9/2007 Wasserman et al.
2007/0248653 A1 10/2007 Cochrum et al.
2008/0038313 A1 2/2008 Addis et al.
2008/0187591 A1 8/2008 Rhee et al.
2008/0215088 A1 9/2008 Hnojewyj et al.
2008/0293910 A1 11/2008 Kapiamba et al.
2009/0018575 A1 1/2009 Fortune et al.
2009/0062233 A1 3/2009 Ji et al.
2009/0152267 A1 6/2009 May et al.
2009/0285780 A1 11/2009 Lee
2009/0291911 A1 11/2009 Myntti et al.
2010/0086678 A1 4/2010 Arthur et al.
2010/0087851 A1 4/2010 Jones et al.
2010/0100099 A1 4/2010 Reilly et al.
2010/0168007 A1 7/2010 Cruise et al.
2010/0173843 A1 7/2010 Hnojewyj
2010/0204718 A1 8/2010 Rappleye et al.
2010/0217231 A1 8/2010 Ilan et al.
2010/0274279 A1 10/2010 Delmotte
2010/0297235 A1 11/2010 Hnojewyj
2011/0027216 A1 2/2011 Chenault
2011/0104280 A1 5/2011 Hnojewyj
2011/0123476 A1 5/2011 Kapiamba et al.
2011/0125089 A1 5/2011 Senderoff et al.
2011/0150821 A1 6/2011 Daniloff et al.
2011/0166596 A1 7/2011 Delmotte
2011/0272436 A1 11/2011 Vogt et al.
2011/0274725 A1 11/2011 Breton et al.
2011/0282464 A1 11/2011 Sargeant et al.
2012/0035129 A1 2/2012 Wagman
2012/0041481 A1 2/2012 Daniloff et al.
2012/0101519 A1 4/2012 Hill et al.
2012/0156259 A1 6/2012 Rau et al.
2012/0244198 A1 9/2012 Malmsjo et al.
2012/0288530 A1 11/2012 Bordoloi et al.
2012/0315305 A1 12/2012 Koopman et al.
2013/0090291 A1 4/2013 Gulle et al.
2013/0096063 A1 4/2013 Hedrich et al.
2013/0096082 A1 4/2013 Harkamp et al.
2013/0209659 A1 8/2013 Racenet et al.
2013/0261192 A1 10/2013 Yang et al.
2013/0316974 A1 11/2013 Wang et al.
2014/0105950 A1 4/2014 Hardy et al.

(56) References Cited

U.S. PATENT DOCUMENTS

| | | | |
|---|---|---|---|
| 2014/0171883 A1 | 6/2014 | Roberts et al. | |
| 2015/0290363 A1* | 10/2015 | Pacetti | A61L 31/16 427/2.25 |
| 2015/0306277 A1 | 10/2015 | Pathak et al. | |
| 2016/0136235 A1 | 5/2016 | Hedrich et al. | |
| 2017/0056550 A1 | 3/2017 | Hoemann et al. | |
| 2017/0106119 A1 | 4/2017 | Skinner et al. | |
| 2017/0252479 A1 | 9/2017 | Ji et al. | |
| 2018/0036338 A1 | 2/2018 | Sanders et al. | |
| 2018/0344898 A1 | 12/2018 | Kronenthal et al. | |
| 2019/0001018 A1 | 1/2019 | Stockman et al. | |
| 2019/0247474 A1 | 8/2019 | Chen et al. | |
| 2019/0247537 A1* | 8/2019 | Taguchi | A61L 31/04 |
| 2019/0269819 A1 | 9/2019 | Dhanaraj et al. | |
| 2019/0388516 A1 | 12/2019 | Floyd et al. | |
| 2019/0388577 A1 | 12/2019 | Chandrashekhar-Bhat et al. | |
| 2019/0388580 A1 | 12/2019 | Guo et al. | |
| 2019/0388665 A1 | 12/2019 | Christakis et al. | |
| 2020/0030481 A1 | 1/2020 | Hedrich et al. | |
| 2020/0046877 A1 | 2/2020 | Kageyama et al. | |
| 2020/0102446 A1 | 4/2020 | Dowling | |
| 2020/0121825 A1 | 4/2020 | Dowling | |
| 2020/0139021 A1 | 5/2020 | Ilan et al. | |
| 2021/0060204 A1 | 3/2021 | Ji et al. | |
| 2022/0001075 A1 | 1/2022 | Greenawalt et al. | |
| 2022/0002444 A1 | 1/2022 | Greenawalt et al. | |
| 2022/0211900 A1 | 7/2022 | Greenawalt et al. | |
| 2022/0323637 A1 | 10/2022 | Greenawalt et al. | |
| 2024/0002549 A1 | 1/2024 | Greenawalt et al. | |
| 2025/0032663 A1 | 1/2025 | Greenawalt et al. | |

FOREIGN PATENT DOCUMENTS

| | | | |
|---|---|---|---|
| CA | 2581093 | A1 | 3/2006 |
| CN | 1400893 | A | 3/2003 |
| CN | 100556467 | C | 11/2009 |
| CN | 101594890 | A | 12/2009 |
| CN | 101791436 | A | 8/2010 |
| CN | 101497670 | B | 4/2012 |
| CN | 103957949 | A | 7/2014 |
| CN | 105838299 | A | 8/2016 |
| CN | 107708675 | A | 2/2018 |
| CN | 110464869 | A | 11/2019 |
| CN | 111068101 | A | 4/2020 |
| CN | 111317857 | A | 6/2020 |
| CN | 111317858 | A | 6/2020 |
| CN | 111714683 | A | 9/2020 |
| CN | 111714684 | A | 9/2020 |
| CN | 111714686 | A | 9/2020 |
| CN | 111714688 | A | 9/2020 |
| CN | 111729125 | A | 10/2020 |
| CN | 112138205 | A | 12/2020 |
| CN | 112494712 | A | 3/2021 |
| CN | 108744019 | B | 5/2021 |
| CN | 113061255 | A | 7/2021 |
| CN | 110269954 | B | 8/2021 |
| DE | 3502998 | A1 | 7/1986 |
| EP | 258067 | B1 | 3/1993 |
| EP | 420007 | B1 | 1/1994 |
| EP | 402205 | B1 | 12/1995 |
| EP | 701822 | A2 | 3/1996 |
| EP | 705298 | A1 | 4/1996 |
| EP | 422769 | B1 | 4/1997 |
| EP | 504823 | B1 | 6/1997 |
| EP | 367220 | B1 | 1/1998 |
| EP | 428758 | B1 | 1/1998 |
| EP | 584166 | B1 | 3/1998 |
| EP | 597035 | B1 | 9/1998 |
| EP | 876165 | A1 | 11/1998 |
| EP | 498133 | B1 | 5/1999 |
| EP | 625202 | B1 | 7/1999 |
| EP | 524681 | B1 | 11/1999 |
| EP | 559895 | B1 | 1/2001 |
| EP | 764209 | B1 | 1/2001 |
| EP | 828759 | B1 | 1/2001 |
| EP | 570916 | B1 | 1/2002 |
| EP | 1185288 | A1 | 3/2002 |
| EP | 655503 | B1 | 7/2002 |
| EP | 1218437 | A1 | 7/2002 |
| EP | 736605 | B1 | 4/2003 |
| EP | 341103 | B2 | 8/2003 |
| EP | 637317 | B1 | 8/2003 |
| EP | 699687 | B1 | 1/2004 |
| EP | 749478 | B1 | 2/2004 |
| EP | 1031578 | B1 | 4/2004 |
| EP | 1610829 | A1 | 1/2006 |
| EP | 1504031 | B1 | 8/2006 |
| EP | 1329462 | B1 | 12/2006 |
| EP | 1718673 | B1 | 9/2007 |
| EP | 1149163 | B1 | 12/2008 |
| EP | 1710250 | B1 | 4/2009 |
| EP | 2093245 | A2 | 8/2009 |
| EP | 1479393 | B1 | 8/2010 |
| JP | H10-503102 | A | 3/1998 |
| JP | 5232347 | B2 | 7/2013 |
| JP | 2014-533988 | A | 12/2014 |
| KR | 101507589 | B1 | 4/2015 |
| KR | 102220832 | B1 | 2/2021 |
| WO | WO 90/13540 | A1 | 11/1990 |
| WO | WO 93/15204 | A1 | 8/1993 |
| WO | WO 94/03155 | A1 | 2/1994 |
| WO | WO 97/22371 | A1 | 6/1997 |
| WO | WO 97/29715 | A1 | 8/1997 |
| WO | WO 98/29099 | A2 | 7/1998 |
| WO | WO 01/45761 | A1 | 6/2001 |
| WO | WO 2005/051232 | A | 6/2005 |
| WO | WO 2006/113845 | A1 | 10/2006 |
| WO | WO 2007/082061 | A1 | 7/2007 |
| WO | WO 2007/084609 | A2 | 7/2007 |
| WO | WO 2008/016983 | A2 | 2/2008 |
| WO | WO 2012/123728 | A2 | 9/2012 |
| WO | WO 2019/137414 | A1 | 7/2019 |
| WO | WO 2020/004813 | A1 | 1/2020 |
| WO | WO 2020/019880 | A1 | 1/2020 |
| WO | WO 2020/044237 | A1 | 3/2020 |
| WO | WO 2020/068814 | A1 | 4/2020 |
| WO | WO 2020/197969 | A1 | 10/2020 |
| WO | WO 2020/264188 | A1 | 12/2020 |
| WO | WO 2021/009015 | A1 | 1/2021 |
| WO | WO 2021/027219 | A1 | 2/2021 |
| WO | WO 2021/128050 | A1 | 7/2021 |
| WO | WO 2021/188904 | A1 | 9/2021 |
| WO | WO 2021/189024 | A1 | 9/2021 |

OTHER PUBLICATIONS

International Preliminary Report on Patentability mailed Sep. 29, 2022 for International Application No. PCT/US2021/023359.

International Search Report and Written Opinion mailed Oct. 29, 2020 for International Application No. PCT/US2020/039660.

International Preliminary Report on Patentability mailed Jan. 6, 2022 for International Application No. PCT/US2020/039660.

International Search Report and Written Opinion mailed Apr. 4, 2022 for International Application No. PCT/US2021/065204.

[No Author Listed], Tridynetm Vascular Sealant. C.R. Bard, Inc. 2015. 21 pages.

Abuchowski et al., Cancer therapy with chemically modified enzymes. I. Antitumor properties of polyethylene glycol-asparaginase conjugates. Cancer Biochem Biophys. Jun. 1984;7(2):175-86.

Anraku et al., Stabilizing mechanisms in commercial albumin preparations: octanoate and N-acetyl-L-tryptophanate protect human serum albumin against heat and oxidative stress. Biochim Biophys Acta. Oct. 1, 2004;1702(1):9-17. doi: 10.1016/j.bbapap.2004.07.002.

Cai et al., The Proof Is in the Pidan: Generalizing Proteins as Patchy Particles. ACS Cent Sci. Jul. 25, 2018;4(7):840-853. doi: 10.1021/acscentsci.8b00187. Epub Jun. 28, 2018.

Calabretta et al., Antibacterial activities of poly(amidoamine) dendrimers terminated with amino and poly(ethylene glycol) groups. Biomacromolecules. Jun. 2007;8(6):1807-11. doi: 10.1021/bm0701088. Epub May 19, 2007.

(56) References Cited

OTHER PUBLICATIONS

Carlstedt et al., Hydration and the phase diagram of acid hydrolyzed potato starch. Carbohydr Polym. Nov. 4, 2014;112:569-77. doi: 10.1016/j.carbpol.2014.06.037. Epub Jun. 21, 2014. Supplementary Material, 6 pages.
Cleland et al., Polyethylene glycol enhanced protein refolding. Biotechnology (NY). Sep. 1992;10(9):1013-9. doi: 10.1038/nbt0992-1013.
Conti et al., A proposed new method for the crosslinking of chitosan microspheres. Drug Deliv. 1998;5(2):87-93. doi: 10.3109/10717549809031383.
Diaz et al., Partially PEGylated PAMAM dendrimers as solubility enhancers of Silybin. Pharm Dev Technol. Sep. 2018;23(7):689-696. doi: 10.1080/10837450.2017.1315134. Epub Apr. 19, 2017.
El-Sayed et al., New approach for immobilization of 3-aminopropyltrimethoxysilane and TiO2 nanoparticles into cellulose for BJ1 skin cells proliferation. Carbohydr Polym. Nov. 1, 2018;199:193-204. doi: 10.1016/j.carbpol.2018.07.004. Epub Jul. 9, 2018.
Elchinger et al., Polysaccharides: The "Click" Chemistry Impact. Polymers. Sep. 27, 2011;3(4):1607-51. doi: 10.3390/polym3041607.
Ereth et al., Microporous polysaccharide hemospheres do not inhibit bone healing compared to bone wax or microfibrillar collagen. Orthopedics. Mar. 2008;31(3):222. doi: 10.3928/01477447-20080301-10.
Fogh-Andersen et al., Ionic binding, net charge, and Donnan effect of human serum albumin as a function of pH. Clin Chem. Jan. 1993;39(1):48-52.
Fuller, C., Reduction of intraoperative air leaks with Progel in pulmonary resection: a comprehensive review. J Cardiothorac Surg. Apr. 16, 2013;8:90. doi: 10.1186/1749-8090-8-90.
Hamdi et al., Enzymatic degradation of epichlorohydrin crosslinked starch microspheres by alpha-amylase. Pharm Res. Jun. 1999;16(6):867-75. doi: 10.1023/a:1018878120100.
Hamdi et al., Formulation of epichlorohydrin cross-linked starch microspheres. J Microencapsul. May-Jun. 2001;18(3):373-83. doi: 10.1080/02652040010019505.
Haroon et al., Chemical modification of starch and its application as an adsorbent material. R. Soc. Chem., Aug. 12, 2016;6:78264-85. doi: https://doi.org/10.1039/C6RA16795K.
Hasegawa et al., 'Click chemistry' on polysaccharides: a convenient, general, and monitorable approach to develop (1 -->3)-beta-D-glucans with various functional appendages. Carbohydr Res. Jan. 16, 2006;341(1):35-40. doi: 10.1016/j.carres.2005.10.009. Epub Nov. 14, 2005.
Holmes et al., Antimicrobial efficacy and mechanism of action of poly(amidoamine) (PAMAM) dendrimers against opportunistic pathogens. Int J Antimicrob Agents. Apr. 2019;53(4):500-507. doi: 10.1016/j.ijantimicag.2018.12.012. Epub Dec. 30, 2018.
Jevprasesphant et al., The influence of surface modification on the cytotoxicity of PAMAM dendrimers. Int J Pharm. Feb. 18, 20038252(1-2):263-6. doi: 10.1016/s0378-5173(02)00623-3.
Kobayashi et al., In vivo evaluation of a new sealant material on a rat lung air leak model. J Biomed Mater Res. 2001;58(6):658-65. doi: 10.1002/jbm.1066.
Koga et al., Chemically-modified cellulose paper as a microstructured catalytic reactor. Molecules. Jan. 15, 2015;20(1):1495-508. doi: 10.3390/molecules20011495.
Koga et al., In situ modification of cellulose paper with amino groups for catalytic applications. J. Mater. Chem. May 27, 2011;21:9356-61. doi: https://doi.org/10.1039/C1JM10543D.
Kuniak et al., Study of the Crosslinking Reaction between Epichlorohydrin and Starch. Starch. 1972;24(4):110-116. doi: 10.1002/star.19720240404.
Lopez et al., Antibacterial activity and cytotoxicity of PEGylated poly(amidoamine) dendrimers. Mol Biosyst. Oct. 2009;5(10):1148-56. doi: 10.1039/b904746h. Epub Jul. 3, 2009. Author Manuscript, 17 pages.
Qi et al., PEG-conjugated PAMAM dendrimers mediate efficient intramuscular gene expression. AAPS J. Sep. 2009;11(3):395-405. doi: 10.1208/s12248-009-9116-1. Epub May 29, 2009.
Rostami et al., Peptide-conjugated PEGylated PAMAM as a highly affinitive nanocarrier towards HER2-overexpressing cancer cells. RSC Adv. Oct. 21, 2016;6:107337-107343. doi: 10.1039/C6RA19552K.
Sadeghi et al., Evaluation of different parameters effect on maltodextrin production by alpha-amylase Termamyl 2-x, 2008, World Applied Sciences Journal, 3(1):34-39.
Schmitz et al., Use of a plant-based polysaccharide hemostat for the treatment of sternal bleeding after median sternotomy. J Cardiothorac Surg. Apr. 24, 2015;10:59. doi: 10.1186/s13019-015-0263-4.
Shao et al., Comparison of generation 3 polyamidoamine dendrimer and generation 4 polypropylenimine dendrimer on drug loading, complex structure, release behavior, and cytotoxicity. Int J Nanomedicine. 2011;6:3361-72. doi: 10.2147/IJN.S27028. Epub Dec. 16, 2011.
Suwanprateeb et al., Preparation and characterization of PEG-PPG-PEG copolymer/pregelatinized starch blends for use as resorbable bone hemostatic wax. J Mater Sci Mater Med. Dec. 2013;24(12):2881-8. doi: 10.1007/s10856-013-5027-x. Epub Aug. 17, 2013.
Tankam et al., Alkynyl polysaccharides: synthesis of propargyl potato starch followed by subsequent derivatizations. Carbohydr Res. Oct. 15, 2007;342(14):2049-60. doi: 10.1016/j.carres.2007.05.017. Epub May 18, 2007.
Wang et al., Preparation of amino-functionalized regenerated cellulose membranes with high catalytic activity. Int J Biol Macromol. Sep. 2017;102:944-951. doi: 10.1016/j.ijbiomac.2017.04.096. Epub Apr. 27, 2017.
Xue et al., Amino-terminated generation 2 poly(amidoamine) dendrimer as a potential broad-spectrum, nonresistance-inducing antibacterial agent. AAPS J. Jan. 2013;15(1):132-42. doi: 10.1208/s12248-012-9416-8. Epub Nov. 8, 2012.
Das et al., Modified biopolymer-dextrin based crosslinked hydrogels: application in controlled drug delivery. RSC Adv. Feb. 9, 2015;5:25014-50. doi: 10.1039/C4RA16103C.
Delval et al., Preparation, Characterization and Sorption Properties of Crosslinked Starch-Based Exchangers. J Carb Polym. Apr. 2005;60(1):67-75. doi: 10.1016/j.carbpol.2004.11.025.
Li et al., A biodegradable starch hydrogel synthesized via thiol-ene click chemistry. Polym Degrad Stab. Mar. 2017;137:75-82. doi: 10.1016/j.polymdegradstab.2016.07.015.
Lim et al., Chlorin e6-embedded starch nanogels for improved photodynamic tumor ablation. Polym Adv Technol. Nov. 2018;29(11):2766-73. doi: 10.1002/pat.4399.
Overby et al., Influence of Poly(Ethylene Glycol) End Groups on Poly(Ethylene Glycol)-Albumin System Properties as a Potential Degreadable Tissue Scaffold. J. Functional Biomat. Dec. 24, 2018;10(1):1-12.
U.S. Appl. No. 18/346,167, filed Jun. 30, 2023, Greenawalt et al.
U.S. Appl. No. 18/917,985, filed Oct. 16, 2024, Greenawalt et al.
Behrens et al., Hemostatic strategies for traumatic and surgical bleeding. J Biomed Mater Res A. Nov. 2014;102(11):4182-94. doi: 10.1002/jbm.a.35052. Epub Dec. 12, 2013.
Singh et al., Hemostatic Comparison of a Polysaccharide Powder and a Gelatin Powder. J Invest Surg. Aug. 2019;32(5):393-401. doi: 10.1080/08941939.2017.1423421. Epub Feb. 8, 2018.
[No Author Listed] ABC of Prehospital Emergency Medicine, edited by Tim Nutbeam (UK), translated by Wang et al., 2016, p. 39.

* cited by examiner

REACTIVE HYDROGEL FORMING FORMULATIONS AND RELATED METHODS, INCLUDING METHODS OF PREPARATION

RELATED APPLICATIONS

This application claims priority under 35 U.S.C. § 119(e) to U.S. Provisional Patent Application No. 63/247,039, filed Sep. 22, 2021, and entitled "Reactive Hydrogel Forming Formulations and Related Methods. Including Methods of Preparation." This application is also a continuation-in-part of International Patent Application No. PCT/US2021/023359, filed Mar. 19, 2021, and entitled "Reactive Hydrogel Forming Formulations and Related Methods," which claims priority under 35 U.S.C. § 119(e) to U.S. Provisional Patent Application No. 62/992,881, filed Mar. 20, 2020, and entitled "Reactive Hydrogel Forming Formulations and Related Methods." Each of the above-indicated applications is incorporated herein by reference in its entirety for all purposes.

TECHNICAL FIELD

Compositions and methods related to hydrogel tissue sealants are generally described.

BACKGROUND

Pneumothorax is a problematic complication of a lung biopsy procedure in which air passes into the pleural space as a result of a puncture of the parietal and visceral pleura. Pneumothorax poses significant concerns for clinicians performing and patients undergoing percutaneous lung biopsies. The incidence of pneumothorax in patients undergoing percutaneous lung biopsy has been reported to be anywhere between about 9% and about 54% of patients, with an average of about 15%. In addition, on average, about 7% of all percutaneous lung biopsies result in pneumothorax requiring a chest tube to be placed into the patient, which subsequently results in an average hospital stay of about 3 days. Factors increasing the risk of pneumothorax include increased patient age, obstructive lung disease, increased depth of lesion, multiple pleural passes, increased time of needle across the pleura, and traversal of a fissure. Pneumothorax can occur during or immediately after the lung biopsy procedure. Furthermore, other complications of percutaneous lung biopsy include hemoptysis, hemothorax, infection, and air embolism. The development of a novel hydrogel tissue sealant with the ability to adhere to and/or seal tissues (e.g. the pleura) to address pneumothorax and other surgical applications, and related methods, would be beneficial.

SUMMARY

Compositions and methods for forming hydrogel tissue sealants are generally described. The subject matter of the present invention involves, in some cases, interrelated products, alternative solutions to a particular problem, and/or a plurality of different uses of one or more systems and/or articles.

In some embodiments, a hydrogel forming composition for forming a hydrogel tissue sealant is described. In certain embodiments, the hydrogel forming composition comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the hydrogel forming composition comprises a second component comprising a protein that is capable of crosslinking with the crosslinking agent. In some embodiments, the hydrogel forming composition comprises one or more solvents able to dissolve the first component and the second component, and a surfactant. In certain embodiments, when the first component, the second component, and the surfactant are all dissolved in the one or more solvents, crosslinking of the crosslinking agent and the protein occurs to form the hydrogel tissue sealant.

In some embodiments, a hydrogel forming composition for forming a hydrogel tissue sealant comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the hydrogel forming composition comprises a protein that is capable of crosslinking with the crosslinking agent, one or more solvents able to dissolve the first component and the second component, and a surfactant, wherein when the crosslinking agent, the protein, and the surfactant are all dissolved in the one or more solvents, crosslinking of the crosslinking agent and the protein occurs to form the hydrogel tissue sealant.

According to certain embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In some embodiments, the hydrogel forming composition comprises a second component comprising a protein that is capable of crosslinking with the crosslinking agent and one or more solvents able to dissolve the first component and the second component, wherein when the first component and the second component are dissolved in the one or more solvents, upon mixing of the first component and the second component dissolved in the one or more solvents, crosslinking of the crosslinking agent and the protein occurs with a gel time less than or equal to 20 seconds to form the hydrogel tissue sealant.

According to some embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the hydrogel forming composition comprises a second component comprising a protein that is capable of crosslinking with the crosslinking agent, a first solvent able to dissolve the first component, and a second solvent able to dissolve the second component, wherein when the second component is dissolved in the second solvent the pH of the solution of the second component in the second solvent is greater than or equal to 10.2 and less than or equal to 10.6, and wherein when the first component is dissolved in the first solvent and combined with the solution of the second component in the second solvent a crosslinking solution of the first component and the second component is formed.

In certain embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. According to certain embodiments, the hydrogel forming composition comprise a second component comprising a protein that is capable of crosslinking with the crosslinking agent, and one or more solvents able to dissolve the first component and the second component such that when the first component and the second component are separately mixed with the one or more solvents, at least the second component is able to have a dissolution time at 25° C. of less than or equal to 30 seconds.

In certain embodiments, a method of forming a hydrogel tissue sealant is described. In some embodiments, the method comprises dissolving in a first solvent a first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the method comprises dissolving in a second solvent a second component, wherein the second component comprises a protein that is capable of crosslinking with the crosslinking agent, and combining the dissolved first component and the dissolved second component to form a hydrogel forming composition comprising the crosslinking agent, the protein, and a surfactant, to initiate crosslinking of the crosslinking agent and the protein, thereby forming the hydrogel tissue sealant.

According to certain embodiments, a method of forming a hydrogel tissue sealant comprises dissolving in a first solvent a first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In some embodiments, the method comprises dissolving in a second solvent a second component, wherein the second component comprises a protein that is capable of crosslinking with the crosslinking agent, and combining the dissolved first component and the dissolved second component to form a hydrogel forming composition comprising the crosslinking agent and the protein, thereby initiating crosslinking of the crosslinking agent and the protein to form the hydrogel tissue sealant such that crosslinking is characterized by a gel time less than or equal to 20 seconds.

In some embodiments, a method of forming a hydrogel tissue sealant comprises dissolving in a first solvent a first component to form a solution of the first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the method comprises dissolving in a second solvent a second component to form a solution of the second component, wherein the second component comprises a protein that is capable of crosslinking with the crosslinking agent and wherein the solution of the second component has a pH greater than or equal to 10.2 and less than or equal to 10.6, and combining the solution of the first component and the solution of the second component to form a hydrogel forming composition comprising the crosslinking agent and the protein, thereby initiating crosslinking of the crosslinking agent and the protein to form the hydrogel tissue sealant.

According to certain embodiments, a method of forming a hydrogel tissue sealant comprises dissolving in a first solvent a first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments, and each G is a leaving group independently selected from the group consisting of N-oxysuccinimidyl, N-oxymaleimidyl, N-oxyphthalimidyl, nitrophenoxyl, N-oxyimidazolyl, and tresyl. In some embodiments, the method comprises dissolving in a second solvent a second component, wherein the second component comprises a protein that is capable of crosslinking with the crosslinking agent, wherein the dissolution time of the second component in the second solvent at 25° C. is less than or equal to 30 seconds, and combining the dissolved first component and the dissolved second component to form a hydrogel forming composition comprising the crosslinking agent and the protein, thereby initiating crosslinking of the crosslinking agent and the protein to form the hydrogel tissue sealant.

In some embodiments, a method of forming a hydrogel tissue sealant comprises forming a hydrogel forming composition comprising a crosslinking agent that is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—$OD-C(O)—, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In some embodiments, the solution comprises a protein that is capable of crosslinking with the crosslinking agent, and a surfactant, wherein the hydrogel forming composition, upon formation, results in initiation of crosslinking of the crosslinking agent and the protein, thereby forming the hydrogel tissue sealant.

In some embodiments, a method of sealing tissue is described. In certain embodiments, the method comprises delivering a hydrogel forming composition to a tissue site, wherein the hydrogel forming composition comprises a reaction product of:

a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component comprising a protein that is capable of crosslinking with the crosslinking agent. In certain embodiments, the hydrogel forming composition further comprises a surfactant.

According to certain embodiments, a method of sealing tissue comprises delivering a hydrogel forming composition to a tissue site, wherein the hydrogel forming composition is a reaction product of:

a solution of a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a solution of a second component comprising a protein that is capable of crosslinking with the crosslinking agent, wherein the solution of the second component has a pH greater than or equal to 10.2 and less than or equal to 10.6.

According to some embodiments, a method of sealing tissue, comprises delivering a hydrogel forming composition to a tissue site, wherein the hydrogel composition comprises a reaction product of:

a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component comprising a protein that is capable of crosslinking with the crosslinking agent. In certain embodiments, the method comprises forming a hydrogel tissue sealant at the tissue site via a crosslinking reaction characterized by a gel time less than or equal to 20 seconds.

In certain embodiments, a kit for forming a hydrogel tissue sealant is described, wherein the kit comprises a first component contained within a first container, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the kit comprises a second component contained with a second container, wherein the second component comprises a protein that is capable of crosslinking with the crosslinking agent, and a surfactant.

According to some embodiments, a kit for forming a hydrogel tissue sealant comprises a first component in powder form contained within a first container, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In some embodiments, the kit comprises a second component in powder form contained with a second container, wherein the second component comprises a protein that is capable of crosslinking with the crosslinking agent, a first aqueous hydration solution contained within a third container, wherein the first aqueous hydration solution is able to dissolve the first component, and a second aqueous hydration solution contained with a fourth container, wherein the second aqueous hydration solution is able to dissolve the second component.

In certain embodiments, a kit for forming a hydrogel tissue sealant comprises one or more syringes collectively comprising at least three separate containers, wherein a first container comprises a first component in powder form, a second container comprises a second component in powder form, and at least a third container comprises one or more solvents, wherein the one or more syringes are configured such that the first container and the second container are able to be placed in fluid communication with the at least a third container comprising the one or more solvents to facilitate mixing of the first component with the one or more solvents to form a solution of the first component and to facilitate mixing of the second component with the one or more solvents to form a solution of the second component, and wherein the one or more syringes are further configured to mix the solution of the first component and the solution of the second component to form a crosslinking solution of the first component and the second component able to form the hydrogel tissue sealant, wherein the first component comprises an electrophilic biodegradable polymer and the second component comprises a nucleophilic biodegradable polymer able to crosslink with the electrophilic biodegradable polymer.

According to some embodiments, a hydrogel forming composition for forming a hydrogel tissue sealant comprises a first component comprising a crosslinking agent which is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl. In certain embodiments, the hydrogel forming composition comprises a second component comprising a protein that is capable of crosslinking with the crosslinking agent, and one or more solvents, wherein the first component and the second component are dissolved in the one or more solvents.

In certain embodiments of the hydrogel forming composition, the difunctionalized polyalkylene oxide-based component has the formula G-LM-$(OCH_2CH_2)_n$O-LM-G where n is an integer from 10 to 500, preferably 50 to 200.

In certain embodiments of the hydrogel forming composition the leaving group G in the difunctionalized polyalkylene oxide-based component is N-oxysuccinimidyl.

In certain embodiments of the hydrogel forming composition the difunctional linking moiety LM in the difunctionalized polyalkylene oxide-based component is selected from $-(CH_2)_b-C(O)-$ and $-C(O)-(CH_2)_c-C(O)-$, wherein b and c are both integers from 1 to 10.

In certain embodiments of the hydrogel forming composition the difunctionalized polyalkylene oxide-based component is selected from:

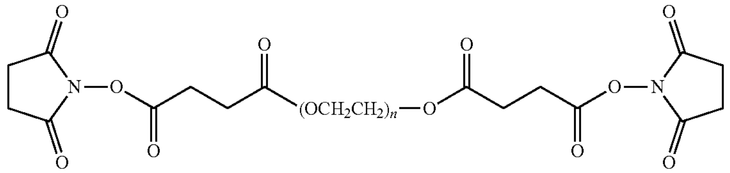

and

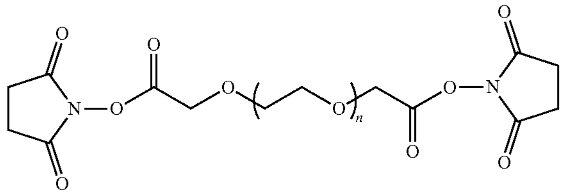

wherein in both formulae n is an integer from 10 to 500, preferably 50 to 200.

In certain embodiments of the hydrogel forming composition the protein is selected from the group consisting of human serum albumin, recombinant human serum albumin, and animal sourced albumin.

In certain embodiments of the hydrogel forming composition the protein is recombinant human serum albumin.

In certain embodiments of the hydrogel forming composition the composition further comprises a surfactant dissolved in the one or more solvents.

In certain embodiments of the hydrogel forming composition the surfactant is selected from a non-functionalized PEG preferably with a weight average molecular weight of 1000 g/mol to 40000 g/mol, dextran sulfate, a poloxamer, a polysorbate, an oil, a siloxane, a stearate, and/or a glycol.

In certain embodiments of the hydrogel forming composition the one or more solvents include water in an amount of 50 wt. % to 100 wt. %, preferably 90 wt. % to 100 wt. %, based on the total amount of solvent.

In certain embodiments of the hydrogel forming composition the difunctionalized polyalkylene oxide-based component is selected from:

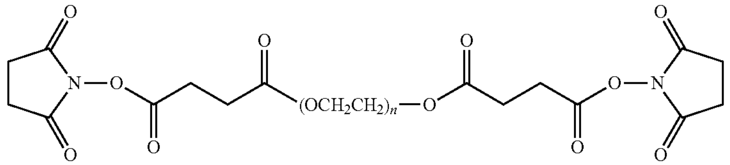

and

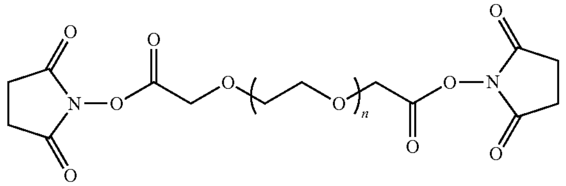

wherein in both formulae n is an integer from 10 to 500, preferably 50 to 200;

the protein is recombinant human serum albumin;

the surfactant is a non-functionalized PEG; and water makes up 90 wt. % or more of the total amount of the one or more solvents.

In certain embodiments of the hydrogel forming composition the composition further comprises a crosslinking initiator, an antioxidant, and/or a radiopaque agent.

In certain embodiments of the hydrogel forming composition the composition comprises a base or basic buffer, preferably a carbonate and/or a bicarbonate.

In certain embodiments of the hydrogel forming composition the composition comprises an antioxidant, preferably butylated hydroxyanisole, butylated hydroxytoluene, propyl gallate d-alpha tocopheryl polyethylene glycol-1000 succinate, or sodium metabisulfite, and/or mixtures thereof.

In certain embodiments of the hydrogel forming composition the composition comprises a radiopaque agent, preferably gold, silver, iodine, potassium chloride, barium sulfate, iohexol, or diatrizoate, and/or mixtures thereof.

In certain embodiments of the hydrogel forming composition a first component of the composition is dissolved in a first solvent.

In certain embodiments of the hydrogel forming composition a second component of the composition is dissolved in a second solvent.

In certain embodiments of the hydrogel forming composition a second component dissolved in the second solvent has a pH of from 10.2 to 10.6.

In certain embodiments kit for forming a hydrogel tissue sealant, comprising:

a first container containing a first component comprising the crosslinking agent as defined in this disclosure; a second container containing a second component comprising a protein, preferably a protein selected from the group consisting of human serum albumin, recombinant human serum albumin, and animal sourced albumin; and optionally one or more additional containers containing one or more solvents, preferably water, for dissolving the first component and the second component.

In certain embodiments a kit comprises a first container containing a first component; a second container containing a second component; and a third container containing a solvent, preferably water, for dissolving the first component and the second component.

In certain embodiments a kit comprises two syringes, wherein a first syringe comprises a first container and a second container; and wherein a second syringe comprises a third container; wherein a first component and a second component contained in the syringe are in powder form; wherein the first syringe and the second syringe are configured to be fluidically connectable to each other such that the first container and the second container are able to be placed in fluid communication with the third container to facilitate mixing of the first component and the second component with a solvent to form a solution of the first component in the first container and a solution of the second component in the second container, and wherein the first syringe is further configured to mix the solution of the first component and the solution of the second component to form a hydrogel forming composition for forming a hydrogel tissue sealant. In certain embodiments such kit comprises a first container containing the first component; a second container containing the second component; a third container containing a solvent, preferably water, for dissolving the first component; and a fourth container containing a solvent, preferably water, for dissolving the second component, and may further comprises two syringes, wherein a first syringe comprises the first container and the second container, and wherein a second syringe comprises the third container and the fourth container; wherein the first component and the second component are in powder form; wherein the first syringe and the second syringe are configured to be fluidically connectable to each other such that the first container and the second container are able to be placed in fluid communication with the third container and the fourth container, respectively, to facilitate mixing of the first component with the solvent in the third container to form a solution of the first component in the first container and to facilitate mixing of the second component with the solvent in the fourth container to form a solution of the second component in the second container, wherein the first syringe is further configured to mix the solution of the first component and the solution of the second component to form a hydrogel forming composition for forming a hydrogel tissue sealant.

In certain embodiments, any hydrogel forming composition described herein, and/or prepared using any kit described herein is suitable for use in a method of treatment by surgery. In certain embodiments, such method of treatment by surgery includes delivering the hydrogel forming composition to a tissue site and forming a hydrogel tissue sealant at that tissue site. In certain embodiments the treatment by surgery is a lung biopsy procedure, and wherein the composition is used to prevent or reduce the risk of pneumothorax during or after the lung biopsy procedure, which can be a procedure wherein any hydrogel forming composition described herein is delivered to the pleural space of the patient to form a hydrogel tissue sealant through which a biopsy sample is taken.

In certain embodiments, a kit for forming a hydrogel tissue sealant comprises a first container containing a first component comprising a crosslinking agent, a second container containing a second component comprising a protein, preferably a protein selected from the group consisting of human serum albumin, recombinant human serum albumin, and animal sourced albumin, and optionally one or more additional containers containing one or more solvents, preferably water, for dissolving the first component and the second component.

In some embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; a second component comprising a protein that is capable of crosslinking with the crosslinking agent, wherein the protein is at least partially deprotonated and/or the second component comprises a crosslinking initiator comprising a base and/or a buffer, wherein the conjugate acid of the base and/or buffer has a $pK_a$ of greater than or equal to 6; and one or more solvents able to dissolve the first component and the second component; and a surfactant; wherein when the first component, the second component, and the surfactant are all dissolved in the one or more solvents, crosslinking of the crosslinking agent and the protein occurs to form the hydrogel tissue sealant.

In some embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component comprising a protein that is capable of crosslinking with the crosslinking agent, wherein the protein is at least partially deprotonated and/or the second component comprises a crosslinking initiator comprising a base and/or buffer; and a surfactant; wherein the protein is present in the second component in an amount of greater than or equal to 80 wt. % versus the total weight of the protein, surfactant, and crosslinking initiator when present, wherein the crosslinking initiator when present does not exceed 16 wt % versus the total weight of the protein, surfactant, and crosslinking initiator, and wherein the surfactant is present in the second component in an amount of greater than or equal to 4 wt % versus the total weight of the protein, surfactant, and crosslinking initiator when present; and one or more solvents able to dissolve the first component and the second component; wherein when the first component and the second component are all dissolved in the one or more solvents, crosslinking of the crosslinking agent and the protein occurs to form the hydrogel tissue sealant.

In some embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas $—R—C(O)—$, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_d—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component comprising a protein that is capable of crosslinking with the crosslinking agent, wherein the second component is free of any basic salt or basic buffer or comprises a basic salt and/or basic buffer in an amount less than or equal to 10 wt % versus the total weight of the composition; and a first solvent able to dissolve the first component and a second solvent able to dissolve the second component; wherein when the second component is dissolved in the second solvent the pH of the solution of the second component in the second solvent is greater than or equal to 10 and less than or equal to 11 and wherein when the first component is dissolved in the first solvent and combined with the solution of the second component in the second solvent a crosslinking solution of the first component and the second component is formed.

In some embodiments, a hydrogel forming composition for forming a hydrogel tissue sealant comprises a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula $—C(O)—$, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas $—R—C(O)—$, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component comprising a protein that is capable of crosslinking with the crosslinking agent, wherein the second component is free of any powdered basic salt or buffer salt comprising a carbonate anion or bicarbonate anion or the second component comprises a powdered basic salt or buffer salt comprising a carbonate anion or bicarbonate anion in an amount less than 0.1 wt % versus the total weight of the second component; one or more solvents able to dissolve the first component and the second component; and a surfactant; wherein when the first component, the second component, and the surfactant are all dissolved in the one or more solvents, crosslinking of the crosslinking agent and the protein occurs to form the hydrogel tissue sealant.

In some embodiments, a method of sealing tissue is provided. In some embodiments, the method of sealing tissue comprises delivering a reaction product of a hydrogel forming composition described herein.

In some embodiments, a method of forming a hydrogel tissue sealant is provided. In some embodiments, a method of forming a hydrogel tissue sealant comprises dissolving in a first solvent a first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula $—C(O)—$, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas $—R—C(O)—$, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

dissolving in a second solvent a second component, wherein the second component comprises a protein that is capable of crosslinking with the crosslinking agent, wherein the second component is prepared by a method comprising removing liquid from a preparatory solution comprising the protein and a base and/or basic buffer, thereby forming a solid form of the second component, wherein a molar ratio of the amount of protein added to the preparatory solution to the amount of the base or basic buffer added to the preparatory solution is greater than or equal to 1:100, and combining the dissolved first component and the dissolved second component to form a hydrogel forming composition comprising the crosslinking agent, the protein, and a surfactant to initiate crosslinking of the crosslinking agent and the protein, thereby forming the hydrogel tissue sealant.

In some embodiments, a method of forming a hydrogel tissue sealant comprises dissolving in a first solvent a first component, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

dissolving in a second solvent a second component, wherein the second component comprises a protein that is capable of crosslinking with the crosslinking agent, wherein the second component is prepared by a method comprising removing liquid from a preparatory solution comprising the protein and a base or basic buffer, thereby forming a solid form of the second component, wherein the preparatory solution is formed by combining the protein with a base and/or basic buffer solution comprising the base or basic buffer at a molar concentration of less than or equal to 0.5 M, and combining the dissolved first component and the dissolved second component to form a hydrogel forming composition comprising the crosslinking agent, the protein, and a surfactant to initiate crosslinking of the crosslinking agent and the protein, thereby forming the hydrogel tissue sealant.

In some embodiments, a method for preparing a protein for use in a hydrogel forming composition is provided. In some embodiments, the method is for preparing a protein for use in a hydrogel forming composition comprising a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

the improvement comprising removing liquid from a preparatory solution comprising the protein and a base or basic buffer, thereby forming a solid form of a second component, wherein a molar ratio of the amount of protein added to the preparatory solution to the amount of the base or basic buffer added to the preparatory solution is greater than or equal to 1:100.

In some embodiments, the method is for preparing a protein for use in a hydrogel forming composition comprising a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C (O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

the improvement comprising removing liquid from a preparatory solution comprising the protein and a base or basic buffer, thereby forming a solid form of a second component, wherein the preparatory solution is formed by combining the protein with a base or basic buffer solution comprising the base or basic buffer at a molar concentration of less than or equal to 0.5 M.

In some embodiments, a kit for forming a hydrogel tissue sealant is provided. In some embodiments, the kit for forming a hydrogel tissue sealant comprises a first component contained within a first container, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component contained in a second container, wherein the second component comprises a protein that is capable of crosslinking with the crosslinking agent, wherein the protein is at least partially deprotonated and/or the second component comprises a crosslinking initiator comprising a base and/or a buffer, wherein the conjugate acid of the base and/or buffer has a $pK_a$ of greater than or equal to 6.

In some embodiments, a kit for forming a hydrogel tissue sealant comprises a first component contained within a first container, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component contained in a second container, wherein the second component comprises a protein that is capable of crosslinking with the crosslinking agent, wherein the protein is at least partially deprotonated and/or the second component comprises a crosslinking initiator comprising a base and/or buffer; and a surfactant; wherein the protein is present in the second component in an amount of greater than or equal to 80 wt. % versus the total weight of the protein, surfactant, and crosslinking initiator when present, wherein the crosslinking initiator when present does not exceed 16 wt % versus the total weight of the protein, surfactant, and crosslinking initiator, and wherein the surfactant is present in the second component in an amount of greater than or equal to 4 wt % versus the total weight of the protein, surfactant, and crosslinking initiator when present.

In some embodiments, a kit for forming a hydrogel tissue sealant comprises a first component contained within a first container, wherein the first component comprises a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component contained in a second container, wherein the second component comprises a protein that is capable of crosslinking with the crosslinking agent, wherein the second component is free of any basic salt or basic buffer or comprises a basic salt and/or basic buffer in an amount less than or equal to 10 wt % versus the total weight of the composition; and a first solvent contained within a third container able to dissolve the first component; and a second solvent contained within a fourth able to dissolve the second component; wherein when the second component is dissolved in the second solvent the pH of the solution of the second component in the second solvent is greater than or equal to 10 and less than or equal to 11.

In some embodiments, a kit for forming a hydrogel tissue sealant comprises a first component contained within a first container, wherein the first component comprises, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl; and a second component contained in a second container, wherein the second component comprises a protein that is capable of crosslinking with the crosslinking agent, wherein the second component is free of any powdered basic salt or buffer salt comprising a carbonate anion or bicarbonate anion or the second component comprises a powdered basic salt or buffer salt comprising a carbonate anion or bicarbonate anion in an amount less than 0.1 wt % versus the total weight of the second component.

According to certain embodiments, the hydrogel forming composition as described above or as prepared using the kit as described above may be used in a method of treatment by surgery.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
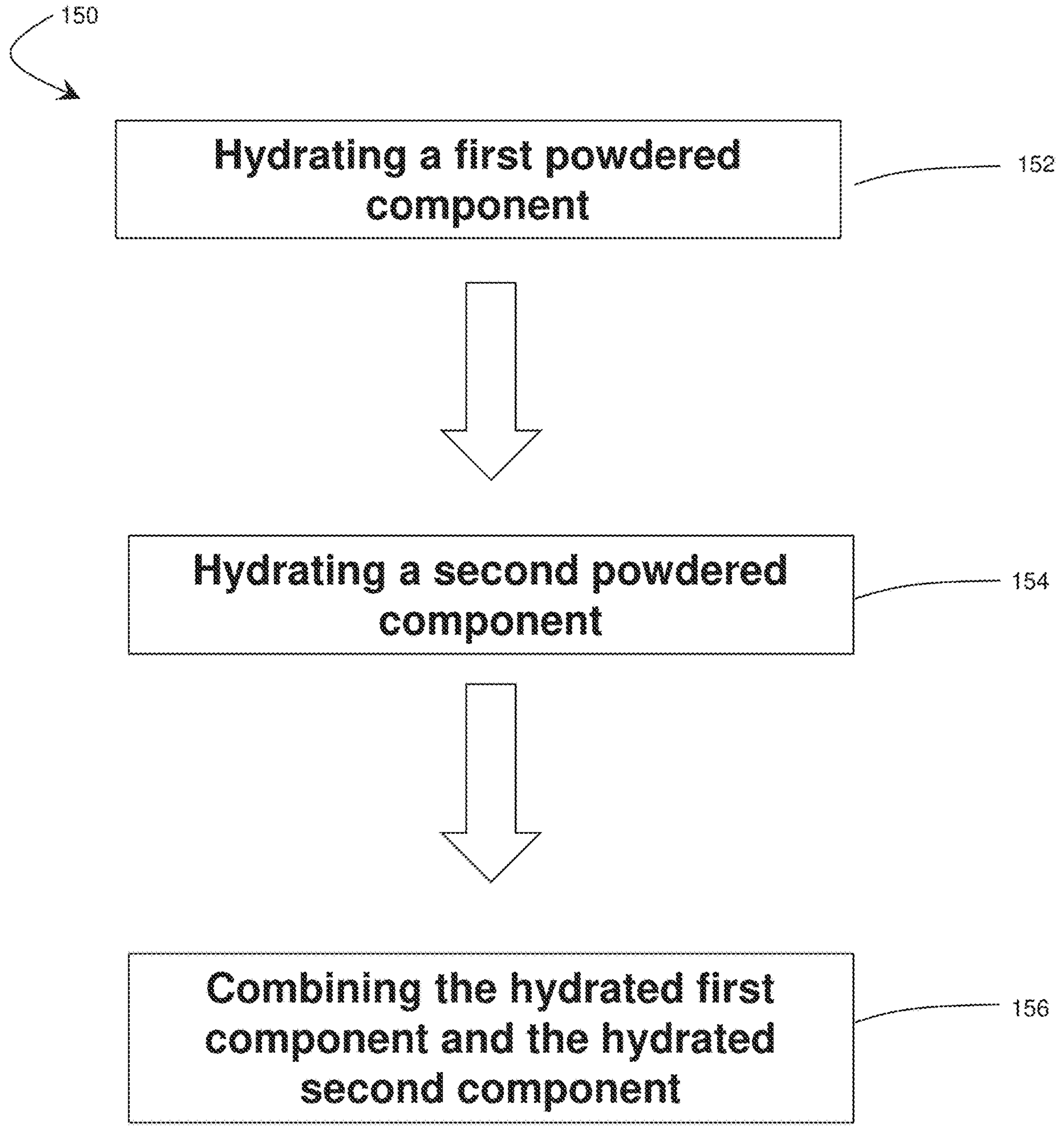
FIG. 1 shows, in accordance with certain embodiments, steps in an exemplary method for forming a hydrogel tissue sealant.

Compositions and methods related to hydrogel tissue sealants are generally described. In certain embodiments, a hydrogel forming composition is provided in dry form (e.g. as one or more powder mixtures) and comprises at least a crosslinking agent and a protein that is capable of crosslinking with the crosslinking agent. A solvent (i.e., one or more solvents) able to dissolve the crosslinking agent and the protein can be provided and used to dissolve the hydrogel forming composition to facilitate crosslinking. A surfactant that is capable of stabilizing the hydrogel forming composition, increasing the rate of dissolving the protein in the one or more solvents, and/or preventing aggregation of the protein can also be added, either to one or more components of the powder mixture or the one or more solvents. While in certain embodiments all of the ingredients of the composition may be part of a single dry mixture (e.g., a powder mixture), in other embodiments that may result in added stability and improved shelf life, the composition may be segregated into two or more reactive components (e.g. two or more dry powdered mixtures), with at least a first and a second component comprising an ingredient that reacts with one or more ingredients of another of the components. Preferably, in such embodiments, the ingredients in each of the components are not substantially reactive with other ingredients in such component, so that reaction can be prevented until the components are dissolved in one or more suitable solvents (e.g. hydrated) and combined prior to or during use, enabling them to react to form the hydrogel. In instances wherein the ingredients are segregated into components that are, with respect to the other ingredients in such component, not substantially reactive, the components may be formulated and stored in a hydrated, flowable form as opposed to a dry, non-hydrated form. In much of the discussion and examples below, the composition is provided as two dry powder components prior to hydration and mixing of the components to form a crosslinked hydrogel tissue sealant, but as indicated above, other dry and flowable formulations are possible.

In some instances, nucleophilic groups, e.g., of a protein (e.g., amino groups from amino acid side chains and/or an N-terminus) react with electrophilic groups of the crosslinking agent to accomplish crosslinking more rapidly when unprotonated than when protonated. To achieve this condition, some embodiments involve inclusion of separate solid base and/or basic buffers in the hydrogel forming composition (e.g., as part of the protein-containing second component or as a separate component) to elevate the pH of the reaction mixture upon hydration and cross-linking. An alternative or additional approach involves forming unprotonated nucleophilic groups such as on a protein (e.g., free amine groups) in a basic state (e.g., via at least partially deprotonating the protein prior to or during formation of the second component of the hydrogel forming composition), as described in more detail below. One example of such an approach is to dissolve a protein (e.g., albumin) in liquid (e.g., water) and adjust the pH of the liquid (e.g., water) to a basic pH, thereby at least partially deprotonating the protein, and then removing the liquid (e.g., water) to provide a pH-adjusted protein in dry powder form for use as or as part of a protein-containing second component of the hydrogel forming composition. In such example, the pH may be adjusted using a base and/or basic buffer, such as a strong base (e.g., a hydroxide ion-containing basic salt).

As one example, crosslinking to form the hydrogel tissue sealant may be initiated by combining a first component comprising the crosslinking agent with a second component comprising the protein. In certain embodiments, the surfactant may be part of the second component. The first component may further include, for example, an antioxidant (e.g., a first antioxidant), which can be selected to increase the stability of the crosslinking agent. The second component may further comprise a second antioxidant, which can be selected to increase the stability of the protein. As a result, the hydrogel forming composition can have both an increased shelf-life and enhanced storage capabilities as compared to other conventional hydrogel forming compositions. For example, in some embodiments, the hydrogel forming compositions described herein may be stored at room temperature for long periods of time (e.g., three years or more) without requiring refrigeration. Other advantages of the hydrogel forming compositions may include a shorter, tunable gel time, and an increased pot life, both of which are further described below in greater detail.

In certain embodiments, a multicomponent (e.g., two component, three component, four component) composition formulation may be used. In some embodiments, a first component comprises a difunctionalized polyalkylene oxide crosslinking agent, and a second component comprises a protein (e.g., lyophilized albumin) that is capable of crosslinking with the difunctionalized polyalkylene oxide. In certain embodiments, the second component may also comprise a crosslinking initiator (e.g., a base or basic buffer, such as sodium hydroxide and/or sodium carbonate and/or sodium bicarbonate) that initiates crosslinking of the crosslinking agent with the protein. In certain embodiments, as indicated above, the first component and the second component may both be provided and stored as powdered mixtures. The powdered mixtures may be separately or concurrently hydrated (e.g., with a solvent, such as water, a biocompatible organic solvent, or an aqueous solution), then combined (if separately hydrated), to form the hydrogel tissue sealant. In certain embodiments, the hydrating solution that hydrates the first component (and/or second component) may further comprise a radiopaque agent that permits the hydrogel tissue sealant to be, for example, spectroscopically visible. The hydrating solution that hydrates the second component (and/or first component) may comprise an anti-foaming additive, such as a poloxamer. In certain embodiments, the anti-foaming additive may assist in refolding of the protein upon hydration.

The hydrogel forming composition may be used to bond or seal tissue in vivo. In certain non-limiting embodiments, for example, it may be particularly useful to use the hydrogel forming composition as a pleural lung sealant to seal off air or fluid from entering the pleural space. In some such embodiments, the hydrogel lung sealant may advantageously decrease the occurrence of complications during and/or following the lung biopsy procedure, such as, for example, pneumothorax. In certain embodiments, in addition to, or instead of, use as a hydrogel tissue sealant, compositions and methods described herein may be useful for or adaptable to be useful for a variety of other medical applications, such as, without limitation, a postsurgical adhesion barrier and/or a wound dressing material.

As used herein, the term "crosslink" refers to a chemical reaction between two or more similar or dissimilar polymers, copolymers, oligomers, and/or macromers that links the two or more similar or dissimilar polymers, copolymers, oligomers, or macromers via formation of at least one covalent bond and/or ionic bond, or a chain extension between one or more polymers, copolymers, oligomers, and/or macromers to provide a longer chain of the one or more polymers, copolymers, oligomers, and/or macromers via formation of at least one covalent bond and/or ionic bond.

Electrophilic Crosslinking Agents

According to certain embodiments, the hydrogel forming composition comprises an electrophilic biodegradable polymer. In certain embodiments, the electrophilic biodegradable polymer may be a synthetic or naturally occurring polymer that contains or is functionalized to contain one or more, and preferably two or more, reactive electrophilic groups. Many suitable electrophilic biodegradable polymers are known to those of ordinary skill in the art. In some embodiments, for example, a particularly advantageous and preferred crosslinking agent of the hydrogel forming composition comprises a difunctionalized polyalkylene oxide. In certain embodiments, the difunctionalized polyalkylene oxide has a composition described by the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula —$(CH_2)_b$—C(O)— where b is an integer from 1 to 10, a diester radical of the formula —C(O)—$(CH_2)_c$—C(O)— where c is an integer from 1 to 10 and where the aliphatic portion of the radical may be saturated or unsaturated, a dicarbonate diradical of the formula —C(O)—O—$(CH_2)_d$—O—C(O)— where d is an integer from 1 to 10, an amide containing diradical of the formula —N(H)—C(O)—$(CH_2)_d$—C(O)— where d is an integer from 1 to 10, an amide containing diradical of the formula —$(CH_2)_c$—C(O)—N(H)—$(CH_2)_d$— where c is an integer from 1 to 10 and d is an integer from 1 to 10, and an oligomeric diradical represented by the formulas —R—C(O)—, —R—C(O)—$(CH_2)_c$—C(O)—, —R—C(O)—O—$(CH_2)_d$—O—C(O)—, —R—N(H)—C(O)—$(CH_2)_d$—C(O)—, or —R—$(CH_2)_c$—C(O)—N(H)—$(CH_2)_d$— where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl.

According to certain embodiments, the crosslinking agent is a difunctionalized polyalkylene oxide of the formula:

G-LM-PEG-LM-G;

wherein:

PEG is polyethylene glycol;

each LM is the same and is a difunctional linking moiety represented by the formulas —C(O)—, —$(CH_2)_b$—C(O)— where b is an integer from 1 to 5, —C(O)—$(CH_2)_c$—C(O)— where c is an integer from 2 to 10 and where the aliphatic portion of the radical may be saturated or unsaturated, —C(O)—O—$(CH_2)_d$—O—C(O)— where d is an integer from 2 to 10, and an oligomeric diradical represented by the formulas —R—C(O)—, —R—$C(O)_c$—$(CH_2)_c$—C(O)—, or —R—C(O)—O—$(CH_2)_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments; and each G is the same and is a leaving group selected from the group of N-oxysuccinimidyl, N-oxymaleimidyl, N-oxyphthalimidyl, nitrophenoxyl, N-oxyimidazolyl, and tresyl.

According to some embodiments, the hydrogel forming composition comprises any of a variety of suitable crosslinking agents (e.g., difunctionalized polyalkylene oxides). In some embodiments, the crosslinking agent is or includes:

a 2-arm PEG disuccinimidyl succinate ($PEG(SS)_2$) of the form:

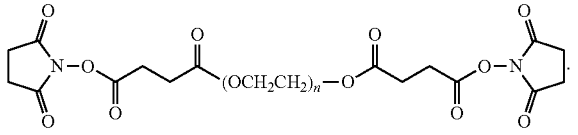

In certain embodiments, the crosslinking agent is or includes:

a 2-arm PEG carboxymethyl ester of the form:

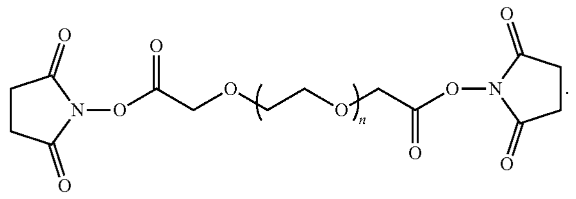

According to certain embodiments, the crosslinking agent (e.g., a difunctionalized polyalkylene oxide) of the formula G-LM-PEG-LM-G may have any of a variety of suitable weight average molecular weights. For example, in certain embodiments, the degree of ethoxylation in PEG (and the value for n in the formulae above) is such that the crosslinking agent may have a weight average molecular weight of greater than or equal to 1 kDa, greater than or equal to 2 kDa, greater than or equal to 3 kDa, greater than or equal to 4 kDa, greater than or equal to 5 kDa, greater than or equal to 10 kDa, or greater than or equal to 15 kDa. In certain embodiments, the crosslinking agent may have a weight average molecular weight of less than or equal to 20 kDa, less than or equal to 15 kDa, less than or equal to 10 kDa, less than or equal to 5 kDa, less than or equal to 4 kDa, less than or equal to 3 kDa, or less than or equal to 2 kDa. Combinations of the above recited ranges are also possible (e.g., the crosslinking agent may have a weight average molecular weight of greater than or equal to 1 kDa and less than or equal to 20 kDa, the crosslinking agent may have a weight average molecular weight of greater than or equal to 3 kDa and less than or equal to 5 kDa). Other ranges are also possible. In certain embodiments, for the formulae of the 2-arm PEG disuccinimidyl succinate and the 2-arm PEG carboxymethyl ester shown above, n is in the range of 10 to 500, more preferably 50 to 200. In some embodiments, the weight average molecular weight of the crosslinking agent is determined using size exclusion chromatography-multi-angle laser light scattering (SEC-MALLS).

According to certain embodiments, difunctionalized polyalkylene oxide crosslinking agents describable by the formula G-LM-PEG-LM-G, such as but not limited to the examples noted above, may be prepared by any of a variety suitable synthetic methods known to those skilled in the art. For example, see, U.S. Pat. No. 6,576,263 issued on Jun. 10, 2003 to Truong et al.; U.S. Reissued Pat. No. RE38,827 issued on Oct. 11, 2005 to Barrows et al.; and U.S. Reissued Pat. No. RE38,158 issued on Jun. 24, 2003 to Barrows et al.; each of which are incorporated herein by reference in its entirety for all purposes.

In some embodiments, difunctionalized polyalkylene oxides describable by the formula G-LM-PEG-LM-G may be prepared using known processes, procedures, or synthetic methods such as the procedures reported in U.S. Pat. No. 4,101,380, issued on Jul. 18, 1978 to Rubinstein or U.S. Pat. No. 4,839,345, issued on Jun. 13, 1989 to Doi et al., the procedure reported in International Application Publication No. WO/1990/013540 by Zalipsky, published on Nov. 15, 1990 from International Application No. PCT/US90/02133 filed Apr. 19, 1990 or the procedure reported by Abuchowski et al., Cancer Biochem. Biophys., 7:175-186 (1984), each of which are incorporated herein by reference in its entirety. Briefly, in certain embodiments, a polyalkylene oxide-based compound (e.g., polyethylene glycol discussed below as exemplary) and a suitable acid anhydride are dissolved in a suitable polar organic solvent in the presence of base and refluxed for a period of time sufficient to form a polyethylene glycol diester diacid. The diester diacid is then reacted with a leaving group, such as a N-hydroxy imide compound, in a suitable polar organic solvent in the presence of dicyclohexylcarbodiimide or another condensing agent, and stirred at room temperature to form the desired difunctional crosslinking agent.

All or some of the difunctionalized polyalkylene oxide-based compounds describable by the formula G-LM-PEG-LM-G may be purchased from commercial sources, including, but not limited to, NOF America Corporation, Laysan Bio, Inc, Sigma-Aldrich, and/or JenKem Technology USA. The difunctionalized polyalkylene oxide-based compounds may also be readily synthetized by persons of ordinary skill in the chemical synthesis art in view of the teaching and exemplary methods described herein for exemplary compositions, published literature, and the level of ordinary skill and knowledge of the skilled artisan.

In certain non-limiting embodiments. $PEG(SS)_2$ can be synthesized by obtaining a linear PEG with an average weight average molecular weight of 3,350 Da, representing 75.7 oxyethylene repeat units. The linear PEG can be obtained, for example, from Dow Chemical Company. In some embodiments, the linear PEG may be converted to $PEG(SS)_2$ via a two-step synthesis. For instance, in some examples, the first step may comprise reacting the linear PEG with two equivalents of succinic anhydride to form an ester. The second step may comprise reacting the ester with two equivalents of the N-hydroxysuccinimide (NHS) to produce the crosslinking agent $PEG(SS)_2$, resulting in a white solid of a 2-arm crosslinking agent that possesses two succinimidyl groups per molecule.

In certain embodiments, difunctionalized polyalkylene oxide-based compounds of the formula G-LM-PEG-LM-G comprise a leaving group G (e.g., N-oxysuccinimidyl, N-oxymaleimidyl, N-oxyphthalimidyl, nitrophenoxyl, N-oxyimidazolyl, and tresyl). In such embodiments, leaving group G is an electrophilic leaving group that is capable of reacting with (e.g., being displaced by) a nucleophilic group, for example an amine group of a protein. For example, when G is N-oxysuccinimidyl, G-LM-PEG-LM-G comprises an NHS ester electrophilic group comprising an N-oxy-succinimidyl leaving group. According to certain embodiments, the leaving group G reacts with an amino group of the nucleophile (e.g., amine group of a protein) to produce a crosslinked composition by formation of amide bonds upon release of the leaving group G. Referring back to the example above, the N-oxy-succinimidyl leaving group of the G-LM-PEG-LM-G comprising the NHS ester electrophilic group reacts with (is displaced by) an amine group of the protein (or of a modified polysaccharide—or in general by an amino group of any suitable amino-functionalized or containing nucleophilic polymer) resulting in a crosslinked composition having an amide bond upon release of the N-oxy-succinimide. Such reactivity is further described in U.S. Pat. No. 6,458,147 issued on Oct. 1, 2002 to Cruise et al., which is incorporated herein by reference in its entirety.

According to certain embodiments, the purity of the difunctionalized polyalkylene oxide crosslinking agent may be determined by its percent difunctionality. A high percentage of difunctionality may advantageously result in a higher degree and/or rate of crosslinking to provide the a hydrogel formed from the hydrogel forming composition with enhanced performance characteristics, such as a fast gel time, a longer pot life, and/or a longer shelf life, and/or improved mechanical properties or resorption time, each of which are explained below in greater detail. In some embodiments, the difunctionalized polyalkylene oxide crosslinking agent has a percent difunctionality greater than or equal to 75 wt. %, greater than or equal to 80 wt. %, greater than or equal to 85 wt. %, greater than or equal to 90 wt. %, greater than or equal to 95 wt. %, or greater than or equal to 99 wt. %. In certain embodiments, the difunctionalized polyalkylene oxide crosslinking agent has a percent difunctionality between 70 wt. % and 99.9 wt. %, or between 90 wt. % and 95%. Other ranges are also possible. The percent difunctionality of the difunctionalized polyalkylene oxide crosslinking agent as used herein is determined by high-performance liquid chromatography (HPLC.

In a powdered form, the difunctionalized polyalkylene oxide crosslinking agent may have a relatively low weight percent moisture content. A low weight percent moisture content for the powdered difunctionalized polyalkylene oxide crosslinking agent can advantageously provide a hydrogel forming composition with an improved shelf life, as hydrolysis of the difunctionalized polyalkylene oxide is reduced, therefore preserving reactivity of the crosslinking agent over storage time. In certain embodiments, for example, the weight percent moisture content of the powdered difunctionalized polyalkylene oxide crosslinking agent may be less than or equal to 10 wt. %, less than or equal to 9 wt. %, less than or equal to 8 wt. %, less than or equal to 7 wt. %, less than or equal to 6 wt. %, less than or equal to 5 wt. %, less than or equal to 4 wt. %, less than or equal to 3 wt. %, or less than or equal to 2 wt. % based on the total weight of the powdered difunctionalized polyalkylene oxide crosslinking agent. In certain embodiments, the weight percent moisture content of the powdered crosslinking agent may be between 1 wt. % and 10 wt. % based on the total weight of the powdered difunctionalized polyalkylene oxide crosslinking agent, or between 4 wt. % and 6 wt. % based on the total weight of the powdered difunctionalized polyalkylene oxide crosslinking agent. Other ranges are also possible. The weight percent moisture content as stated herein is determined using a moisture analyzer and/or a Karl-Fischer titration.

According to certain embodiments, the hydrogel forming composition comprises the powdered crosslinking agent in any of a variety of suitable amounts in weight percent (wt. %) by mass versus the total weight of the powdered hydrogel forming composition. For example, in some embodiments, the hydrogel forming composition comprises the crosslinking agent in an amount, on a powdered basis, greater than or equal to 10 wt. %, greater than or equal to 15 wt. %, greater than or equal to 20 wt. %, greater than or equal to 25 wt. %, greater than or equal to 30 wt. %, greater than or equal to 35 wt. %, greater than or equal to 40 wt. %, greater than or equal to 45 wt. %, greater than or equal to 50 wt. %, or greater than or equal to 55 wt. % of the total weight of the powdered hydrogel forming composition. In certain embodiments, the hydrogel forming composition comprises the crosslinking agent, on a powdered basis, in an amount less than or equal to 60 wt. %, less than or equal to 55 wt. %, less than or equal to 50 wt. %, less than or equal to 45 wt. %, less than or equal to 40 wt. %, less than or equal to 35 wt. %, less than or equal to 30 wt. %, less than or equal to 25 wt. %, less than or equal to 20 wt. %, or less than or equal to 15 wt. % of the total weight of the powdered hydrogel forming composition. Combinations of the above recited ranges are also possible (e.g., the hydrogel forming composition comprises the crosslinking agent in an amount, on a powdered basis, greater than or equal to 10 wt. % and less than or equal to 60 wt. % of the total weight of the powdered hydrogel forming composition, the hydrogel forming composition comprises the crosslinking agent in an amount, on a powdered basis, greater than or equal to 25 wt. % and less than or equal to 30 wt. % of the total weight of the powdered hydrogel forming composition). Other ranges are also possible.

Nucleophilic Biodegradable Polymers, Such as Proteins

In certain embodiments, the hydrogel forming composition comprises a nucleophilic biodegradable polymer that is able to crosslink with the electrophilic biodegradable polymer. In certain embodiments, the nucleophilic biodegradable polymer may be a synthetic or naturally occurring polymer that contains or is functionalized to contain one or more, and preferably two or more, reactive nucleophilic groups. Many suitable nucleophilic biodegradable polymers are known to those of ordinary skill in the art. In some embodiments, for example, a particularly advantageous and preferred nucleophilic biodegradable polymer is a protein. According to some embodiments, for example, the hydrogel forming composition comprises a protein that is capable of crosslinking with the above described electrophilic crosslinking agents (e.g., $PEG(SS)_2$). In certain embodiments, the protein comprises serum albumin (SA). The serum albumin may be, in some embodiments, human serum albumin (HSA) derived from donor blood. In some instances, the serum albumin is recombinant human serum albumin (rHSA) expressed in yeast and/or rice. In some instances, the serum albumin is animal sourced albumin, such as, for example, bovine serum albumin (BSA). According to certain embodiments, the protein (e.g., rHSA) may be lyophilized. Lyophilization of the protein may advantageously impede the degradation of the protein and improve shelf life and/or dissolution time when dissolved in an aqueous solvent, as described below, according to some embodiments.

In certain non-limiting embodiments, the protein may be Cohn analog culture grade BSA obtained from Proliant Biologicals. In some embodiments, the recombinant human serum albumin may be Cellastim recombinant human serum albumin, Healthgen recombinant human serum albumin, Optibumin recombinant human serum albumin, InVitria human serum albumin, or Albumedix human serum albumin.

In certain embodiments, the protein may be or include collagen or gelatin. Other proteins are also possible.

According to certain embodiments, the purity and/or amount of protein aggregation may be determined by the percent of the amount of monomer of the protein in the protein source. In certain embodiments, for example, the protein may comprise greater than or equal to 60 wt. % protein monomer, greater than or equal to 65 wt. % protein monomer, greater than or equal to 70 wt. % protein monomer, greater than or equal to 75 wt. % protein monomer, greater than or equal to 80 wt. % protein monomer, greater than or equal to 85 wt. % protein monomer, greater than or equal to 90 wt. % protein monomer, or greater than or equal to 95 wt. % protein monomer. In certain embodiments, the protein comprises less than or equal to 99 wt. % protein monomer, less than or equal to 95 wt. % protein monomer, less than or equal to 90 wt. % protein monomer, less than or equal to 85 wt. % protein monomer, less than or equal to 80 wt. % protein monomer, less than or equal to 75 wt. % protein monomer, less than or equal to 70% protein monomer, less than or equal to 70 wt. % protein monomer, or less than or equal to 65 wt. % protein monomer. Combinations of the above recited ranges are also possible (e.g., the protein comprises greater than or equal to 60 wt. % protein monomer and less than or equal to 99 wt. % protein monomer, the protein comprises greater than or equal to 90 wt. % protein monomer and less than or equal to 95 wt. % protein monomer). Other ranges are also possible. As is explained in further detail below, certain components of the hydrogel forming composition (e.g., the surfactant and/or anti-foaming agent) may act to prevent aggregation and/or the formation of protein dimers or higher order multimeric structures.

The powdered protein may have a relatively low weight percent moisture content. In certain embodiments, for example, the weight percent moisture content of the powdered protein component may be greater than or equal to 1 wt. %, greater than or equal to 2 wt. %, greater than or equal to 3 wt. %, greater than or equal to 4 wt. %, greater than or equal to 5 wt. %, greater than or equal to 6 wt. %, greater than or 7 wt. %, greater than or equal to 8 wt. %, or greater than or equal to 9 wt. % versus the total weight of the powdered protein component. In some embodiments, the weight percent of moisture content of the powdered protein may be less than or equal to 10 wt. %, less than or equal to 9 wt. %, less than or equal to 8 wt. %, less than or equal to 7 wt. %, less than or equal to 6 wt. %, less than or equal to 5 wt. %, less than or equal to 4 wt. %, less than or equal to 3 wt. %, or less than or equal to 2 wt. % versus the total weight of the powdered protein component. Combinations of the above recited ranges are also possible (e.g., the percent moisture content of the powdered protein may be between greater than or equal to 1 wt. % and less than or equal to 10 wt. % versus the total weight of the powdered protein component, the percent moisture content of the powdered protein may be between greater than or equal to 4 wt. % and less than or equal to 6 wt. % versus the total weight of the powdered protein component). Other ranges are also possible. As explained herein, the weight percent of moisture content is determined using a moisture analyzer and/or a Karl-Fischer titration.

According to certain embodiments, an overall powdered hydrogel forming composition comprises the protein (e.g., albumin) in any of a variety of suitable amounts in weight percent (wt. %) by mass versus the total weight of the powdered hydrogel forming composition (i.e., based on the combined weight of both the protein containing powdered component and the electrophilic polymer containing crosslinking agent powdered component). For example, in certain embodiments, the hydrogel forming composition comprises the protein in an amount, on a powdered basis, greater than or equal to 40 wt. %, greater than or equal to 45 wt. %, greater than or equal to 50 wt. %, greater than or equal to 55 wt. %, greater than or equal to 60 wt. %, greater than or equal to 65 wt. %, greater than or equal to 70 wt. %, or greater than or equal to 75 wt. % of the total weight of the powdered hydrogel forming composition. In certain embodiments, the hydrogel forming composition comprises the protein, on a powdered basis, in an amount of less than or equal to 80 wt. %, less than or equal to 75 wt. %, less than or equal to 70 wt. %, less than or equal to 65 wt. %, less than or equal to 60 wt. %, less than or equal to 55 wt. %, less than or equal to 50 wt. %, or less than or equal to 45 wt. % of the total weight of the powdered hydrogel forming composition. Combinations of the above recited ranges are also possible (e.g., the hydrogel forming composition comprises the protein in an amount, on a powdered basis, greater than or equal to 40 wt. % and less than or equal to 80 wt. % of the total weight of the powdered hydrogel forming composition, the hydrogel forming composition comprises the protein in an amount, on a powdered basis, greater than or equal to 55 wt. % and less than or equal to 65 wt. % of the total weight of the powdered hydrogel forming composition). Other ranges are also possible.

The ratio of the leaving group G (e.g., NHS) in the difunctionalized polyalkylene oxide-based compound of the formula G-LM-PEG-LM-G to the number of amine groups (e.g., of the protein) can be any of variety of suitable ratios. In certain embodiments, for example, the ratio of the leaving group G to the amine groups is greater than or equal to 0.5:1, greater than or equal to 1:1, greater than or equal to 1.5:1, greater than or equal to 2:1, or greater than or equal to 2.5:1. In some embodiments, the ratio of the leaving group G to the amine groups is less than or equal to 3:1, less than or equal to 2.5:1, less than or equal to 2:1, less than or equal to 1.5:1, or less than or equal to 1:1. Combinations of the above recited ranges are also possible (e.g., the ratio of the leaving group G to the amine groups is greater than or equal to 0.5:1 and less than or equal to 3:1, the ratio of the leaving group G to the amine groups is greater than or equal to 2:1 and less than or equal to 2.5:1). Other ranges are also possible.

In certain non-limiting embodiments, the crosslinking agent is $PEG(SS)_2$ and the protein is rHSA, and the ratio of NHS groups of $PEG(SS)_2$ to amine groups of rHSA is 2.21:1. In other non-limiting embodiments, the crosslinking agent is $PEG(SS)_2$ and the protein is rHSA, and the ratio of NHS groups of $PEG(SS)_2$ to amine groups of rHSA is 2.65:1. In other non-limiting embodiments, the crosslinking agent is $PEG(SS)_2$ and the protein is rHSA, and the ratio of NHS groups of $PEG(SS)_2$ to amine groups of rHSA is 2.64:1.

Crosslinking Initiators

In some embodiments, the crosslinking reactions that occur between the electrophilic crosslinking agent and the nucleophile (e.g., protein) are pH sensitive. In certain such embodiments, for example, the crosslinking reactions are inhibited at acidic pH and can be initiated and sustained by increasing the pH to neutral or basic values. In some embodiments, the hydrogel forming composition comprises a crosslinking initiator that initiates crosslinking of the crosslinking agent with the nucleophile (e.g., protein). In certain embodiments, the crosslinking initiator may be combined as a powder mixture with the protein. In some such embodiments, the crosslinking initiator may be lyophilized with the protein.

In certain embodiments, the crosslinking initiator may be, in some embodiments, a base or a basic buffer. In certain embodiments, for example, the crosslinking initiator comprises a base and/or basic buffer that facilitates the reaction between the leaving group G in a difunctionalized polyalkylene oxide-based compound of the formula G-LM-PEG-LM-G and the amine group of a protein. The base or basic buffer may be provided in any of a variety of forms. In some embodiments, the crosslinking initiator is part of the second component of the hydrogel forming composition. For example, the base or basic buffer may be present as a separate solid in the second component (e.g., as separate particles of a dry powder and/or as a separate region of a composite particle). However, in some embodiments, the crosslinking initiator is provided in a different manner, such as a third component of the hydrogel forming composition (e.g., a third dry powder). In some embodiments, a crosslinking initiator is a portion of the nucleophilic polymer, e.g., protein, such as a chemically-modified portion of a protein (e.g., a deprotonated amino acid side chain). For example, in some embodiments, a protein of the second component of the hydrogel forming composition is at least partially deprotonated to form free amine groups acting as an initiator, as described in more detail below. A protein may be at least partially deprotonated prior to inclusion in the hydrogel forming composition, such that the protein acts as both a crosslinking reactant component and as an initiator of the crosslinking reaction. Any of a variety of suitable bases or basic buffers may be utilized. In certain embodiments in which the nucleophilic compound comprises amine groups that react with the crosslinking agent, the basic crosslinking initiator is a base and/or basic buffer that does not include amine functionalities. In some embodiments, the base comprises a carbonate and/or a bicarbonate (e.g., a carbonate and/or a bicarbonate salt). For example, in certain embodiments, the base or basic buffer comprises sodium carbonate. In some embodiments, the base or basic buffer comprises sodium bicarbonate. Other bases or basic buffers are possible.

As mentioned above, in some embodiments the hydrogel forming composition comprises a crosslinking initiator, and the crosslinking initiator is a base, base-treated portion of a protein and/or other nucleophilic polymer—e.g. an amino-containing or amino-functionalized polymer, and/or basic buffer. The conjugate acid of the base and/or basic buffer may have a $pK_a$ suitable for initiating the nucleophile/electrophile reaction between the nucleophilic groups (e.g., amino groups) of the protein and/or other nucleophilic polymer and electrophilic groups of the crosslinking agent (e.g., $PEG(SS)_2$) as part of a crosslinking reaction. For example, when a separate base and/or basic buffer is used or present as the initiator, it may have a $pK_a$ sufficiently high to at least partially deprotonate amino acid side chains of a protein (e.g., lysines of a serum albumin) upon exposure to an aqueous liquid (e.g., water, saline solution, phosphate-buffered saline, etc.). In some, but not necessarily all embodiments, the base and/or basic buffer is non-nucleophilic. In some embodiments, the base and/or basic buffer does not include amine functionalities. Those of ordinary skill in the art are familiar with non-nucleophilic bases or basic buffers. A lack of amine functionalities may advantageously avoid nucleophilic reactions between the base and/or basic buffer and the electrophilic groups of the crosslinking agent ($PEG(SS)_2$) that could compete with the desired crosslinking reactions with the protein and/or other nucleophilic polymer.

In some embodiments, the base and/or basic buffer is a salt comprising a cation and an anion. The salt may be, for example, an inorganic salt. In some such embodiments, the cation is an alkali metal cation (e.g., a lithium ion, a sodium ion, and potassium ion, etc.). In some embodiments, the basic anion is an oxyanion. The oxyanion may be, for example, bicarbonate or carbonate. In some embodiments, the oxyanion is a phosphate anion (e.g., dibasic phosphate, $HPO_4^{2-}$). In some embodiments, the oxyanion is a borate ($BO_3^-$) or metaborate ($BO_2^-$) anion. In some embodiments, the base and/or basic buffer comprises a cation and hydroxide ($OH^-$). Non-limiting examples of potentially suitable bases and/or basic buffers include sodium bicarbonate, sodium carbonate, sodium phosphate (e.g., sodium phosphate dibasic, $Na_2HPO_4$), and sodium hydroxide (NaOH). For example, in some embodiments, the base and/or basic buffer of the crosslinking initiator comprises sodium hydroxide.

In some embodiments, the base and/or basic buffer is a relatively strong base. That is, in some embodiments, the conjugate acid of the base and/or buffer of the crosslinking initiator has a relatively high $pK_a$. It has been observed in the context of the present disclosure that inclusion of a relatively strong base and/or buffer can result in relatively small amounts of base and/or buffer being required to facilitate crosslinking reactions (e.g., with the crosslinking reagent). Use of relatively small amounts of the crosslinking initiator (due to the base and/or buffer being a relatively strong base) can allow for comparatively improved dissolution properties of the components (e.g., by allowing for greater incorporation of dissolution-improving agents such as surfactants) and/or improved stability of resulting hydrogels relative to compositions employing larger amounts of crosslinking initiator (e.g., due to using weak bases and/or buffers as crosslinking initiators). Additionally, use of relatively small amounts of the crosslinking initiator (due to the base and/or buffer being a relatively strong base) can allow for comparatively higher relative amounts of other components of the composition, such as surfactants (e.g., polyethylene glycol) relative to compositions employing larger amounts of crosslinking initiator (e.g., due to using weak bases and/or buffers as crosslinking initiators). Increased amounts of surfactant may facilitate easier hydration of the second component compared to compositions using weak bases and/or buffers as crosslinking initiators. In some embodiments, the conjugate acid of the base and/or buffer has a $pK_a$ of greater than or equal to 6, greater than or equal to 6.36, greater than or equal to 7, greater than or equal to 8, greater than or equal to 9, greater than or equal to 10, greater than or equal to 10.33, greater than or equal to 10.5, greater than or equal to 11, greater than or equal to 13, greater than or equal to 14, greater than or equal to 15, greater than or equal to 15.7, or greater. Unless explicitly stated otherwise, $pK_a$ values mentioned in this disclosure refer values in water. In some embodiments, the conjugate acid of the base and/or buffer has a $pK_a$ of less than or equal to 15.7, less than or equal to 15, less than or equal to 14, less than or equal to 13, or less. Combinations of these ranges (e.g., greater than or equal to 6 and less than or equal to 15.7, greater than or equal to 10.5 and less than or equal to 15.7, greater than or equal to 10.5 and less than or equal to 14) are possible. As mentioned above, in some embodiments the base comprises hydroxide ion (e.g., the base may be sodium hydroxide), which has a conjugate acid ($H_2O$) having a $pK_a$ of 15.7.

The crosslinking reaction between the leaving group G and the amine group of the nucleophile (e.g., protein) may occur at any of a variety of suitable pH values. In some embodiments, the crosslinking reaction is favored at high pH values. In certain embodiments, for example, the crosslinking reaction between the leaving group G and the amine group of the nucleophile (e.g., protein) is initiated and occurs at a pH greater than or equal to 7, greater than or equal to 8, greater than or equal to 9, greater than or equal to 10, or greater than or equal to 11. In certain embodiments, the crosslinking reaction between the leaving group G and the amine group of the nucleophile is initiated and occurs at a pH less than or equal to 12, less than or equal to 11, less than or equal to 10, or less than or equal to 9. Combinations of the above recited ranges are also possible (e.g., the crosslinking reaction between the leaving group G and the amine group of the nucleophile is initiated and occurs at a pH between greater than or equal to 7 and less than or equal to 11, the crosslinking reaction between the leaving group G and the amine group of the nucleophile is initiated and occurs at a pH between greater than or equal to 8 and less than or equal to 11, the crosslinking reaction between the leaving group G and the amine group of the nucleophile is initiated and occurs at a pH between greater than or equal to 9 and less than or equal to 11, or the crosslinking reaction between the leaving group G and the amine group of the nucleophile is initiated and occurs at a pH between greater than or equal to 10 and less than or equal to 11. Other ranges are also possible.

In certain non-limiting embodiments, the crosslinking reaction between the leaving group G and the amine group of the nucleophile (e.g. protein) can be initiated to occur at a pH suitable for facilitating reaction by combining a solution of the crosslinking agent with a solution of the nucleophile, wherein the pH of the solution of the nucleophile is between greater than or equal to 10 and less than or equal to 11. In certain non-limiting embodiments, the crosslinking reaction between the leaving group G and the amino group of the nucleophile (e.g., amine groups of a protein) can be initiated to occur at a pH suitable for facilitating reaction by combining a solution of the crosslinking agent with a solution of the nucleophile, wherein the pH of the solution of the nucleophile is between greater than or equal to 10.2 and less than or equal to 10.6.

The hydrogel forming composition may comprise the powdered crosslinking initiator (e.g., base or basic buffer) in any of a variety of suitable amounts in weight percent (wt. %) by mass based on the total weight of the powdered hydrogel forming composition. The amount of the base or basic buffer may affect the reactivity of the hydrogel forming composition, such as the gel time (described below), or other measure of the time it takes for the crosslinking agent to crosslink with the nucleophile (e.g., protein). Accordingly, in certain embodiments, it may be advantageous to select the type and/or amount of base or basic buffer in order to facilitate a crosslinking rate and/or degree enabling the hydrogel to crosslink and form prior to or upon delivery of the hydrogel forming composition to a tissue site so as to effectively seal tissue.

In certain embodiments, the hydrogel forming composition comprises the crosslinking initiator in an amount, on a powdered basis, greater than or equal to 0.1 wt. %, greater than or equal to 0.2 wt. %, greater than or equal to 0.5 wt. %, greater than or equal to 1 wt. %, greater than or equal to 1.5 wt. %, greater than or equal to 2 wt. %, greater than or equal to 2.5 wt. %, greater than or equal to 3 wt. %, greater than or equal to 4 wt. %, or greater than or equal to 5 wt. %, greater than or equal to 6 wt. %, greater than or equal to 7 wt. %, greater than or equal to 8 wt. %, or greater than or equal to 9 wt. % of the total weight of the powdered hydrogel forming composition. In certain embodiments, the hydrogel forming composition comprises the crosslinking initiator in an amount, on a powdered basis, less than or equal to 10 wt. %, less than or equal to 9 wt. %, less than or equal to 8 wt. %, less than or equal to 6 wt. %, less than or equal to 5 wt. %, less than or equal to 4 wt. %, less than or equal to 3 wt. %, less than or equal to 2 wt. %, less than or equal to 1.5 wt. %, less than or equal to 1 wt. %, less than or equal to 0.5 wt. %, or less than or equal to 0.2 wt. %, or less than or equal to 5 wt. % of the total weight of the powdered hydrogel forming composition. Combinations of the above recited ranges are also possible (e.g., the hydrogel forming composition comprises the crosslinking initiator in an amount, on a powdered basis, greater than or equal to 0.1 wt. % and less than or equal to 10 wt. % of the total weight of the powdered hydrogel forming composition or greater than or equal to 0.1 wt. % and less than or equal to 5 wt. % of the total weight of the powdered hydrogel forming composition, the hydrogel forming composition comprises the crosslinking initiator in an amount, on a powdered basis, greater than or equal to 4 wt. % and less than or equal to 8 wt. % of the total weight of the composition). Other ranges are also possible.

According to certain embodiments, the crosslinking initiator may be compartmentalized to be part of the second component. For example, in some embodiments, the crosslinking initiator may be combined with the protein (e.g., albumin) as a powder mixture. In some such embodiments, the crosslinking initiator and the protein may be lyophilized. In some alternative embodiments, the crosslinking initiator may be dissolved in a solvent (e.g., water) and used as the hydration solution to hydrate the second component (e.g., the protein).

It is possible to provide a hydrogel forming composition in which a nucleophilic polymer (e.g., a protein such as serum albumin) of the second component can react with the crosslinking agent comprising multiple electrophilic groups of the first component without requiring a separate base and/or basic buffer (e.g., included in the hydrogel forming composition or added as a separate dry powder), or with relatively little separate base and/or basic buffer present. The hydrogel forming composition may be formed, for example, by preparing a protein as a dry powder in such a way that upon exposure to an aqueous liquid (e.g., saline, phosphate-buffered saline) even in the absence of a separate powdered base and/or basic buffer, some or all of the amine groups of the protein act as the initiator in that they have been converted to free amines in sufficient quantity to initiate crosslinking to form the hydrogel. This surprising result may allow for formulations of the hydrogel forming composition with little or no need for a separate powdered basic salt of buffer salt to act as the initiator. In some embodiments, the hydrogel forming composition is free of any basic salt or buffer salt (e.g., free of any powdered basic salt or basic buffer). It should be understood that a hydrogel forming composition that is free of any powdered basic salt or buffer salt may still comprise a crosslinking initiator as the term is generally understood. For example, as described below, a protein in such a formulation may comprise unprotonated amino acid side chains, which can lend sufficient basicity to the protein to make it capable of initiating crosslinking (e.g., by elevating the pH of a resulting aqueous liquid upon hydration of the protein and by providing free amino groups for nucleophile/electrophile reactions). Such formulations may also promote increased shelf stability of the hydrogel forming composition. In some embodiments in which a protein having deprotonated amine groups is used, a relatively small amount of basic salt or basic buffer may also be present in the second component (e.g., when a molar excess of base and/or buffer salt with respect to the protein is used in preparing the second component and precipitated upon drying after the herein-described deprotonation step in forming the powdered second component). For example, in some such embodiments, the second component comprises a basic salt and/or basic buffer (e.g., powdered basic salt and/or basic buffer) in an amount less than or equal to 10 wt. %, less than or equal to 5 wt. %, less than or equal to 2 wt. %, less than or equal to 1.9 wt. %, less than or equal to 1.5 wt. %, less than or equal to 1 wt. %, less than or equal to 0.5 wt. %, less than or equal to 0.3 wt. %, less than or equal to 0.1 wt. %, less than or equal to 0.05 wt. %, less than or equal to 0.03 wt. %, less than or equal to 0.001 wt. %, or less versus the total weight of the second component on a powdered basis.

In some embodiments, the second component is free of any powdered basic salt or buffer salt comprising a carbonate anion (e.g., sodium carbonate) or bicarbonate anion (e.g., sodium bicarbonate). In some embodiments, the second component comprises a powdered basic salt or buffer salt comprising a carbonate anion (e.g., sodium carbonate) or bicarbonate anion (e.g., sodium bicarbonate) in an amount less than less than or equal to 0.1 wt. %, less than or equal to 0.05 wt. %, less than or equal to 0.03 wt. %, less than or equal to 0.001 wt. %, or less versus the total weight of the second component on a powdered basis.

In some embodiments, a protein of the second component of the hydrogel forming composition is at least partially deprotonated to form the above-mentioned free amine groups acting as an initiator. A protein may be at least partially deprotonated prior to inclusion in the hydrogel forming composition, such that the protein acts as both a crosslinking reactant component and as an initiator of the crosslinking reaction. For example, prior to inclusion in hydrogel forming composition (e.g., as part of the second component), the protein may be exposed to a base such that one or more acidic protons are removed from the protein. As one example, the protein may initially include lysine amino acid side chains that are protonated (having ammonium groups, —$NH_3^+$), and the protein may be exposed to a liquid under basic conditions. Under the basic conditions, a base (e.g., hydroxide ion) may deprotonate some or all of the protonated lysine amino acids of the protein to provide free amino groups (—$NH_2$) or even a negatively charged amide ion groups (—$NH^-$) if the base is sufficiently strong. The protein may then be provided in a solid form (e.g., as particles of a powder) in which at least some of the lysines are still present as free amino groups or amide ion groups. Upon exposure to an aqueous liquid (e.g., saline, phosphate-buffered saline), the free amino groups of the at least partially deprotonated protein may readily react with the electrophilic groups of the crosslinking agent (e.g., $PEG(SS)_2$). By contrast, preparation of dry powders of proteins that does not include deprotonating the protein in such a way results in dry powdered protein components in which a greater number of potentially nucleophilic groups (e.g., lysine side chains) are in a protonated state than in the at least partially deprotonated proteins described here.

In some embodiments, a protein of the second component of the hydrogel forming composition is in a basic state, thereby acting as a reactant and an initiator of the cross-linking reaction. In this context, a protein in a basic state is one in which fewer amino acid side chains of the protein are in a protonated state than would be observed in an equivalent protein dissolved in an unbuffered pH-neutral aqueous solution. As an illustrative example, a protein may comprise amino acid side chains having varying $pK_a$s such that in a pH-neutral, unbuffered water solution, 75% of the amino side chains are in a protonated state (e.g., lysine side chains having ammonium groups) and 25% are in an unprotonated state (lysine side chains having free amino groups). If an equivalent protein (e.g., in a hydrogel forming composition) is in a state where 10% of the amino acid groups are in a protonated state and 90% are in an unprotonated state, then that protein would be considered to be in a basic state. A protein may be in a basic state due to, for example, being at least partially deprotonated as described above. One way to compare the protonation states of proteins is to compare the "own charge" of the proteins. For example, to compare the protonation state of a protein in a basic state (e.g., in a dry powder) to an equivalent protein at neutral pH, the own charge of each can be determined as follows. To establish a measure indicative of the protonation state of the under neutral, unbuffered aqueous conditions, the protein can be dissolved in pH-neutral, unbuffered water and the "own charge" of that protein can be measured. Then, to establish a measure indicative of the protonation state of the protein in the basic state, the protein in the basic state can be dissolved in deionized water and the own charge of the protein in the basic state can be measured. A protein in a basic state will have a more negative own charge than an equivalent protein in pH-neutral conditions. The own charge of a protein is the net charge of the protein minus the charge of all bound ions, and is correlated to the number of protons associated with the protein. The own charge can be measured according to the method described in Fogh-Andersen, N., Bjerrum, P. J., & Siggaard-Andersen, O. (1993). Ionic binding, net charge, and Donnan effect of human serum albumin as a function of pH. *Clinical chemistry,* 39(1), 48-52, which is incorporated herein by reference in its entirety. Briefly, one can determine the own charge by dissolving the protein in a solution and measuring the difference between the number of total ions and number of free ions in the solution (using, for example flame-emission photometry, atomic absorption spectrophotometry, and ion titrators), and then using the charge neutrality condition to determine the own charge of the protein.

A protein (e.g., serum albumin) in a basic state may act as its own initiator to more readily undergo crosslinking with the crosslinking agent (e.g., $PEG(SS)_2$), and in some instances do so even in the absence of a separate powdered initiator, such as a powdered base and/or basic buffer.

In some embodiments, a relatively large number of lysine side chains of the protein (e.g., serum albumin) are in an unprotonated (free amine) state in the hydrogel forming composition. For example, in some embodiments, at least 25%, at least 50%, at least 75%, at least 90%, at least 95%, at least 98%, or all lysine side chains of the protein are in an unprotonated state in the hydrogel forming composition.

In some embodiments, a second component comprising a protein is selected, produced, and/or treated to act as its own initiator, and, as a screening test, when dissolved in deionized water, can produce a pH of a resulting solution that is relatively high. The protein may be able to produce a relatively high pH, for example, by being in a basic state in the hydrogel forming composition (e.g., via at least partial deprotonation). At least partial deprotonation of the protein may provide basic moieties (e.g., basic amino acid side chains) of the protein that, as a screening test, upon dissolution in deionized water, can react with protons and/or water molecules in the deionized water to produce hydroxide ions, thereby producing a relatively high pH. In contrast, a protein having a relatively high number of moieties in protonated states may produce fewer hydroxide ions in the water (and in fact may produce protons), resulting in a comparatively lower pH of the resulting solution. In some embodiments, the second component (e.g., comprising particles of protein such as serum albumin), as a screening test, when dissolved in deionized water, can produce a pH of a resulting solution of greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher. It should be understood that when considering whether a second component, when dissolved in deionized water, can produce a pH of a resulting solution in the above ranges, the amount of protein added need not be specified, so long as there exists an amount of the protein dissolvable in deionized water that can produce such a pH. That said, in some embodiments, dissolution of a relatively small amount of the second component in deionized water can produce a solution with a pH in the above ranges. For example, in some embodiments, the second component, when dissolved in deionized water to form a 25 weight by volume (w/v %) resulting solution of a protein, produces such a solution having a pH of greater than or equal to 8, greater than or equal to 8.2, greater than or equal to 8.5, greater than or equal to 9, greater than or equal to 9.2, greater than or equal to 9.5, and/or up to 10, up to 10.5, up to 11, or higher. It has been observed that when preparing a second component of a hydrogel forming composition by removing liquid (e.g., water or a biocompatible organic liquid) from a preparatory solution comprising a protein (as described in more detail below), the protonation state of the protein can be substantially conserved, such that the second component in the hydrogel forming composition, when dissolved in deionized water, produces a resulting solution having a pH that is equal to the pH of the preparatory solution, assuming identical concentrations of the second component in each solution.

The second component (e.g., comprising a powdered form of a protein) of the hydrogel forming composition can be prepared according to any of a variety of methods. Some such methods can facilitate at least partially deprotonating the protein and/or other nucleophilic polymer. In some embodiments, a preparatory solution comprising an at least partially dissolved form of a protein is provided. For example, in FIG. 10, method 300 comprises step 310 of at least partially dissolving protein (e.g., albumin) in liquid. The liquid may be water. The water may be deionized water. However, in some embodiments, the water can be part of an aqueous solution. In some embodiments, the protein is at least partially dissolved in a nonaqueous solution. The nonaqueous solution can be, for example, a biocompatible organic liquid (e.g., DMSO). In some embodiments, a resulting solution comprising the protein (e.g., serum albumin) in an amount of at least 10 w/v %, at least 20 w/v %, at least 25 w/v %, and/or up to 30 w/v %, up to 40 w/v %, or greater is produced. Combinations of these ranges are possible.

Figure 10:
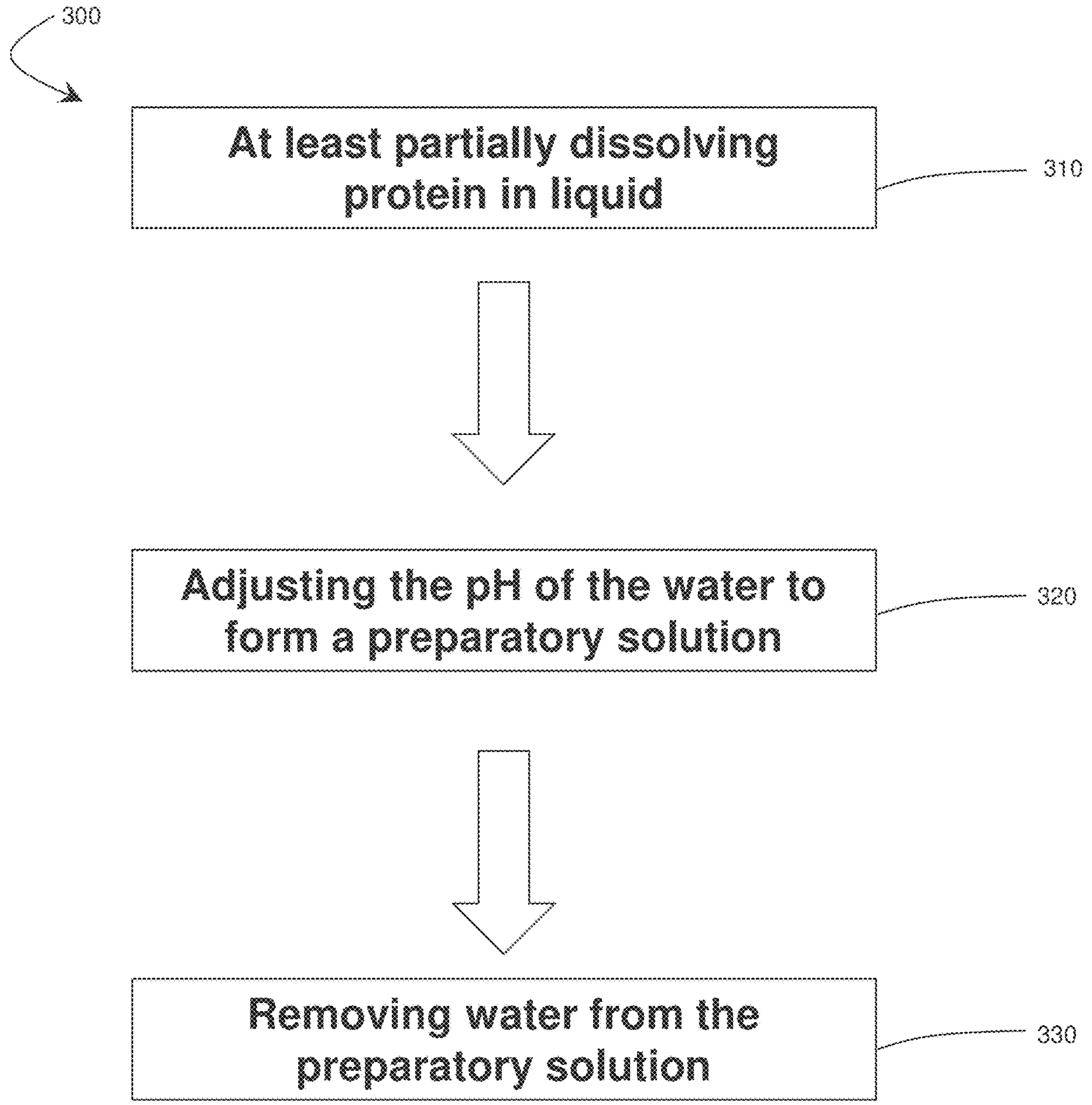
FIG. 10 shows, in accordance with certain embodiments, exemplary steps in a method for forming a protein component for a hydrogel forming composition.

The pH of the resulting solution (e.g., aqueous solution) comprising the at least partially dissolved protein may then be adjusted to form a preparatory solution, as shown in step 320 of FIG. 10. The pH may be adjusted, for example, by combining the resulting solution with a base or basic buffer (e.g., directly or via addition of a solution containing a base or basic buffer). In some embodiments, the pH of the resulting solution comprising the at least partially dissolved protein is adjusted to a pH of greater than or equal to 9.5, greater than or equal to 9.8, greater than or equal to 10, greater than or equal to 10.2, greater than or equal to 10.4, and/or up to 10.6, up to 10.8, up to 11, up to 11.2, up to 11.4, or higher. The pH may be adjusted, for example, by adding a base. For example, a hydroxide-containing basic salt such as sodium hydroxide (e.g., as a 1 N NaOH solution or a more dilute 0.1-0.2 M solution) may be added to adjust the pH. Such a pH adjustment of the preparatory solution may at least partially (or completely) deprotonate the protein. Alternative ordering of steps may be used. For example, in some embodiments, liquid (e.g., water) lacking the protein is provided at a relatively high pH (e.g., greater than or equal to 9.5, greater than or equal to 9.8, greater than or equal to 10, greater than or equal to 10.2, greater than or equal to 10.4, and/or up to 10.6, up to 10.8, up to 11, up to 11.2, up to 11.4, or higher), and the protein is at least partially dissolved in that liquid (e.g., water) having a relatively high pH, thereby producing a preparatory solution comprising a dissolved form of the protein that maintains a pH in at least one of the ranges described above.

In some embodiments where the protein is at least partially dissolved in a liquid (e.g., water) and combined with a base or basic buffer, the amount of the base or basic buffer is relatively small compared to the amount of protein in the resulting solution. As noted elsewhere in the disclosure, use of a relatively small amount of a base or basic buffer can be beneficial for any of a variety of reasons, including facilitating easier dissolution of the resulting solid form of the second component when hydrating for hydrogel formation. In some embodiments, use of relatively strong bases (e.g., sodium hydroxide) can promote an ability to use a relatively small amount of a base or basic buffer compared to the amount of protein in forming the preparatory solution. In some embodiments, during formation of the preparatory solution, a molar ratio of the amount of protein added to the preparatory solution to the amount of the base or basic buffer added to the preparatory solution is greater than or equal to 1:100, greater than or equal to 1:77, greater than or equal to 1:50, greater than or equal to 1:40, greater than or equal to 1:39, greater than or equal to 1:30, or greater. In some embodiments, during formation of the preparatory solution, a molar ratio of the amount of protein added to the preparatory solution to the amount of the base or basic buffer added to the preparatory solution is less than or equal to 1:10, less than or equal to 1:25, or less. In some embodiments, during formation of the preparatory solution, a weight ratio of the amount of protein added to the preparatory solution to the amount of the base or basic buffer added to the preparatory solution is greater than or equal to 5:1, greater than or equal to 8:1, greater than or equal to 9:1, greater than or equal to 15:1, greater than or equal to 25:1, greater than or equal to 30:1, greater than or equal to 40:1, greater than or equal to 43:1, greater than or equal to 50:1, or greater. In some embodiments, during formation of the preparatory solution, a weight ratio of the amount of protein added to the preparatory solution to the amount of the base or basic buffer added to the preparatory solution is less than or equal to 200:1, less than or equal to 100:1, less than or equal to 75:1, or less.

The base or basic buffer can be combined with the protein in liquid to form the preparatory solution in any of a variety of ways. For example, in some embodiments, a base or basic buffer may be added directly (e.g., as a solid) to liquid containing at least partially dissolved protein (e.g., to adjust the pH of the liquid in forming the preparatory solution). However, in some instances, it has been observed that combining the protein with a relatively dilute solution of the base or basic buffer can be advantageous. For example, it has been observed in the context of this disclosure that addition of relatively dilute solution of a base or basic buffer to the liquid containing the protein can reduce or prevent deleterious phenomena such as protein aggregation or gelation in the solution. Accordingly, in some embodiments, the preparatory solution is formed by combining the protein with a base or basic buffer solution (e.g., an aqueous or nonaqueous base or basic buffer solution (e.g., hydroxide) at a molar concentration of less than or equal to 0.5 M, less than or equal to 0.2 M, less than or equal to 0.15 M, less than or equal to 0.1 M, less than or equal to 0.05 M, and/or as low as 0.01 M, as low as 0.001 M, or less. It should be understood that the molar concentration of a salt (e.g., sodium hydroxide) in a solution in this disclosure refers to the number of moles of that salt dissolved in the solution per liter of the solution, and so even though the cation and anion of the salt can be separately solvated in solution, the concentration may still be reported accordingly based on the amount of initial salt added.

In some embodiments, the preparatory solution formed by combining the protein with a base or basic buffer (e.g., hydroxide) comprises the base or basic buffer at a molar concentration of less than or equal to 0.5 M, less than or equal to 0.35 M, less than or equal to 0.2 M, less than or equal to 0.15 M, less than or equal to 0.1 M, less than or equal to 0.05 M, and/or as low as 0.01 M, as low as 0.001 M, or less.

In some embodiments, the preparatory solution comprises at least one salt at a relatively high molar concentration. High concentrations of salt (e.g., sodium chloride) dissolved in the preparatory solution can, in some instances, reduce or prevent gelation of the protein. In some embodiments, the preparatory solution comprises at least one salt (e.g., sodium chloride) at a molar concentration of at least 0.25 M, at least 0.5 M. and/or up to 1 M, or greater.

In some embodiments, a surfactant is included in the preparatory solution. The surfactant (e.g., polyethylene glycol) may be added prior to addition of the protein and/or after addition of the protein during formation of the preparatory solution. However, in some embodiments, the surfactant is incorporated into the second component (or a different component of the hydrogel forming composition) at a different stage of preparation, such as following removal of liquid from the preparatory solution and formation of a solid form of the protein and, in some instances, a crosslinking initiator (e.g. a base or basic buffer). In some embodiments, the preparatory solution comprises the surfactant (e.g., polyethylene glycol) in an amount of at least 2 w/v %, at least 4 w/v %, at least 8 w/v %, at least 12 w/v %, and/or up to 20 w/v %, or higher. Combinations of these ranges are possible.

In some embodiments, liquid (e.g., water or a biocompatible organic liquid) is removed from the preparatory solution comprising the at least partially dissolved form of the protein, thereby forming a solid form of the protein, as shown in step 330 in FIG. 10. The solid form of the protein may be further processed in some embodiments to form a powdered form of the protein. For example, the solid form of the protein may be milled to form a powder, which may, in some instances undergo a particle size selection step (e.g., via sieving).

One non-limiting way to remove the liquid (e.g., water) from the preparatory solution is by lyophilizing the preparatory solution. In some embodiments, lyophilizing the preparatory solution comprises exposing the preparatory solution to an environment having a temperature of less than or equal to −10° C., less than or equal to −20° C., less than or equal to −30° C., less than or equal to −40° C., and/or as low as −50° C., or lower. In some embodiments, lyophilizing the preparatory solution comprises exposing the preparatory solution to a vacuum environment having a pressure of less than or equal to 100 Pa, less than or equal to 50 Pa, less than or equal to 40 Pa, less than or equal to 33 Pa, or lower. Combinations of these conditions are possible. For example, in some embodiments, lyophilizing the preparatory solution comprises exposing the preparatory solution to an environment having a temperature of −40° C. and a pressure of 33 Pa. Other suitable methods of removing the liquid (e.g., water) include, but are not limited to, spray drying, spray freeze drying, desiccation, etc.

In some embodiments, the hydrogel forming composition is free of powdered basic salt and/or powdered basic buffer (e.g., powdered sodium bicarbonate). In some embodiments, the hydrogel forming composition comprises a residual quantity of solid salt attributable to the above-described deprotonation/pH adjustment procedures. For example, in some embodiments, the hydrogel forming composition comprises solid salt attributable to a protein deprotonation/pH adjustment step in amount of less than or equal to 0.5 wt. %, less than or equal to 0.4 wt. %, less than or equal to 0.3 wt. % by mass and as low as 0.01 wt. % by mass of the total hydrogel forming composition. In some embodiments, the solid salt attributable to a protein deprotonation/pH adjustment step comprises a basic salt comprising hydroxide, such as sodium hydroxide. In some such embodiments, the amount of solid salt attributable to a protein deprotonation/pH adjustment step reflects (and is calculated from) a known amount of base (e.g., NaOH) added to water comprising at least partially dissolved protein to adjust the pH prior to removal of water to form the solid form of the protein. It should be understood that some (or all) of the added base (e.g., NaOH) may react with the protein and/or other nucleophile in solution (e.g., in a neutralization reaction to at least partially deprotonate a nucleophile such as a protein). Therefore, the resulting second component comprising, for example, a solid form of a protein may not contain intact, ionically-bound solid basic salt (e.g., NaOH), but may rather contain corresponding reaction products (e.g., sodium ions bound to counteranions). However, some intact basic salt (e.g., NaOH powder) may be present in instances where a molar excess of base is added with respect to acidic protons of the protein in the solution. In each case, when present in the protein-containing second component of the hydrogel-forming composition, such reaction products (e.g., sodium ions bound to counteranions) and/or intact basic salt (e.g., NaOH powder) comprise at least part of the crosslinking initiator of the second component.

Surfactants

In certain embodiments, the hydrogel forming composition comprises a surfactant. In some embodiments, the surfactant is capable of stabilizing one or more components (e.g., the first component, the second component) of the hydrogel forming composition. In certain embodiments, the surfactant is capable of increasing the rate of dissolution of the protein (e.g., albumin) in one or more solvents used to dissolve the protein. In some embodiments, the surfactant may be selected to prevent aggregation (e.g., clumping) of the protein (e.g., albumin).

Any of a variety of suitable surfactants may be utilized. In some embodiments, for example, the surfactant comprises a non-functionalized polyethylene glycol (PEG). Any of a variety of non-functionalized PEGs may be utilized. In certain embodiments, the non-functionalized PEG will be a solid at room temperature. In certain embodiments, the non-functionalized PEG will have a weight average molecular weight, for example, greater than or equal to 100 g/mol and less than or equal to 40,000 g/mol. In certain embodiments, the non-functionalized PEG is PEG 8000 (e.g., a PEG with a molecular weight of 8000 g/mol). In certain embodiments, the surfactant comprises dextran sulfate. In some embodiments, the surfactant may comprise a poloxamer, a polysorbate (e.g., TWEEN®), or encompass a purely lipophilic material such as an oil (e.g., mineral oil, vegetable oil), a siloxane, a stearate, a glycol, and/or mixtures thereof. In certain embodiments, for example, the poloxamer is Pluronic® L61. Other Pluronic® poloxamers may be also utilized.

In some embodiments, the surfactant may additionally function as an anti-foaming additive (although not all anti-foaming additives need to be surfactants). The anti-foaming additive may advantageously prevent foaming and/or air bubbles from forming when the hydrogel forming composition is hydrated to facilitate crosslinking. In some embodiments, for example, the anti-foaming additive prevents the formation of air bubbles that would otherwise be present in the hydrated hydrogel forming composition if an anti-foaming additive were not present. Such air bubbles may disrupt crosslinking and weaken the resulting hydrogel network of the tissue sealant. In certain non-limiting embodiments, a poloxamer (e.g., Pluronic® L61) is an anti-foaming additive.

According to certain embodiments, the hydrogel forming composition comprises the powdered or liquid surfactant in any of a variety of amounts in weight percent (wt. %) by mass versus the total weight of the powdered or aqueous solution of the powdered hydrogel forming composition. In some embodiments, for example, the hydrogel forming composition comprises the surfactant in an amount, on a powdered or liquid basis, greater than or equal to 0.01 wt. %, greater than or equal to 0.1 wt. %, greater than or equal to 0.5 wt. %, greater than or equal to 1 wt. %, greater than or equal to 5 wt. %, greater than or equal to 10 wt. %, or greater than or equal to 15 wt. % of the total weight of the powdered or aqueous hydrogel forming composition. In certain embodiments, the hydrogel forming composition comprises the surfactant, on a powdered or liquid basis, in an amount less than or equal to 20 wt. %, less than or equal to 15 wt. %, less than or equal to 10 wt. %, less than or equal to 5 wt. %, less than or equal to 1 wt. %, less than or equal to 0.5 wt. %, less than or equal to 0.1 wt. %, less than or equal to 0.01 wt. % of the total weight of the powdered or aqueous hydrogel forming composition. Combinations of the above recited ranges are also possible (e.g., the hydrogel forming composition comprises the surfactant in an amount, on a powdered or liquid basis, greater than or equal to 1 wt. % and less than or equal to 30 wt. % of the total weight of the powdered or aqueous hydrogel forming composition, the hydrogel forming composition comprises the surfactant in an amount, on a powdered or liquid basis, greater than or equal to 10 wt. % and less than or equal to 20 wt. % of the total weight of the powdered or aqueous solution of the powdered hydrogel forming composition). Other ranges are also possible.

In some embodiments, the surfactant may be a part of the second component. For example, in certain embodiments, the surfactant may be combined with the protein (and the crosslinking initiator, in some embodiments) as a powder mixture. In some such embodiments, the protein, crosslinking initiator, and surfactant may be lyophilized (e.g., prior to dissolution in the solvent). Without wishing to be bound by theory, in some embodiments wherein a liquid surfactant is utilized (e.g., Pluronic® L61), the liquid surfactant may hydrogen bond with one or more powder components of the second component (e.g., the protein). In some embodiments, the surfactant may be dissolved in and/or mixed with a solvent (e.g., water) that is used as a hydration solution to hydrate the second component to form a hydrated solution that is capable of crosslinking with the first component when mixed with a solution of the first component. In certain embodiments, for example, the surfactant may be dispersed and/or suspended in a solvent used to hydrate the second component.

According to certain embodiments, the hydrogel forming composition may comprise more than one surfactant (e.g., two surfactants, three surfactants, etc.), with each individual surfactant, or the cumulative amount of all the surfactants together falling in any of the weight percent ranges listed above.

In some embodiments in which the second component comprises a protein, a surfactant, and, if present, a crosslinking initiator, the second component comprises the protein in a relatively high amount. For example, in certain embodiments, the second component comprises the protein in an amount, on a powdered basis, greater than or equal to 80 wt. %, greater than or equal to 85 wt. %, greater than or equal to 86 wt. %, greater than or equal to 87 wt. %, and/or up to 90 wt. %, up to 96 wt %, or greater versus the total weight of the protein, surfactant, and crosslinking initiator when present. Combinations of these ranges are possible. Having a relatively high percentage of the second component be the protein may afford relatively efficient crosslinking in the hydrogel forming composition upon initiation of the crosslinking.

In some embodiments in which the second component comprises a protein, a surfactant, and, if present, a crosslinking initiator, the second component comprises the surfactant (e.g., polyethylene glycol) in a relatively high amount. For example, in certain embodiments, the second component comprises the surfactant in an amount, on a powdered basis, greater than or equal to 4 wt. %, greater than or equal to 8 wt. %, greater than or equal to 12 wt. %, and/or up to 15 wt. %, up to 20 wt. %, or greater versus the total weight of the protein, surfactant, and crosslinking initiator when present. Combinations of these ranges are possible. Having a relatively high percentage of the second component be the surfactant may afford relatively efficient solvation of the second component when exposed to one or more solvent (e.g., hydration solutions).

In some embodiments in which the second component comprises a protein, a surfactant, and, if present, a crosslinking initiator, the second component comprises any crosslinking initiator comprising a salt of a base or basic buffer such as sodium hydroxide and/or sodium carbonate and/or sodium bicarbonate, in a relatively low amount. For example, in certain embodiments, the second component comprises such crosslinking initiators, in an amount, on a powdered basis, less than or equal to 16 wt. %, less than or equal to 10 wt. %, less than or equal to 8 wt. %, less than or equal to greater than or equal to 5 wt. %, less than or equal to 2 wt. %, less than or equal to 1.9 wt. %, less than or equal to 1.5 wt. %, less than or equal to 1.0 wt. %, less than or equal to 0.5 wt. %, less than or equal to 0.1 wt. %, less than or equal to 0.05 wt. %, less than or equal to 0.03 wt. %, or less. In some embodiments, the second component comprises such crosslinking initiators in an amount, on a powdered basis, greater than or equal to 0.001 wt. %, greater than or equal to 0.01 wt. %, greater than or equal to 0.02 wt. %, greater than or equal to 0.05 wt. %, greater than or equal to 0.1 wt. %, greater than or equal to 0.2 wt. %, greater than or equal to 0.5 wt. %, greater than or equal to 0.6 wt. %, greater than or equal to 1 wt. %, greater than or equal to 1.5 wt. %, or greater Combinations of these ranges (e.g., greater than or equal to 0.001 wt. % and less than or equal to 16 wt. %, greater than or equal to 1.5 wt. % and less than or equal to 1.9 wt %) are possible. Having a relatively low percentage of the second component be a salt of a base or basic buffer as crosslinking initiator may be beneficial by allowing for comparatively improved dissolution properties of the components and/or improved stability of resulting hydrogels relative to compositions including higher amounts of salts of bases and/or buffers as crosslinking initiators. As noted above, use of no or a relatively small amount of buffer salts or basic salts as a crosslinking initiator may be facilitated by using relatively strong bases (e.g., sodium hydroxide) in a preparatory deprotonation step and/or as a basic salt ingredient in the second component.

Antioxidants

According to certain embodiments, the hydrogel forming composition may comprise at least one antioxidant. An antioxidant may advantageously increase the storage stability of one or more components of the hydrogel forming composition. For example, the use of one or more antioxidants may increase the shelf-life and/or storage capabilities of the hydrogel forming composition. Because the one or more antioxidants are more susceptible to oxidation than the crosslinking reagents for forming the hydrogel (e.g., due to a lower oxidation potential), the antioxidants become oxidized during storage prior to the crosslinking reagents, resulting in a hydrogel forming composition that has a longer shelf-life than a hydrogel forming composition that is otherwise comparable but does not have the one or more antioxidants.

Any of a variety of suitable antioxidants may be utilized. In certain embodiments, for example, the composition comprises butylated hydroxytoluene (BHT). In some such embodiments, BHT prevents free radical-mediated oxidation. In certain embodiments, BHT may be utilized to prevent oxidation of the difunctionalized polyalkylene oxide-based crosslinking agent. In some embodiments, the composition comprises N-acetyl-DL-tryptophan. In some such embodiments, N-acetyl-DL-tryptophan prevents oxidation of one or more amino acids and/or other residues of the protein. In certain embodiments, the antioxidant is or comprises butylated hydroxyanisole, butylated hydroxytoluene, propyl gallate d-alpha tocopheryl polyethylene glycol-1000 succinate, sodium metabisulfite, and/or mixtures thereof.

In some embodiments, the hydrogel forming composition comprises at least two antioxidants. For example, in certain embodiments, the hydrogel forming composition may comprise a first antioxidant (e.g., BHT) to prevent oxidation of the difunctionalized polyalkylene oxide-based crosslinking agent and a second antioxidant (e.g., N-acetyl-DL-tryptophan) to prevent oxidation of the protein.

In addition to preventing oxidation of one or more ingredients of the hydrogel forming composition, the one or more antioxidants can in some cases stabilize one or more ingredients of the hydrogel forming composition (e.g., the crosslinking agent, the protein, etc.) to allow sterilization with a lethal dose of radiation (e.g., electron beam or gamma radiation). In certain embodiments, for example, one or more components of the hydrogel forming composition (e.g., the first component and/or the second component) may be sterilized using electron beam radiation. In some such embodiments, the one or more components of the hydrogel may be exposed to one or more doses of electron beam radiation with a cumulative dose between greater than or equal to 25 kGy and less than or equal to 30 kGy.

According to certain embodiments, the hydrogel forming composition comprises each antioxidant (e.g., a first antioxidant, a second antioxidant) in any of a variety of suitable amounts in weight percent (wt. %) by mass versus the total weight of the powdered hydrogel forming composition. In some embodiments, for example, the hydrogel forming composition comprises each antioxidant in an amount, on a powdered basis, greater than or equal to 0.1 wt %, greater than or equal to 1 wt. %, greater than or equal to 2 wt. %, greater than or equal to 5 wt. %, greater than or equal to 10 wt. %, or greater than or equal to 15 wt. % of the total weight of the powdered hydrogel forming composition. In certain embodiments, the hydrogel forming composition comprises each antioxidant in an amount, on a powdered basis, less than or equal to 20 wt. %, less than or equal to 15 wt. %, less than or equal to 10 wt. %, less than or equal to 5 wt. %, less than or equal to 2 wt. %, less than or equal to 1 wt. %, or less than or equal to 0.1 wt. % of the total weight of the powdered hydrogel forming composition. Combinations of the above recited ranges are also possible (e.g., the hydrogel forming composition comprises each antioxidant in an amount, on a powdered basis, greater than or equal to 0.1 wt. % and less than or equal to 20 wt. % of the total weight of the powdered hydrogel forming composition, the hydrogel forming composition comprises each antioxidant in an amount, on a powdered basis, greater than or equal to 1 wt. % and less than or equal to 5 wt. % of the total weight of the powdered hydrogel forming composition). Other ranges are also possible.

According to certain embodiments, the antioxidant may be a part of the first and/or second component. In some embodiments, for example, at least one antioxidant may be combined with the crosslinking agent and/or protein as a powder mixture. In some such embodiments, the antioxidant may by lyophilized with the protein (and/or the crosslinking agent, in some cases). In certain alternative embodiments, the antioxidant may be dissolved (e.g., in a solvent such as water) that is used as the hydration solution to hydrate the first and/or second component.

Radiopaque Agents

In some embodiments, the hydrogel forming composition comprises a radiopaque agent. The use of a radiopaque agent can provide the resulting hydrogel with the ability to be spectroscopically imaged, for example, by X-ray or computed tomography (CT) imaging. Any of a variety of suitable radiopaque agents may be added. In some embodiments, the radiopaque agent comprises gold (e.g., gold nanoparticles), silver (e.g., silver nanoparticles), or iodine. In certain embodiments, the radiopaque agent is potassium chloride (KCl), barium sulfate, iohexol, or diatrizoate.

According to certain embodiments, the hydrogel forming composition comprises the radiopaque agent in any of a variety of amounts in weight percent (wt. %) by mass versus the total weight of the powdered hydrogel forming composition. In some embodiments, for example, the hydrogel forming composition comprises the radiopaque agent in an amount, on a powdered basis, greater than or equal to 0.1 wt. %, greater than or equal to 0.5 wt. %, greater than or equal to 1 wt. %, greater than or equal to 5 wt. %, greater than or equal to 10 wt. %, or greater than or equal to 15 wt. % of the total weight of the powdered hydrogel forming composition. In certain embodiments, the hydrogel forming composition comprises the radiopaque agent, on a powdered basis, in an amount less than or equal to 20 wt. %, less than or equal to 15 wt. %, less than or equal to 10 wt. %, less than or equal to 5 wt. %, less than or equal to 1 wt. %, or less than or equal to 0.5 wt. % of the total weight of the powdered hydrogel forming composition. Combinations of the above recited ranges are also possible (e.g., the hydrogel forming composition comprises the radiopaque agent in an amount, on a powdered basis, greater than or equal to 0.1 wt. % and less than or equal to 20 wt. % of the total weight of the powdered hydrogel forming composition, the hydrogel forming composition comprises the radiopaque agent in an amount, on a powdered basis, greater than or equal to 1 wt. % and less than or equal to 10 wt. % of the total weight of the powdered hydrogel forming composition). Other ranges are also possible.

Other Agents

In any of the above described embodiments, the hydrogel forming composition may comprise other active agents or ingredients for various purposes, for example any of a variety of suitable active agents, such as antimicrobials, anti-inflammatories, hemostatic agents, etc.

According to some embodiments, the hydrogel forming composition is in the form of one or more powders (e.g., during storage of the hydrogel forming composition). In certain embodiments, the one or more powders of the hydrogel forming composition may be hydrated with water or one or more aqueous solutions in order to form an aqueous solution of the hydrogel forming composition comprising the crosslinking agent, the protein, the optional surfactant(s), the optional antioxidant(s), and/or the optional crosslinking initiator(s). In certain embodiments, forming the aqueous solution form of the hydrogel forming composition comprising the crosslinking agent and the protein initiates crosslinking of the crosslinking agent and the protein, thereby forming a hydrogel tissue sealant.

As mentioned above, in certain embodiments, the hydrogel forming composition may be stored and/or provided as a multicomponent formulation where certain of the ingredients are segregated from others in different powdered or hydrated components. In some embodiments, for example, the hydrogel forming composition comprises at least a first component, a second component, a solvent able to dissolve the first component and the second component, and, optionally, a surfactant. In some such embodiments, the first component comprises the crosslinking agent and an optional antioxidant, and the second component comprises the protein. The surfactant, in certain embodiments, may be a part of the second component (e.g., a powder mixture with the protein), or may be dissolved in and/or otherwise mixed with a solvent that is used to hydrate the first and/or second components. In some embodiments, the hydrogel forming composition comprises a crosslinking initiator, which may be a part of the second component (e.g., a powder mixture with the protein), or may be dissolved in a solvent that is used to hydrate one or the components (e.g., the second component). In certain embodiments, for example, the second component is a mixture (e.g., a lyophilized powder mixture) including the protein, the crosslinking initiator, and the surfactant. The hydrogel forming composition may also comprise at least one antioxidant, in some embodiments, which may be a part of the first and/or second component, or may be dissolved in a solvent that is used to hydrate the first and/or second component. In certain embodiments, the hydrogel forming composition may also comprise a radiopaque agent, in some embodiments, which may be a part of the first and/or second component, or may be dissolved in a solvent that is used to hydrate the first and/or second component.

It may be advantageous, in certain embodiments, to separately store the first component (e.g., comprising the crosslinking agent (and optional antioxidant)) and the second component (e.g., comprising the protein (and optionally a crosslinking initiator and/or surfactant)) in order to avoid any crosslinking between the crosslinking agent and the protein during storage and/or to delay crosslinking until the hydrogel forming composition is delivered to the tissue site. In certain embodiments, at least the second component comprising the protein, the crosslinking initiator, and the surfactant may be lyophilized, or at least the protein of such component is lyophilized.

According to some embodiments, the first component may be in the form of a first powder mixture and the second component may be in the form of a second powder mixture (e.g., during storage of the first component and/or the second component). In certain embodiments, the first component and/or the second component that are powder mixtures may be separately solvated or hydrated (in the description below, "hydrated" is used for brevity, but it should be understood that for embodiments where a non-aqueous solvent is used, "solvated" should be substituted for "hydrated") with water or one or more solvents (e.g., water, biocompatible organic solvent such as DMSO) or aqueous solutions, thereby providing a first component that is in the form of a first solution (e.g., first aqueous solution) and a second component that is in the form of a second solution (e.g., second aqueous solution). It should be understood that when "water," "solvents," and "aqueous solutions" are mentioned in the alternative in this disclosure, these terms are not meant to be considered mutually exclusive. For example, hydration of a component by an aqueous solution (e.g., a saline solution, PBS) can also be considered to be hydration by water and by a "solvent" because the aqueous solution contains water acting as a solvent with respect to its solutes. In certain embodiments, it may be advantageous to dissolve the first component (e.g., the crosslinking agent) in a biocompatible organic solvent, such as DMSO, in order to extend the pot life of the hydrogel forming composition. In some embodiments, the hydrated first component and the hydrated second component may be combined in order to initiate crosslinking of the crosslinking agent and the protein, thereby forming the hydrogel tissue sealant.

As mentioned above, the hydrogel component may comprise one or more solvents able to dissolve the first component and the second component. For example, the one or more solvents may include a first solvent able to dissolve the first component and a second solvent able to dissolve the second component, or a single solvent capable of dissolving both the first component and the second component. In some embodiments, the one or more solvents of the hydrogel composition comprises an aqueous solution. In some such embodiments, the aqueous solution comprises dissolved salts. As one example, in some embodiments, the one or more solvents (e.g., the first solvent for dissolving the crosslinking agent or the second solvent for dissolving the second component comprising the protein) includes a saline solution. The saline solution may contain, for example, 0.9% w/v NaCl. As another example, in some embodiments, the one or more solvents (e.g., the second solvent for dissolving the second component comprising the protein) includes a phosphate-buffered saline (PBS). The PBS may be, for example, IX PBS, which corresponds to 137 mM NaCl, 10 mM sodium phosphate monobasic, and 2.7 mM KCl, at a pH of 7.4. It has been observed in the context of this disclosure that certain aqueous solutions, when used as part of the one or more solvents capable of dissolving the first component and the second component, can reduce cytotoxicity of the resulting hydrogel forming composition.

In certain embodiments, the first solution (e.g., that hydrates the first component comprising the crosslinking agent) may comprise the radiopaque agent and/or the first antioxidant. In some embodiments, the second solution (e.g., that hydrates the second component comprising the protein) may comprise the surfactant, the crosslinking initiator, and/or the second antioxidant.

The second component, when a protein is included as the nucleophilic polymer, may be hydrated such that the concentration of the protein in the resulting hydrated solution is any of a variety of suitable amounts. In some embodiments, for example, the concentration of the protein in the hydrated second component is greater than or equal to 10% mass by volume, greater than or equal to 15% mass by volume, greater than or equal to 20% mass by volume, greater than or equal to 25% mass by volume, or greater than or equal to 30% mass by volume. In certain embodiments, the concentration of the protein in the hydrated second component is less than or equal to 35% mass by volume, less than or equal to 30% mass by volume, less than or equal to 25% mass by volume, less than or equal to 20% mass by volume, or less than or equal to 15% mass by volume. Combinations of the above recited ranges are also possible (e.g., the concentration of the protein in the hydrated second component is greater than or equal to 10% mass by volume and less than or equal to 35% mass by volume, the concentration of the protein in the hydrated second component is greater than or equal to 20% mass by volume and less than or equal to 25% mass by volume). Other ranges are also possible.

According to certain embodiments, the lyophilized second component comprising the protein may have a relatively fast dissolution time. As used herein, the term "dissolution time" is given its ordinary meaning in the art and generally refers to the time it takes for the second component comprising the protein to completely dissolve when hydrated (or solvated) with mixing or agitation. A relatively fast dissolution time may advantageously reduce the time it takes to form the hydrogel tissue sealant. The dissolution time is calculated by starting a timer, hydrating the second component by mixing the second component and the hydration solution, and stopping the timer when the second component is completely dissolved. In some embodiments, the dissolution time of the second component at 25° C. may be greater than or equal to 10 seconds, greater than or equal to 15 seconds, greater than or equal to 20 seconds, greater than or equal to 25 seconds, greater than or equal to 30 seconds, or greater than or equal to 35 seconds. In certain embodiments, the dissolution time of the second component at 25° C. is less than or equal to 40 seconds, less than or equal to 35 seconds, less than or equal to 30 seconds, less than or equal to 25 seconds, less than or equal to 20 seconds, or less than or equal to 15 seconds. Combinations of the recited ranges are also possible (e.g., the dissolution time of the second component at 25° C. is between greater than or equal to 10 seconds and less than or equal to 40 seconds, the dissolution time of the second component at 25° C. is between greater than or equal to 20 seconds and less than or equal to 30 seconds). Other ranges are also possible.

In certain embodiments, the dissolution time of the second component may depend on the amount of protein in the second component upon hydration, i.e. its mass by volume of the solution. For example, in some embodiments, the dissolution time of the second component is directly proportional to the amount of protein in the second component. In some non-limiting embodiments, for example, a second component comprising a relatively low amount of protein (e.g., 10% mass by volume in the resulting hydration solution) will have a shorter dissolution time as compared to a second component that is otherwise equivalent but has a relatively high amount of protein (e.g., 30% mass by volume in the resulting hydration solution), assuming that the final volume is the same between the second component comprising the lower amount of protein and the second component comprising the higher amount of protein.

The solution of the lyophilized second component (e.g., comprising the protein and the crosslinking initiator) may have a relatively high pH upon dissolution. In certain embodiments, for example, the solution of the lyophilized second component, upon dissolution, has a pH greater than or equal to 9, greater than or equal to 9.5, greater than or equal to 10, or greater than or equal to 10.5. In some embodiments, the solution of the lyophilized second component, upon dissolution, has a pH less than or equal to 11, less than or equal to 10.5, less than or equal to 10, or less than or equal to 9.5. Combinations of the above recited ranges are also possible (e.g., the solution of the lyophilized second component, upon dissolution, has a pH between greater than or equal to 9 and less than or equal to 11, the solution of the lyophilized second component, upon dissolution, has a pH between greater than or equal to 10 and less than or equal to 10.5). Other ranges are also possible.

It should be understood that, when specifying a second component, when hydrated as explained herein, produces a pH of a resulting solution in the above ranges, the amount of protein added need not be specified, so long as there exists an amount of the protein that can be hydrated to produce such a pH. That said, in some embodiments, dissolution of even a relatively small amount of the second component (e.g., 10% mass by volume) can produce a solution with a pH in the above ranges. For example, in some embodiments, the second component, when hydrated to form a resulting solution of the protein, produces a solution having a pH of greater than or equal to 9, greater than or equal to 9.5, greater than or equal to 10, or greater than or equal to 10.5.

In certain embodiments, as explained herein, the first component and the second component may be dissolved in one or more solvents then combined/mixed together to form a crosslinking hydrogel forming composition comprising a solution of the first component and the second component. In some embodiments, for example, the first component is dissolved in a first solvent and the second component is dissolved in a second solvent, which are then combined to form the hydrogel forming composition solution. The hydrogel forming composition solution of the first component and the second component may have a pH that is less than or substantially similar to the pH of the solution of the lyophilized second component. In certain embodiments, for example, the crosslinking solution of the first component and the second component has a pH greater than or equal to 7, greater than or equal to 8, greater than or equal to 9, greater than or equal to 9.5, greater than or equal to 10, or greater than or equal to 10.5. In some embodiments, the crosslinking solution of the first component and the second component has a pH less than or equal to 11, less than or equal to 10.5, less than or equal to 10, or less than or equal to 9.5. Combinations of the above recited ranges are also possible (e.g., the crosslinking solution of the first component and the second component has a pH greater than or equal to 9 and less than or equal to 11, the crosslinking solution of the first component and the second component has a pH greater than or equal to 10 and less than or equal to 10.5). Other ranges are also possible.

In certain non-limiting but advantageous embodiments, the hydrogel forming composition solution of the first component and the second component is formed by combining an unbuffered solution of the first component with a solution of the second component that has a pH greater than or equal to 10 and less than or equal to 11. In certain non-limiting but advantageous embodiments, the hydrogel forming composition solution of the first component and the second component is formed by combining an unbuffered solution of the first component with a solution of the second component that has a pH greater than or equal to 10.2 and less than or equal to 10.6.

The time it takes for the hydrated hydrogel forming composition to crosslink and form a gel may determine how fast the composition can act as a tissue sealant when the hydrogel/hydrogel forming composition is delivered to a tissue site. It may be beneficial for the hydrogel forming composition to crosslink within a sufficiently short time frame to permit the applied composition to quickly seal a tissue puncture site or other wound surface when the hydrogel forming composition is applied to the tissue site. The "measured gel time" as used herein is determined by dispensing the hydrated first component and the hydrated second component to a vial containing a stir bar on a stir plate adjusted to 300 RPM and recording the initial time (To) upon dispensing the components of the composition, followed by recording the end time ($T_F$) when gelation causes the stir bar to stop spinning. The measured crosslink time is the time when the timer is stopped minus the initial time. In certain embodiments, rheometry may be used to determine the measured gel time.

The hydrogel forming composition may have any of a variety of suitable measured gel times for particular uses and application methods. In some embodiments, for example, the hydrogel forming composition may have a measured gel time of greater than or equal to 0.1 seconds, greater than or equal to 0.5 seconds, greater than or equal to 1 second, greater than or equal to 2 second, greater than or equal to 3 seconds, greater than or equal to 4 seconds, greater than or equal to 5 seconds, greater than or equal to 10 seconds, or greater than or equal to 15 seconds. In certain embodiments, the hydrogel forming composition has a measured gel time of less than or equal to 20 seconds, less than or equal to 15 seconds, less than or equal to 10 seconds, less than or equal to 5 seconds, less than or equal to 4 seconds, less than or equal to 3 seconds, less than or equal to 2 seconds, less than or equal to 1 second, or less than or equal to 0.5 seconds. Combinations of the above recited ranges are also possible (e.g., the hydrogel forming composition may have a measured gel time of greater than or equal to 0.1 seconds and less than or equal to 20 seconds, the hydrogel forming composition may have a measured crosslink time of greater than or equal to 1 second and less than or equal to 3 seconds). Other ranges are also possible.

According to certain embodiments, the measured gel time may be rendered advantageously short by adjusting the amount of the crosslinking initiator. In some embodiments, for example, sufficient crosslinking initiator is added to provide a suitable pH value, as explained herein, to initiate the crosslinking reaction between the crosslinking agent and the protein in a given surgical environment. In certain embodiments, the crosslinking initiator provides a pH value of greater than or equal to 10 (e.g., between 10-11, between 10.2-10.6, between 10.3-10.4), which facilitates a faster crosslinking reaction since the reaction is generally favored at higher pH values. In certain embodiments, the gel time is tunable, depending on the amount of the base or basic buffer in the hydrogel forming composition.

In some cases, it may be advantageous for the hydrogel forming composition to have a sufficiently long measured pot life. As used herein, the term "measured pot life" refers to the duration of time that the hydrated first and second components of the hydrogel forming composition remain usable after hydration of one or more of the powdered reactive components (e.g., the first component and/or the second component) but prior to combining the solutions of the first and second components to form the crosslinking hydrogel forming composition solution. A sufficiently long pot life, in some embodiments, may advantageously allow the hydrated first and second components of the hydrogel forming composition to remain usable after a user (e.g., a physician) has hydrated the first and second components until the user is ready to deliver the one or more components to the site of administration to form the hydrogel tissue sealant. The "measured pot life" as used herein is determined by measuring certain performance metrics, such as, for example, the gel time and/or the burst strength (both of which are explained herein in greater detail) of a crosslinked hydrogel forming composition or formed hydrogel and comparing to an equivalent hydrogel forming composition or formed hydrogel formed from freshly hydrated first and second components of the hydrogel forming composition that have not been subject to storage or delayed use after hydration. The measured pot life is the time it takes for the performance metric of the crosslinked hydrogel composition resulting from the one or more hydrated components that have been stored for a period of time to differ from the performance metric of the crosslinked hydrogel composition resulting from the one or more freshly hydrated components by a defined percentage (e.g., +/−10%) based on a clinically based minimum value for each performance metric to ensure that the hydrogel tissue sealant can safely perform its function (e.g., sealing tissue).

The hydrogel forming components of the composition may have any of a variety of suitable pot life times (defined as performance metric differing by no more than +/−10%). In some embodiments, for example, the hydrogel forming composition has a pot life of greater than or equal to 10 minutes, greater than or equal to 20 minutes, greater than or equal to 30 minutes, greater than or equal to 1 hour, greater than or equal to 2 hours, greater than or equal to 5 hours, or greater than or equal to 10 hours. In certain embodiments, the hydrogel forming composition has a pot life less than or equal to 24 hours, less than or equal to 10 hours, less than or equal to 5 hours, less than or equal to 2 hours, less than or equal to 1 hour, less than or equal to 30 minutes, or less than or equal to 20 minutes. Combinations of the above recited ranges are also possible (e.g., the hydrogel forming composition has a pot life between greater than or equal to 10 minutes and less than or equal to 24 hours, the hydrogel forming composition has a pot life greater than or equal to 1 hour and less than or equal to 2 hours). Other ranges are also possible.

According to certain non-limiting embodiments, the pot life of either or both reagent components of the hydrogel forming composition may be increased, particularly for embodiments where a component is provided in solvated form, by dissolving such component(s) in a biocompatible non-polar organic solvent, such as DMSO, to form the solvated component(s) of the hydrogel forming composition. Use of such a solvent may in certain instances substantially increase the pot life, to be, for example, greater than or equal to 1 week, greater than or equal to 1 month, greater than or equal to 6 months, greater than or equal to 1 year, or greater than or equal to 2 years.

According to some embodiments, it may be advantageous for the hydrogel forming composition to have a sufficiently long measured shelf life. As used herein, the term "measured shelf life" refers to the duration of time that one or more of the powdered components of the hydrogel forming composition remains suitably usable after storage of the one or more powdered components. A sufficiently long shelf life, in some embodiments, may advantageously allow the hydrogel forming composition to remain usable after long-term storage of the hydrogel forming composition. The "measured shelf life" as used herein is determined by measuring certain performance metrics, such as, for example, the gel time, dissolution time, and/or the burst strength (which are explained herein in greater detail) of a crosslinking hydrogel forming composition solution and/or a crosslinked hydrogel composition formed therefrom prepared that has been subject to a storage period as compared to the corresponding measured metrics resulting from such one or more powdered components of the hydrogel forming composition (e.g., the first component and/or the second component) that have not been subject to storage prior to hydration. The measured shelf life is the time it takes for the performance metric of the crosslinked hydrogel composition resulting from the one or more powdered components that have been subject to storage for a period of time prior to hydration to differ from the same metric measured for fresh ingredients by a specified percentage (e.g., +/−10%) based on a clinically based minimum value for each performance metric to ensure that the hydrogel tissue sealant can safely perform its function (e.g., sealing tissue).

The first and second components of the hydrogel forming composition may have any of a variety of suitable shelf life times. In some embodiments, for example, the hydrogel forming composition has a shelf life (defined as resulting is a difference compared to fresh ingredients of +/−10%) of greater than or equal to 1 week, greater than or equal to 1 month, greater than or equal to 6 months, greater than or equal to 1 year, greater than or equal to 2 years, greater than or equal to 3 years, or greater than or equal to 4 years. In certain embodiments, the hydrogel forming composition has a shelf life less than or equal to 5 years, less than or equal to 4 years, less than or equal to 3 years, less than or equal to 2 years, less than or equal to 1 year, less than or equal to 6 months, or less than or equal to 1 month. Combinations of the above recited ranges are also possible (e.g., the hydrogel forming composition has a shelf life between greater than or equal to 1 week and less than or equal to 5 years, the hydrogel forming composition has a shelf life greater than or equal to 1 year and less than or equal to 2 years). Other ranges are also possible.

It should be understood that any of a variety of the hydrogel forming compositions described in this disclosure can, in some instances, have one or more of the properties described throughout, such as certain gel times, dissolution times, pot life, shelf life. It should also be understood that while some such compositions may comprise a surfactant in the manner described, such a surfactant is not necessarily required in all embodiments.

Methods of forming a hydrogel tissue sealant are provided. In some embodiments, the method comprises forming a crosslinking solution comprising at least a crosslinking agent and a nucleophilic biodegradable polymer (e.g., a protein), wherein forming the crosslinking solution initiates crosslinking of the crosslinking agent and the nucleophilic biodegradable polymer (e.g., a protein), thereby forming the hydrogel tissue sealant. In certain embodiments, as explained herein, the crosslinking solution comprises a crosslinking initiator, a surfactant, and/or an antioxidant.

According to certain embodiments, the method of forming the hydrogel tissue sealant comprises dissolving a first powdered component comprising a crosslinking agent (e.g., an electrophilic biodegradable polymer) and a second powdered component comprising a nucleophilic biodegradable polymer (e.g., a protein) in one or more solvents. In some embodiments, for example, the first component is dissolved in a first solvent (e.g., water or an aqueous solution) and the second component is dissolved in a second solvent (e.g., water or an aqueous solution). In some such embodiments, the dissolved first component and the dissolved second component are combined to form a crosslinking hydrogel forming composition in the form of a solution comprising the crosslinking agent and the protein, thereby initiating crosslinking of the crosslinking agent and the nucleophilic biodegradable polymer (e.g., a protein) to from the hydrogel tissue sealant.

In certain embodiments, the method of forming a hydrogel tissue sealant comprises hydrating a first powdered component including a crosslinking agent and at least one antioxidant, hydrating a second powdered component including a protein, a crosslinking initiator, and a surfactant, and combining the hydrated first component and the hydrated second component to initiate crosslinking of the crosslinking agent and the protein. FIG. 1, shows steps in such an exemplary method for forming a hydrogel tissue sealant. Method 150, in step 152 comprises hydrating a first powdered component, comprising, for example, a crosslinking agent. In some embodiments, the first powdered component optionally comprises an antioxidant. In certain embodiments, the first powdered component is hydrated with a first solvent comprising water or a first aqueous solution. The first solvent may include, in some embodiments, a radiopaque agent. Step 154 comprises hydrating a second powdered component comprising, for example, a protein. In certain embodiments, the second powdered component comprises a crosslinking initiator and/or a surfactant. In some embodiments, the second powdered component is hydrated with a second solvent comprising water or a second aqueous solution. In certain embodiments, the second solvent comprises an anti-foaming agent. According to certain embodiments, step 152 and step 154 may occur simultaneously (but in separate containers). Step 156 comprises combining the hydrated first component and the hydrated second component to initiate crosslinking of the crosslinking agent and the protein to form the hydrogel tissue sealant.

Methods are also disclosed herein related to sealing tissue with the formed hydrogel compositions. In some embodiments, for example, such a method comprises delivering the hydrogel forming composition comprising the first component and the second component to a tissue site, or delivering a partially or fully crosslinked hydrogel composition to the tissue site, wherein the hydrogel composition comprises the reaction product of the above described first component and second component reagents.

The hydrogel composition may be delivered to the tissue site in any of a variety of suitable ways. In some embodiments, the first component of the hydrogel forming composition and the second component of the hydrogel forming composition may be at least partially combined to initiate crosslinking prior to delivering the hydrogel composition to the tissue site. In certain embodiments, the first component of the hydrogel forming composition and the second component of the hydrogel forming composition are fully combined prior to delivering the hydrogel composition to the tissue site. According to certain embodiments, the hydrated first component of the hydrogel forming composition and the hydrated second component of the hydrogel forming composition may crosslink as the hydrogel composition is being delivered to the tissue site. In some embodiments, for example, the hydrogel tissue sealant is at least partially formed prior to or upon delivery to the tissue site. In certain embodiments, the tissue site is a pleural site, such as the parietal pleura and/or the visceral pleura.

In certain embodiments, the hydrogel forming composition may be delivered to the tissue site using one or more syringes, sprayers, or other applicators. In certain embodiments, for example, the applicator that can be used to deliver the hydrogel forming compositions is described in U.S. Patent Application Ser. No. 62/822,490, titled "LUNG BIOPSY FLOWABLE SEALANT DELIVERY SYSTEM," or PCT/US2020/023772, titled "SEALANT DELIVERY APPARATUS, AND SYSTEM AND METHOD FOR PREPARING SAME, FOR USE IN A LUNG PROCEDURE," both of which are incorporated herein by reference in their entireties. The following application, filed on even date herewith, is also incorporated by reference in its entirety: International Application No. PCT/US21/23171, filed on Mar. 19, 2021, titled "MULTI-COMPONENT SEALANT DELIVERY SYSTEMS INCORPORATING QUARTER TURN CONNECTORS." Further details regarding the hydrogel forming composition delivery device are described below.

According to some embodiments, the hydrogel tissue sealant can be formulated so that it adheres to the tissue site. In certain embodiments, the adherence of the hydrogel tissue sealant at the tissue site may be determined by a liquid burst pressure strength model based on ASTM F2392-04 (the Standard Test Method for Burst Strength of Surgical Sealants). According to some embodiments, the test is designed to determine the pressure needed to rupture the sealant patch covering a simulated liquid leak and indirectly measure the adhesion property of the sealant to simulated tissue. In certain embodiments, the hydrogel tissue sealant may have any of a variety of suitable burst pressure strengths (e.g., liquid burst pressure strengths). For example, in some embodiments, the burst pressure strength of the hydrogel tissue sealant measured by such test is greater than or equal to 10 mm Hg, greater than or equal to 50 mm Hg, greater than or equal to 100 mm Hg, greater than or equal to 150 mm Hg, greater than or equal to 200 mm Hg, or greater than or equal to 250 mm Hg. In certain embodiments, the burst pressure strength of the hydrogel tissue sealant measured by such test is less than or equal to 300 mm Hg, less than or equal to 250 mm Hg, less than or equal to 200 mm Hg, less than or equal to 150 mm Hg, less than or equal to 100 mm Hg, less than or equal to 50 mm Hg. Combinations of these ranges are also possible (e.g., the burst pressure strength of the hydrogel tissue sealant is greater than or equal to 10 mm Hg and less than or equal to 300 mm Hg, the burst pressure strength of the hydrogel tissue sealant is greater than or equal 100 mm Hg and less than or equal to 150 mm Hg). Other ranges are also possible.

In some embodiments, the crosslinked hydrogel tissue sealant may swell (e.g., with water) after delivery to the tissue site. In some embodiments, advantageously, the hydrogel tissue sealant may have a relatively high swelling rate and/or extent (characterized by mass gain after a defined swelling period). A hydrogel tissue sealant with a relatively high swelling rate may be advantageous, as the hydrogel tissue sealant may swell and conform to the tissue delivery site to improve sealing properties. In certain embodiments, and as explained below in greater detail, the hydrogel composition may be delivered to the tissue site via a coaxial cannula. In certain embodiments the coaxial cannula becomes surrounded by the hydrogel composition during and/or after delivery of the hydrogel composition in order to perform a biopsy procedure (e.g., a lung biopsy). The coaxial cannula may, in some embodiments, be removed through the bulk of the hydrogel after the biopsy procedure, resulting in a puncture, void, or hole in the hydrogel tissue sealant. In some such embodiments, the hydrogel tissue sealant may swell (e.g., with water) after removal of the coaxial cannula, therefore substantially closing and/or filling the puncture, void, and/or hole caused by the coaxial cannula. The swelling rate of the hydrogel tissue sealant may be determined by forming the crosslinked hydrogel sealant as explained herein, recording the weight of the hydrogel composition, incubating the hydrogel composition in a phosphate-buffered saline (PBS) solution at 37° C., removing the hydrogel composition from the PBS solution after two hours, and recording the weight of the hydrogel composition, wherein the percent is calculated by the percent weight gain.

According to certain embodiments, the hydrogel tissue sealant has a swelling mass gain greater than or equal to 30%, greater than or equal to 35%, greater than or equal to 40%, greater than or equal to 45%, greater than or equal to 50%, greater than or equal to 55%, greater than or equal to 60%, or greater than or equal to 65%. In some embodiments, the hydrogel tissue sealant has a swelling mass gain less than or equal to 70%, less than or equal to 65%, less than or equal to 60%, less than or equal to 55%, less than or equal to 50%, less than or equal to 45%, less than or equal to 40%, or less than or equal to 35%. Combinations of the above recited ranges are also possible (e.g., the hydrogel tissue sealant has a swelling mass gain between greater than or equal to 30% and less than or equal to 70%, the hydrogel tissue sealant has a swelling rate between greater than or equal to 40% and less than or equal to 50%). Other ranges are also possible.

According to certain embodiments, the hydrogel tissue sealant may be utilized as a pleural lung sealant to seal off air and/or fluid from entering the pleural space. In some embodiments, the hydrogel tissue sealant may be utilized to seal the pleura together.

The hydrogel tissue sealant may degrade in the subject over time. In certain embodiments, the degradation time of the hydrogel may be determined by a degradation model based on ASTM F1635 (the Standard Test Method for in Vitro Degradation). In some embodiments, the test is designed to determine the degradation rate (that is, the mass loss rate) and change in material or structural properties, or both, of materials used in surgical implants. The hydrogel tissue sealant may have any of a variety of suitable degradation times. In some embodiments, for example, the hydrogel tissue sealant has a degradation time greater than or equal to 1 day, greater than or equal to 5 days, greater than or equal to 7 days, greater than or equal to 10 days, or greater than or equal to 15 days. In certain embodiments, the hydrogel tissue sealant has a degradation time less than or equal to 20 days, less than or equal to 15 days, less than or equal to 10 days, less than or equal to 7 days, or less than or equal to 5 days. Combinations of the above recited ranges are also possible (e.g., the hydrogel tissue sealant has a degradation time between greater than or equal to 1 day and less than or equal to 20 days, the hydrogel tissue sealant has a degradation time between greater than or equal to 10 days and less than or equal to 15 days). Other ranges are also possible.

Figure 2A:
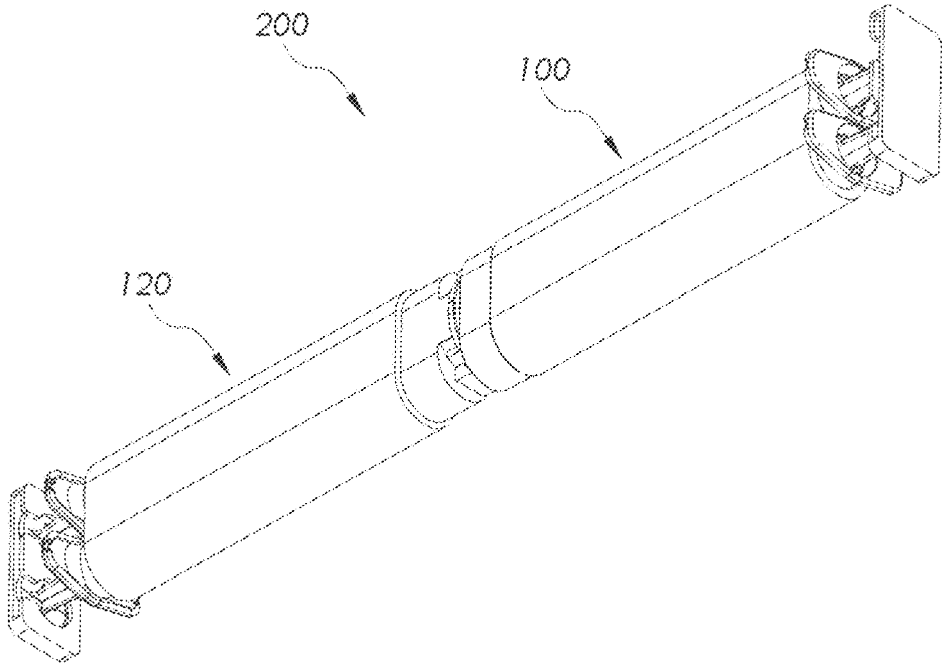
FIG. 2A shows, in accordance with certain embodiments, a schematic diagram of a syringe device that is configured for storing and/or mixing one or more components of the hydrogel forming composition.
Figure 2B:
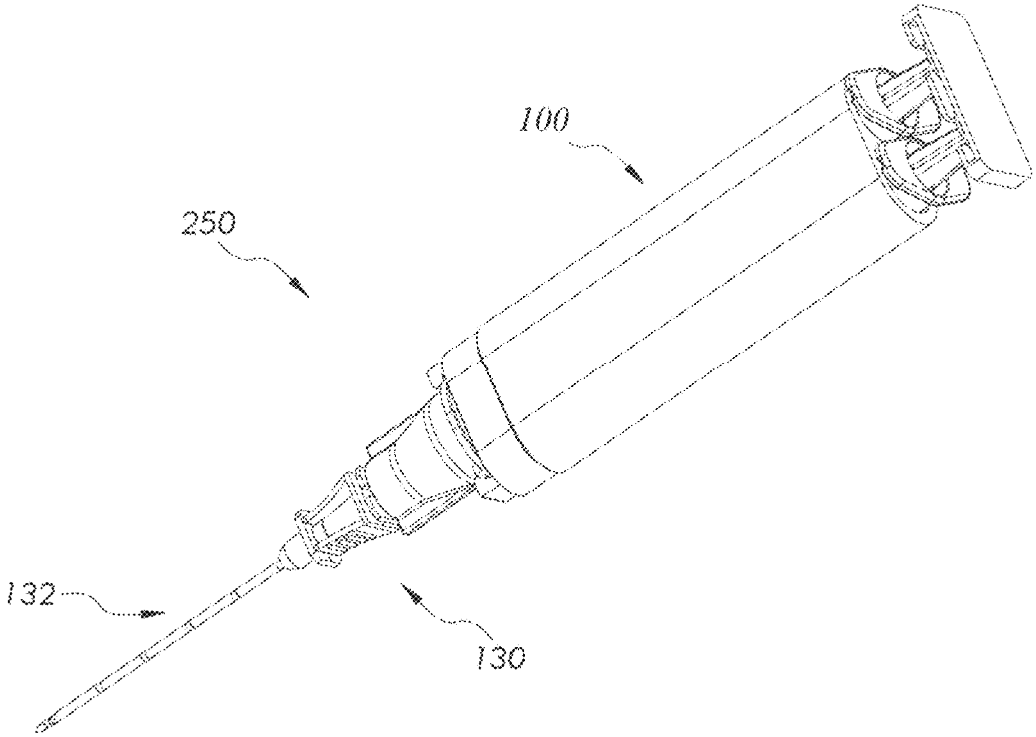
FIG. 2B shows, in accordance with certain embodiments, a schematic diagram of a syringe device that is configured for delivering a hydrogel forming composition to a tissue site.
Figure 3A:
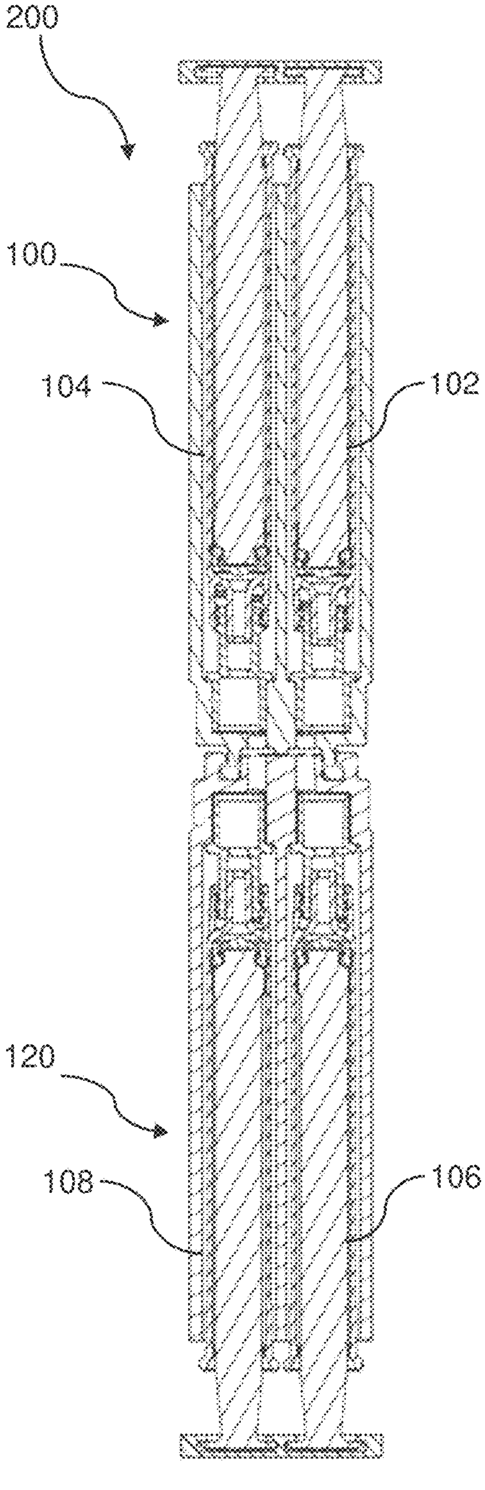
FIG. 3A shows, in accordance with certain embodiments, a cross-sectional schematic diagram of the syringe device shown in FIG. 2A.
Figure 3B:
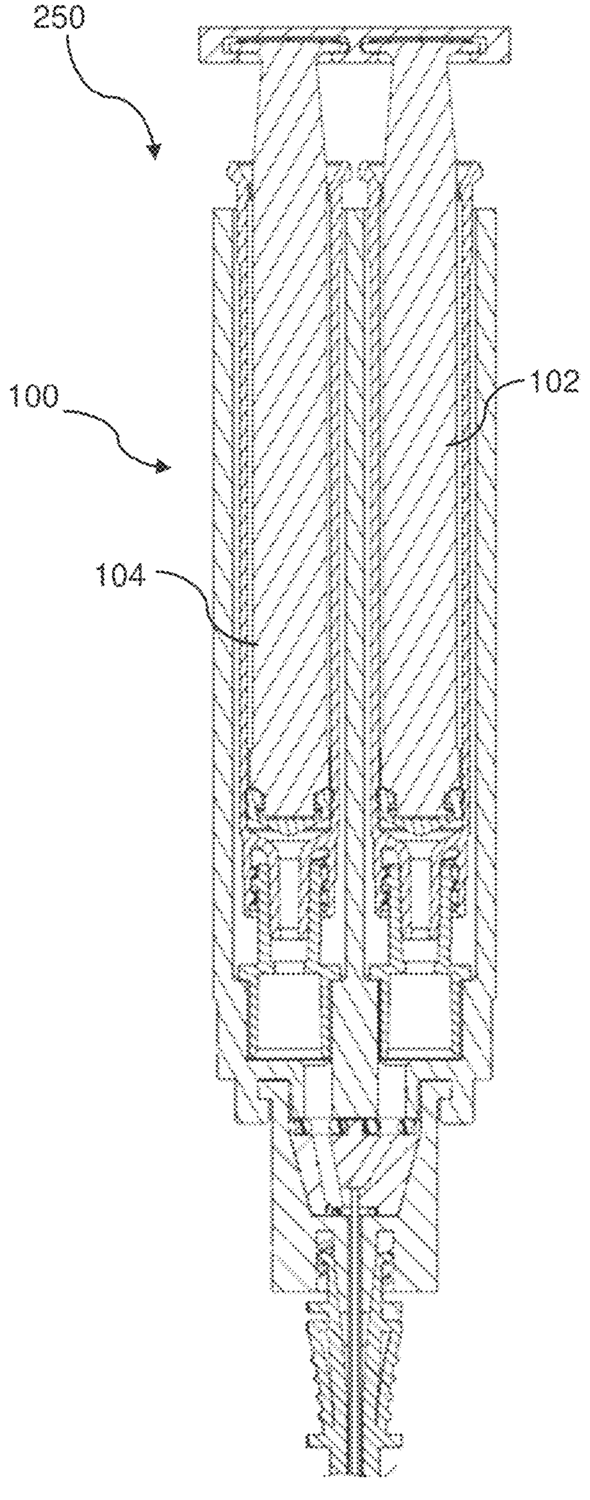
FIG. 3B shows, in accordance with certain embodiments, a cross-sectional schematic diagram of the syringe device shown in FIG. 2B.

According to certain embodiments, a kit is provided. The kit may comprise one or more devices, such as containers or syringes comprising containers (e.g. barrels of the syringes) that are capable of storing one or more components of the hydrogel forming composition, mixing one or more components of the hydrogel forming composition, and/or delivering the hydrogel forming composition (or one or more components thereof) to a tissue site. For example, FIG. 2A shows, according to certain embodiments, a schematic diagram of a dual-syringe, 4 compartment/container device 200 that is capable of storing and/or mixing one or more components of the hydrogel forming composition with one or more solvents, and FIG. 3A shows a cross-section thereof. FIG. 2B shows, according to some embodiments, a schematic diagram of a the device of FIG. 2A, where the second syringe component containing the hydrated/dissolved first and second components of the hydrogel forming composition is coupled with a coaxial cannula to be capable of delivering the hydrogel forming composition to a tissue site, and FIG. 3B shows a cross-section thereof.

The kit may comprise any of the above described first components contained within a first container, which may, as illustrated in FIGS. 2A-3B be conveniently a barrel of a syringe device. Referring to FIG. 3A, for example, syringe device 200 (e.g., with two interconnected syringe components of the device configured for mixing the stored components with one or more solvents) can comprise the first component comprising the crosslinking agent contained within first barrel/container 102, e.g. during storage. In certain embodiments, the first component may further comprise an antioxidant (e.g., BHT), a surfactant, and/or a radiopaque agent. The first component may be in the form of a first dry powder.

The kit may further comprise a second container containing any of the second components described above. Referring to FIG. 3A, for example, syringe device 200 can contain the second component within second barrel/container 104. e.g. during storage. In some embodiments, the second component may include a protein that is capable of crosslinking with the crosslinking agent. The second component may further include a crosslinking initiator that initiates crosslinking of the crosslinking agent with the protein, and/or a surfactant (e.g., PEG 8000). In some embodiments, the second component may further comprise a radiopaque agent. The second component may be in the form of a second dry powder.

In some embodiments, the kit further comprises a third, e.g., solvent, component contained within a third container. Referring, for example, to FIG. 3A, device 200 can contain such third component within third barrel/container 106. According to certain embodiments, the third component comprises a first solvent (e.g., water, DMSO) or solution (e.g., aqueous solution) for dissolving and/or hydrating the first powdered component. In some embodiments, the first solvent or solution comprises an antioxidant (e.g., BHT), a radiopaque agent (e.g., KCl), and/or a surfactant.

In certain embodiments, the kit further comprises a fourth, e.g., solvent, component contained within a fourth container. Referring, for example, to FIG. 3A, device 200 can contain such fourth component within fourth barrel container 108. According to some embodiments, the fourth compartment comprises a second solvent (e.g., water, DMSO) or solution (e.g., aqueous solution) for dissolving and/or hydrating the second powder component. In certain embodiments, the second solvent or solution comprises a crosslinking initiator (e.g., a base or basic buffer, such as sodium carbonate). In some embodiments, the second solvent or solution comprises an antioxidant (e.g., N-acetyl-DL-tryptophan), a radiopaque agent, or a surfactant (e.g., Pluronic® L61).

According to some embodiments, and as illustrated, one or more of the first, second, third, and fourth containers are compartments (barrels) of a syringe or applicator. Referring, for example, to FIGS. 2A and 3A, first barrel/container 102 and second barrel/container 104 may be double barrels of first a first syringe 100 (e.g., also used in the disclosed embodiment as the applicator syringe-See FIG. 2B), while third barrel/container 106 and fourth barrel/container 108 are double barrels of a second syringe 120 (e.g., containing mixing or hydration solvents).

According to certain embodiments, the kit for forming a hydrogel tissue sealant comprises one or more syringes collectively providing at least three separate containers. In some embodiments, for example, a kit comprises a first container that contains a first component (e.g., an electrophilic biodegradable polymer) in powder form (e.g., first container 102 in first syringe 100), a second container that contains a second component (e.g., a nucleophilic biodegradable polymer) in powder form (e.g., second container 104 in first syringe 100), and at least a third container that contains one or more solvents (e.g., third container 106 and fourth container 108 in second syringe 120).

The kit may comprise one or more syringes (e.g., one syringe, two syringes, three syringes, four syringes). The one or more syringes may have any of a variety of suitable configurations. In certain embodiments, for example, the kit comprises two syringes (e.g., first syringe 100 and second syringe 120). Each syringe of the one or more syringes may, in certain embodiments, be a double-barrel syringe. First syringe 100 (e.g., applicator syringe) may, in some embodiments, comprise first container 102 comprising the first component in powder form and second container 104 comprising the second component in powder form. According to certain embodiments, second syringe 120 (e.g., mixing or hydration syringe) comprises third container 106 comprising a first solvent able to dissolve the first component, and fourth container 108 comprising a second solvent able to dissolve the second component.

In some embodiments, the one or more syringes (e.g., first syringe 100 and second syringe 120) are configured such that first container 102 and second container 104 are able to be placed in fluid communication with at least third container 106 comprising the one or more solvents. Configuring the kit in this way facilitates the mixing of the first component with the one or more solvents to form a solution of the first component, and facilitates mixing of the second component with the one or more solvents to form a solution of the second component. For example, in certain embodiments, first syringe 100 (e.g., applicator syringe) and second syringe 120 (e.g., mixing or hydration syringe) are configured to be fluidically connectable to each other such that first container 102 and second container 104 are able to be placed in separate fluid communication with third container 106 and fourth container 108, respectively, to facilitate mixing of the first component with the first solvent to form a solution of the first component in first container 102, and to facilitate mixing of the second component with the second solvent able to form a solution of the second component in second container 104.

The kit may comprise one or more devices that are capable of delivering the hydrogel forming composition (or one or more components thereof) to a tissue site. For example, FIG. 2B shows, according to some embodiments, a schematic diagram of a device that is capable of delivering the hydrogel forming composition to a tissue site, and FIG. 3B shows a cross-section thereof. As shown in FIG. 2B, device 250 (e.g., delivery device) comprises first syringe 100 and a needle assembly. The needle assembly comprises coaxial cannula 130 and needle 132, in some embodiments. In some embodiments, first syringe 100 is configured to mix and contain the dissolved first component (e.g., the solution of the first component) and the dissolved second component (e.g., the solution of the second component) to form a crosslinking solution of the first component and the second component able to form the hydrogel tissue sealant upon delivery to the tissue site via the needle assembly.

Figure 4:
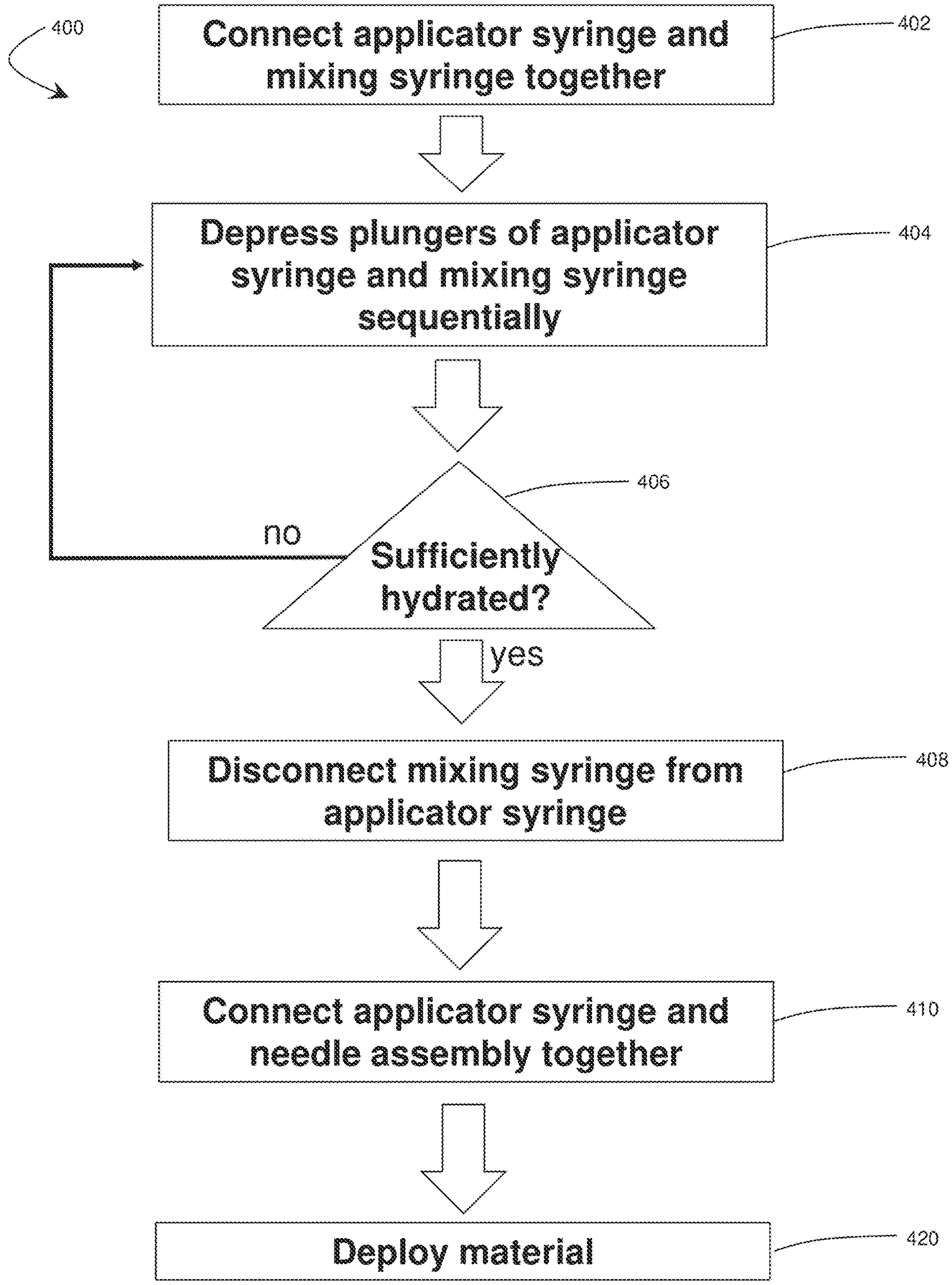
FIG. 4 shows, in accordance with certain embodiments, steps in an exemplary method for hydrating and delivering a hydrogel forming composition.

FIG. 4 shows, in accordance with certain embodiments, a summary of the steps in an exemplary method for hydrating and delivering a hydrogel forming composition using the device depicted in FIGS. 2A-3B. Method 400 of hydrating and delivering a hydrogel forming composition comprises, in some embodiments, step 402 comprising mechanically and fluidically interconnecting an applicator syringe (e.g., first syringe 100 in FIGS. 2A and 3A) and a mixing syringe (e.g., second syringe 120 in FIGS. 2A and 3A). In some such embodiments, the applicator syringe (e.g., first syringe 100 in FIGS. 2A and 3A) comprises a first component contained with a first container (e.g., first container 102 in FIGS. 2A and 3A) and a second component contained within a second container (e.g., second container 104 in FIGS. 2A and 3A), the mixing syringe (e.g., second syringe 120 in FIGS. 2A and 3A) comprises a third component contained with a third container (e.g., third container 106 in FIGS. 2A and 3A) and a fourth component contained within a fourth container (e.g., fourth container 108 in FIGS. 2A and 3A).

In certain embodiments, method 400 comprises step 404 comprising sequentially depressing the plungers of the applicator syringe (e.g., first syringe 100 in FIGS. 2A and 3A) and the mixing syringe (e.g., second syringe 120 in FIGS. 2A and 3A) to hydrate the first component contained within the first container (e.g., first container 102 in FIGS. 2A and 3A) and the second component contained within the second container (e.g., second container 104 in FIGS. 2A and 3A). Step 406 of method 400 comprises evaluating whether the first component and/or the second component are fully hydrated (e.g., completely dissolved). If the first component and/or the second component are not fully hydrated, then step 404 is repeated. If the first component and the second component are fully hydrated, then the user can proceed to step 408.

According to some embodiments, step 408 of method 400 comprises disconnecting the mixing syringe (e.g., second syringe 120 in FIGS. 2A and 3A) from the applicator syringe (e.g., first syringe 100 in FIGS. 2A and 3A), when the hydrated first component and the hydrated second component are contained in the applicator syringe. Step 410 comprises connecting a needle assembly (e.g., coaxial cannula 130 and needle 132 in FIG. 2B) to the applicator syringe (e.g., first syringe 100 in FIGS. 2B and 3B).

According to some embodiments, method 400 comprises step 420 comprising deploying the material (e.g., the solution of the first component and the solution of the second component) from the applicator syringe (e.g., first syringe 100 in FIGS. 2B and 3B) to the tissue site. In certain embodiments, deploying the material comprises mixing the solution of the first component and the solution of the second component to form a crosslinking solution of the first component and the second component as the material is being delivered to the tissue site (e.g., at one or more mixing points within the needle assembly, proximal to the needle assembly and/or at the distal tip of the needle assembly).

Figure 8A:
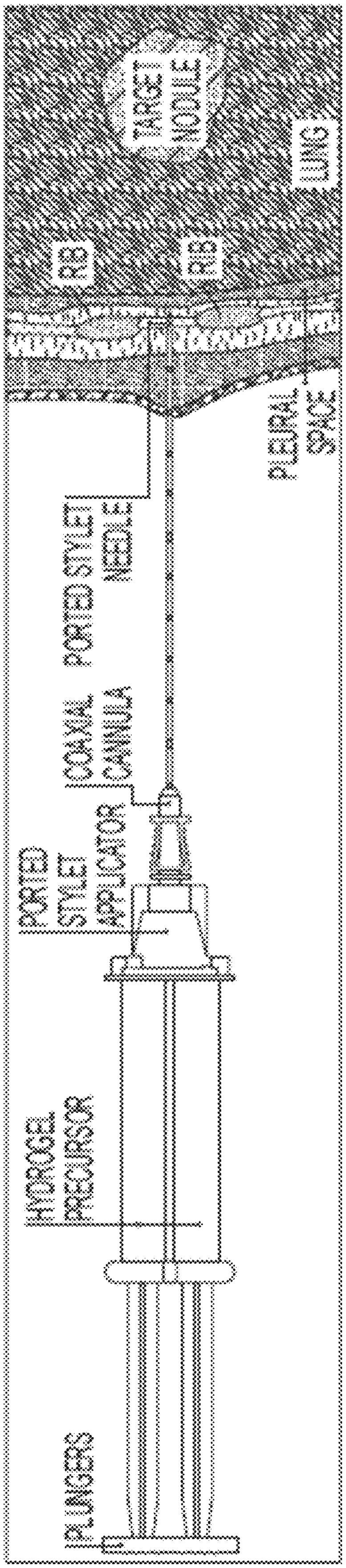
FIG. 8A shows, in accordance with certain embodiments, a schematic diagram of the syringe device depicted in FIG. 2B having its coaxial cannula inserted into the pleural space of a subject being treated prior to deployment of the hydrogel forming composition contained within the syringe.
Figure 8B:
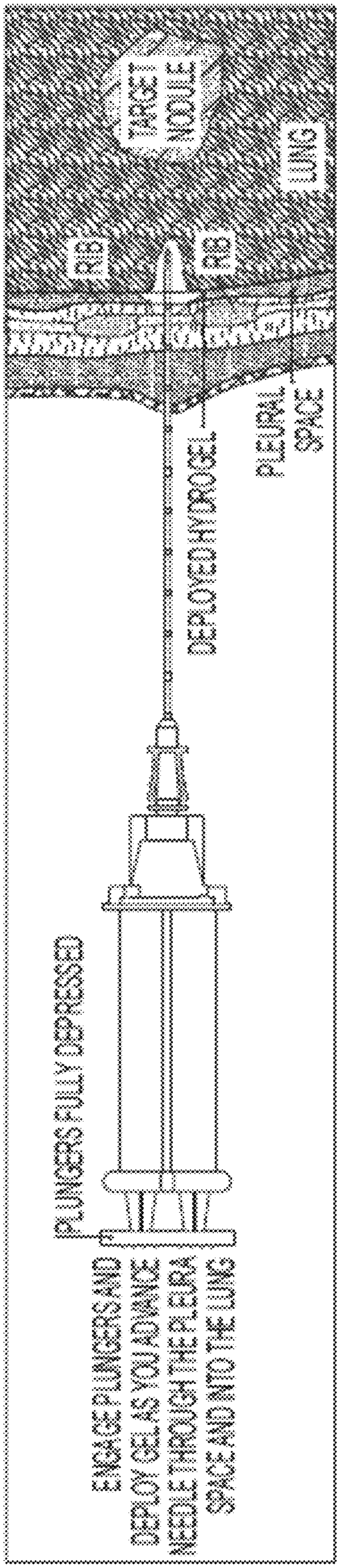
FIG. 8B shows, in accordance with certain embodiments, a schematic diagram of the syringe device of FIG. 8A with the plunger depressed for deploying the hydrogel forming composition to deliver and form the hydrogel lung sealant in the pleural space of the subject being treated.

According to certain embodiments, a needle assembly comprising a coaxial cannula is used to deliver the hydrogel composition and to perform the biopsy procedure (e.g., the lung biopsy). In some embodiments, for example, device 250 (e.g., delivery device) used to insert the coaxial cannula into the pleural space of a subject such that the hydrogel forming composition can be deployed at the tissue site. See, for example, FIG. 8A, which shows, in accordance with certain embodiments, a schematic diagram of a hydrogel delivery device having a coaxial cannula inserted into the pleural space of a subject. The hydrated hydrogel forming composition is deployed to the tissue site. See, for example, FIG. 8B, which shows, in accordance with certain embodiments, a schematic diagram of the hydrogel delivery device deploying the hydrogel forming composition via the coaxial cannula to provide a hydrogel tissue sealant at the tissue site. In some embodiments, the hydrogel forming composition is deployed during, or subsequent to the user advancing the cannula through the tissue site.

Figure 8C:
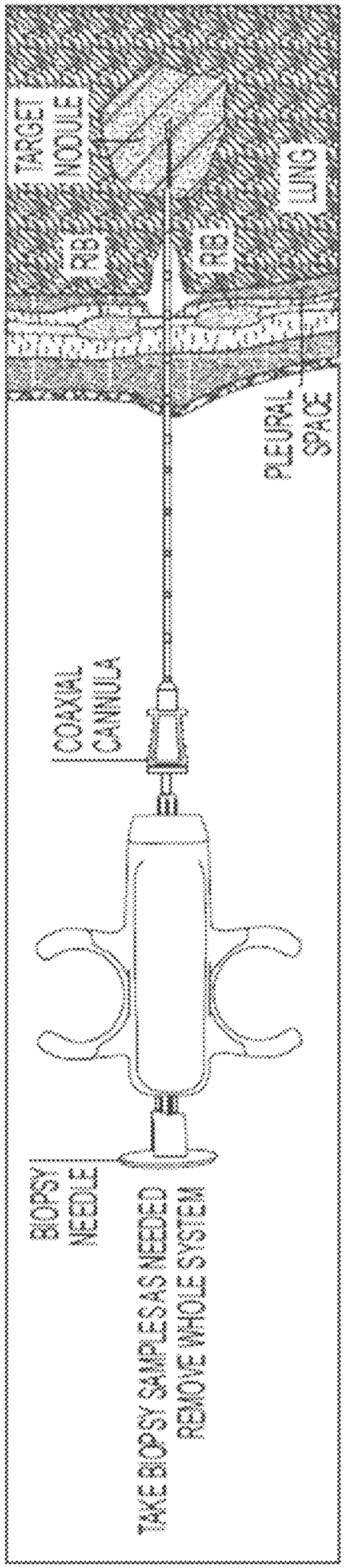
FIG. 8C shows, in accordance with certain embodiments, a schematic diagram of a biopsy needle inserted through the coaxial cannula of the syringe device of FIG. 8B.

Following delivery of the hydrogel composition, a biopsy is performed, in some embodiments. For example, according to certain embodiments, syringe component 100 of device 250 is removed from the needle assembly comprising the coaxial cannula, and a biopsy device comprising a standard biopsy needle is inserted through the coaxial cannula. The biopsy (e.g., lung biopsy) procedure is then performed. See, for example FIG. 8C, which shows, in accordance with certain embodiments, a schematic diagram of a biopsy needle inserted through the coaxial cannula to perform a biopsy procedure.

In certain embodiments, after deploying the hydrogel composition at the tissue site to provide the hydrogel tissue sealant and performing the biopsy procedure, the biopsy device and the needle assembly comprising the coaxial cannula are removed from the administration site. According to some embodiments, the hydrogel tissue sealant may swell (e.g., with water), as described herein, sealing any punctures, voids, and/or holes in the hydrogel tissue sealant caused by removal of the needle assembly.

During storage, to prevent increases in moisture or oxygen uptake by the powdered ingredients, one or more of containers/syringes containing one or more of the powdered components (particularly the powdered first component (e.g., comprising the crosslinking agent)) may be placed in a sealed pouch (e.g., a sealed foil pouch), optionally flushed with and under an atmosphere of an inert gas such as nitrogen, and further optionally containing a desiccant material within the pouch (e.g., a desiccant or molecular sieve material, such as a desiccant packet containing either PharmaKeep® (Mitsubishi Gas Chemical America, Inc.) or 4A molecular sieves (Multisorb Filtration Group).

International Patent Application Ser. No. PCT/US2021/023359, filed on Mar. 19, 2021 and entitled "Reactive Hydrogel Forming Formulations and Related Methods" is incorporated herein by reference in its entirety for all purposes. U.S. Provisional Patent Application No. 63/247,039, filed Sep. 22, 2021, and entitled "Reactive Hydrogel Forming Formulations and Related Methods. Including Methods of Preparation" and U.S. Provisional Patent Application No. 62/992,881, filed Mar. 20, 2020, and entitled "Reactive Hydrogel Forming Formulations and Related Methods" are each incorporated herein by reference in its entirety for all purposes.

Example 1

Figure 5A:
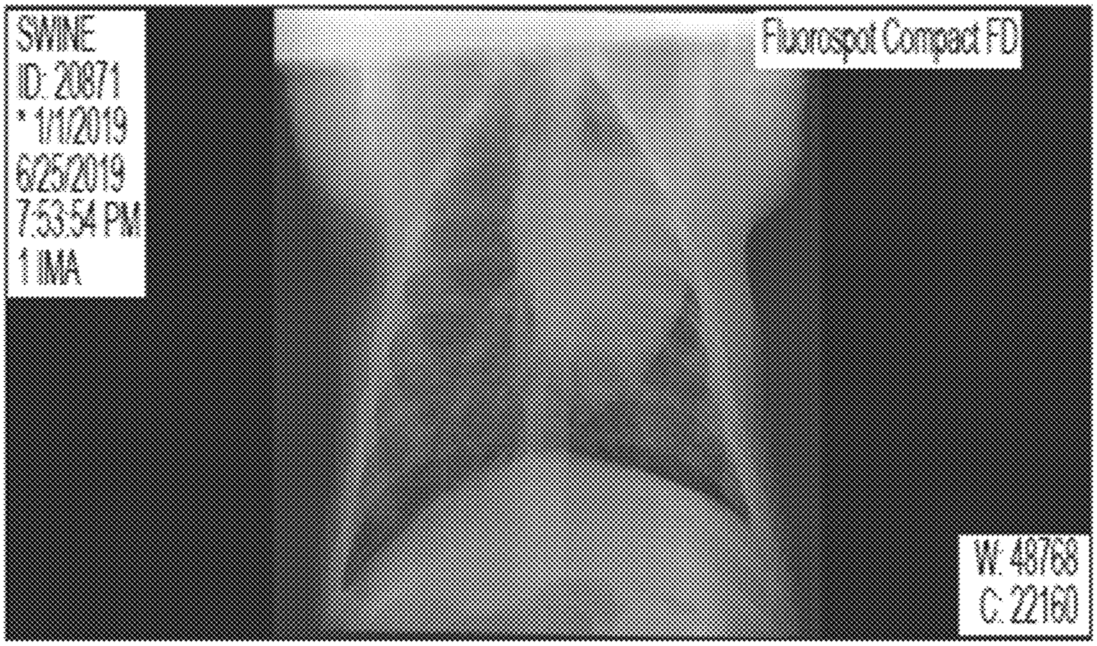
FIG. 5A shows, in accordance with certain embodiments, an X-ray image of a swine lung model.
Figure 5B:
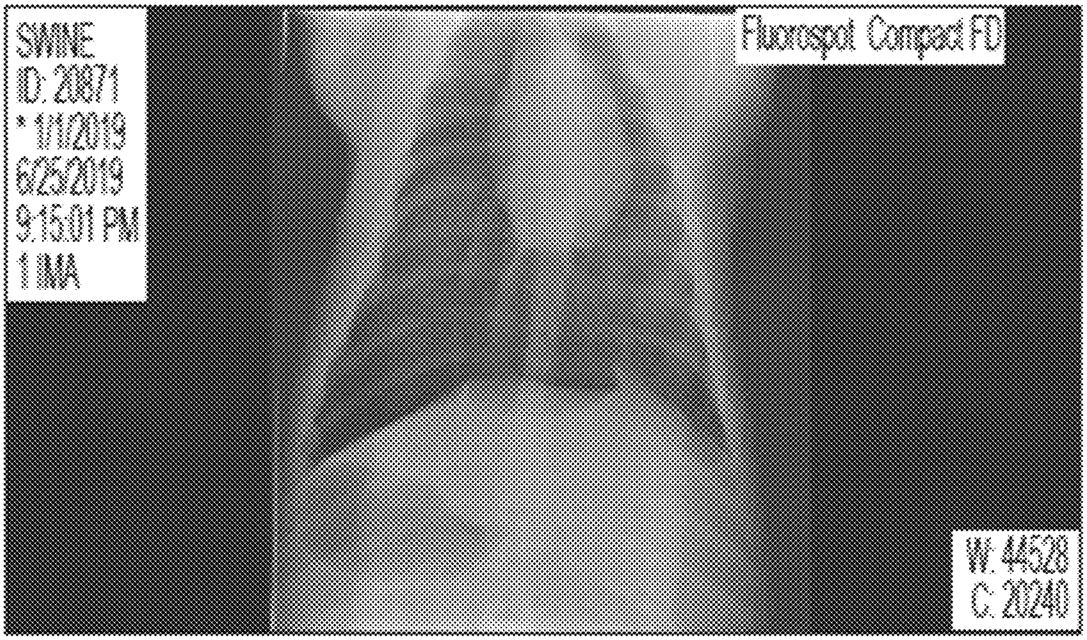
FIG. 5B shows, in accordance with certain embodiments, an X-ray image of a post biopsy swine lung model.
Figure 6A:
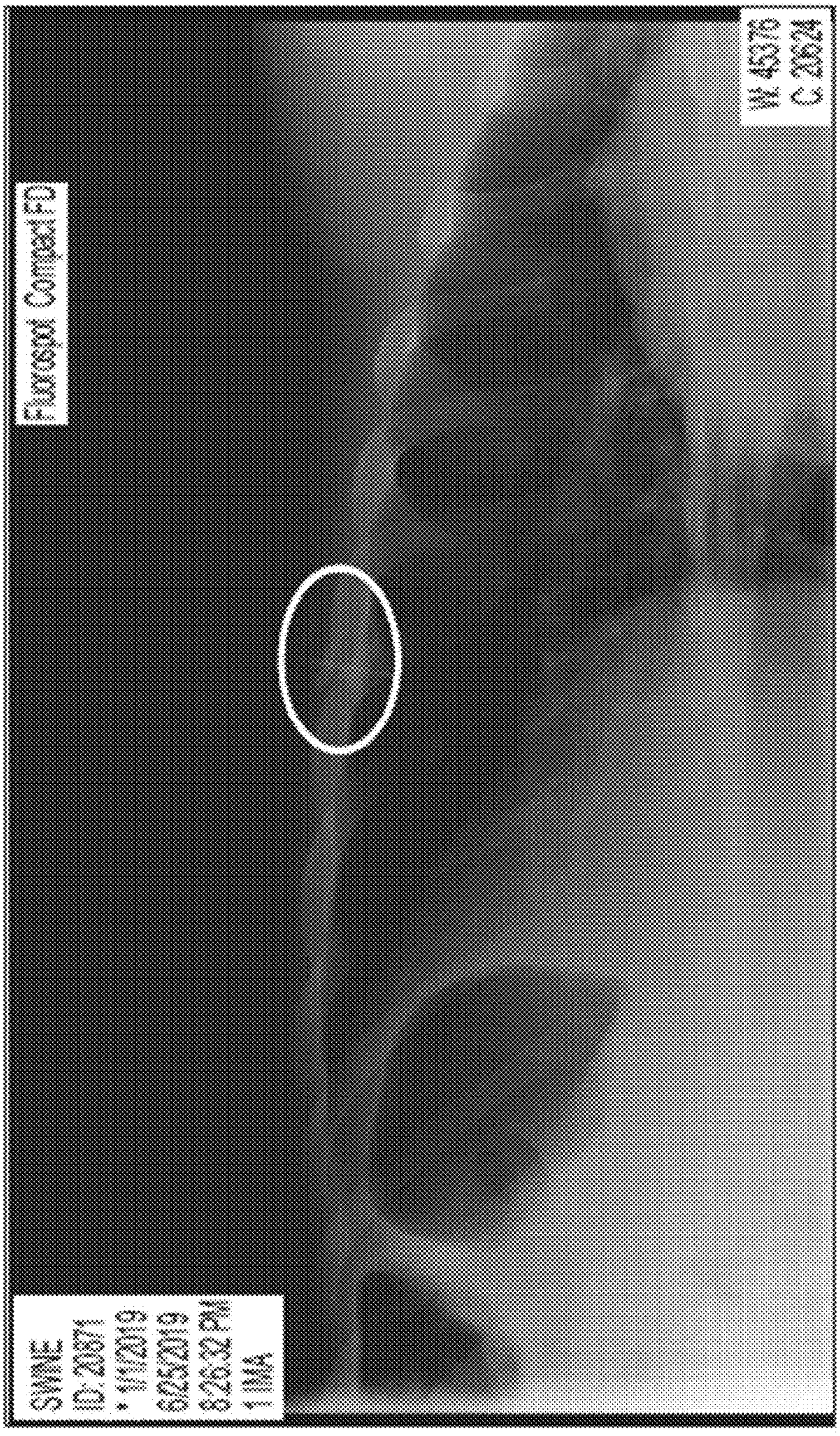
FIG. 6A shows, in accordance with certain embodiments, an X-ray image of the coaxial insertion of a syringe needle to deliver a hydrogel tissue sealant to a swine lung model.
Figure 6B:
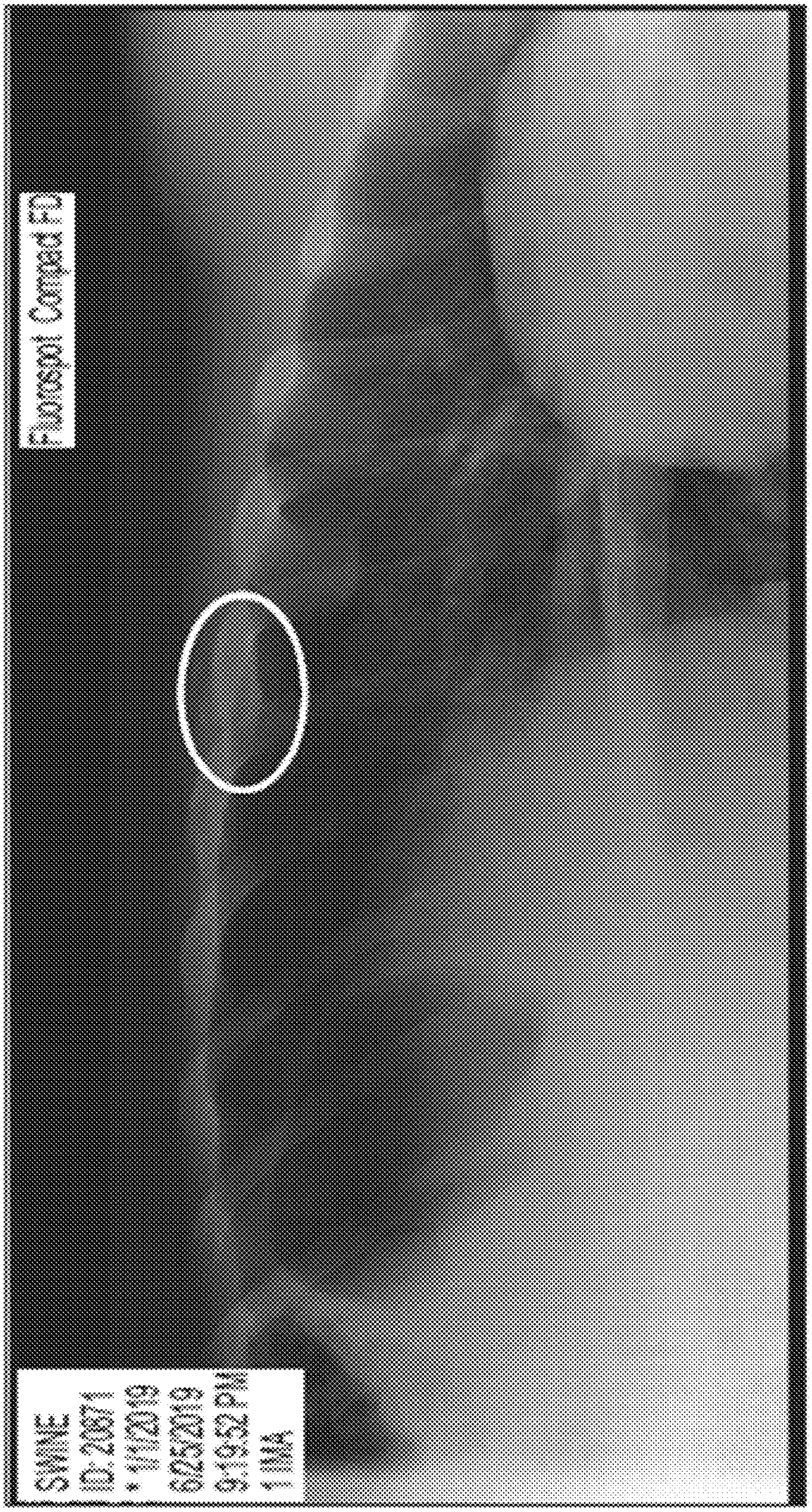
FIG. 6B shows, in accordance with certain embodiments, an X-ray image of swine lung model with a hydrogel tissue sealant.
Figure 7A:
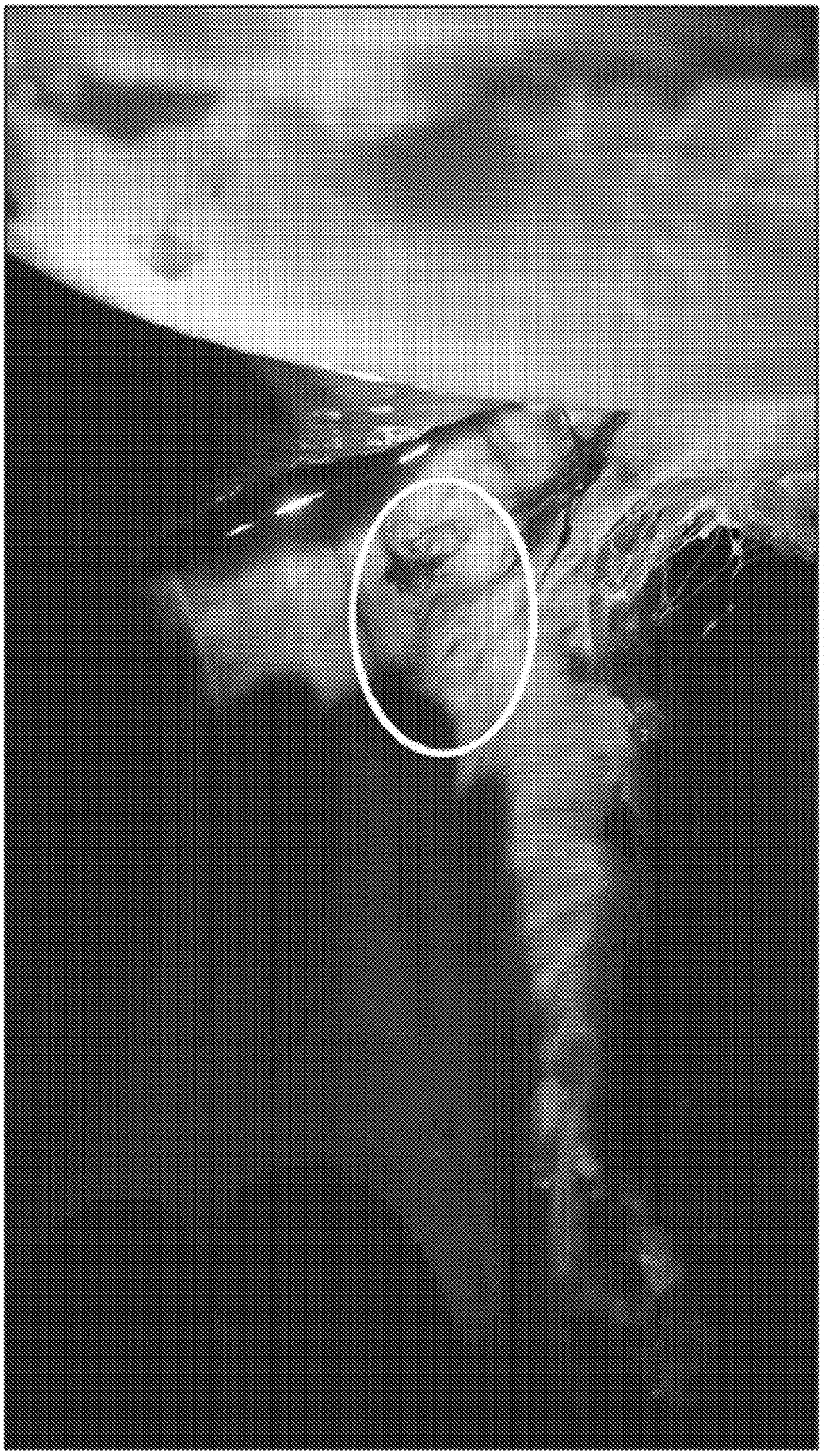
FIG. 7A shows, in accordance with certain embodiments, an image of a hydrogel tissue sealant adhered to the parietal pleura of a swine lung model.
Figure 7B:
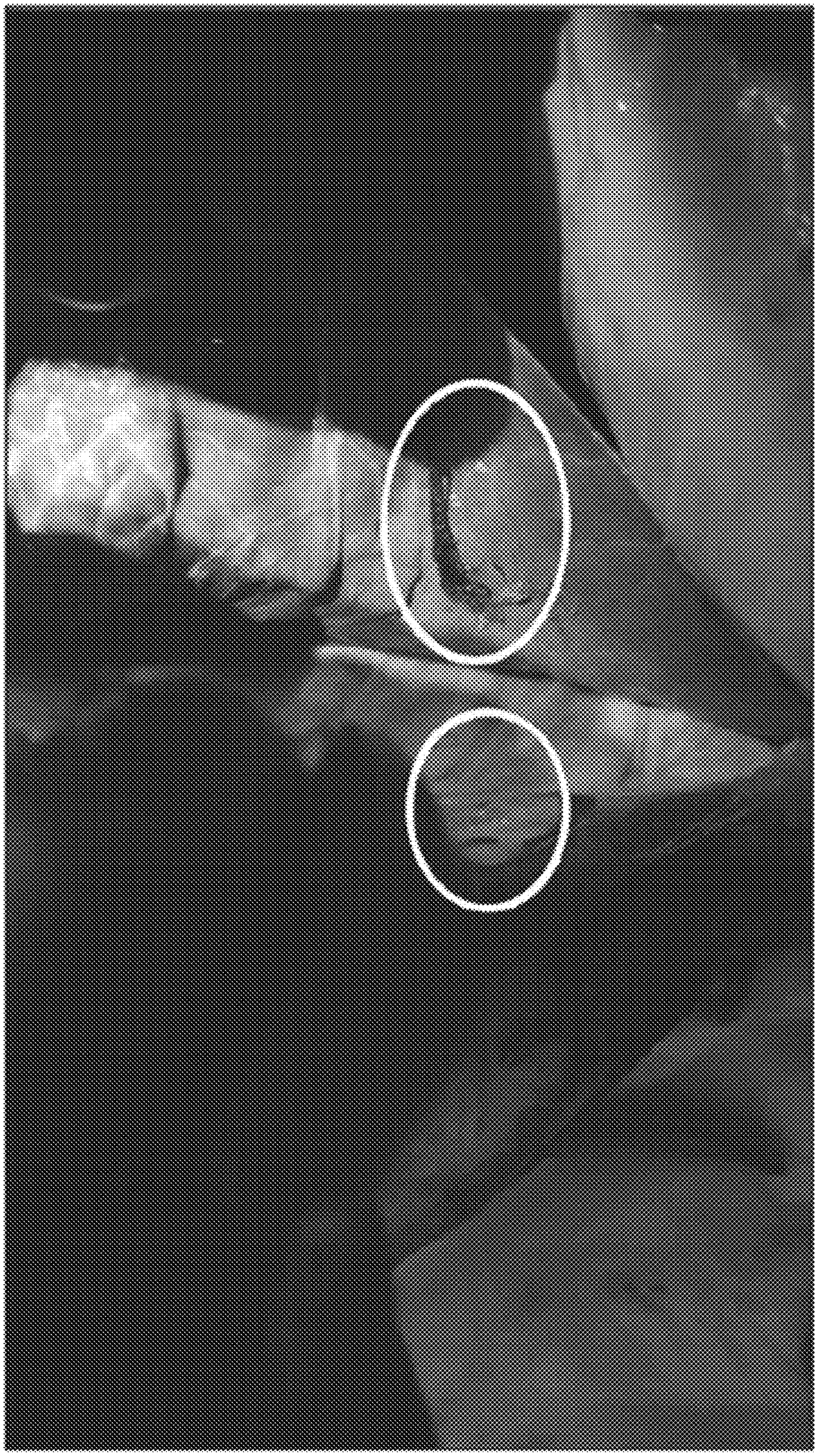
FIG. 7B shows, in accordance with certain embodiments, an image of a hydrogel tissue sealant adhered to the parietal and visceral pleura of swine lung model.

The following example describes the use of a hydrogel tissue sealant in a swine lung model. An X-ray image of a swine lung model was obtained, as shown in FIG. 5A. A biopsy was performed on the swine lung model. FIG. 5B shows the normal airway pressure of a post biopsy image of a swine lung model. The hydrogel forming composition was prepared, comprising the reaction product of $PEG(SS)_2$ and albumin with iohexol as the radiopaque material. As shown in FIG. 6A, the hydrogel forming composition was delivered upon initial puncture of the lung, via needle (circled), to the swine lung model prior to the biopsy. The hydrogel tissue sealant is visible through the soft tissue and pleural space. The coaxial component of the applicator was left in place, and the sealant application needle was removed. The biopsy needle was inserted through the coaxial component to the target tissue, the biopsy samples were acquired, and the coaxial component as well as the biopsy needle were removed. As shown in FIG. 6B, the hydrogel tissue sealant (circled) remains in place and is easily visualized post procedure, where it closes off the puncture site. The hydrogel tissue sealant permitted normal ventilation. FIG. 5B shows an X-ray image of a swine lung model post biopsy. As shown in FIG. 7A, the hydrogel tissue sealant (circled) is adhered to the parietal pleura of the swine lung model. Furthermore, as shown in FIG. 7B, the hydrogel tissue sealant (circled) is protruding from the inside lung and is adhered to the parietal and visceral pleura of the swine lung model, therefore sealing the biopsy tract.

Example 2

The following example describes the evaluation of the stability of a hydrogel forming composition in an accelerated aging study.

Samples of hydrogel forming compositions including a $PEG(SS)_2$-containing component and a recombinant human serum albumin (rHSA)-containing component were generated according to Table 1. $PEG(SS)_2$ was obtained from Sigma (Samples 1, 3, and 4) or Laysan Bio (Sample 2) and handled under a nitrogen environment. The $PEG(SS)_2$-containing component comprised either $PEG(SS)_2$ or PEG $(SS)_2$ with added BHT. In certain cases, a desiccant or molecular sieve material was also enclosed in the pouch—the desiccant packet containing either PharmaKeep® (Mitsubishi Gas Chemical America, Inc.) or 4A molecular sieves (Multisorb Filtration Group). The $PEG(SS)_2$-containing component was aliquoted into a first syringe and stored in a sealed foil pouch under an atmosphere of nitrogen gas. The rHSA-containing component solution used to prepare, via lyophilization, the rHSA-containing component used for forming the hydrogel included rHSA obtained from InVitria (Junction City, KS), with added sodium carbonate, and PEG 8000, combined with reverse osmosis (RO) water so that the concentration of the rHSA was 30% mass by volume. The rHSA-containing component solution in the RO water was lyophilized, ground into a powder, aliquoted into a second syringe, and sealed in a foil pouch under a nitrogen environment.

A hydration kit was created using deionized (DI) water in a third syringe (for hydrating the $PEG(SS)_2$-containing component) and DI water containing Pluronic® L61 in a fourth syringe (for hydrating the lyophilized rHSA-containing component). The hydration kit was sealed in a foil pouch with two Luer-Lock® connectors to be connected to each syringe so that the powders mixtures could be hydrated at the point of use. The samples received two doses of electron beam sterilization. All samples were stored and conditioned at 40° C. to simulate advanced aging compared to room-temperature storage.

TABLE 1

Components of tested hydrogel forming compositions.

| Sample Number | $PEG(SS)_2$-Containing Component | rHSA-Containing Component |
|---|---|---|
| 1 | $PEG(SS)_2$ | rHSA mixture |
| 2 | $PEG(SS)_2$, BHT, and Desiccant | rHSA mixture |
| 3 | $PEG(SS)_2$ and PharmaKeep ® | rHSA mixture |
| 4 | $PEG(SS)_2$ and Desiccant | rHSA mixture |

The samples were aged according to Table 2, pulled at the indicated time point, and evaluated, as explained in further detail below.

TABLE 2

Stability time points for the hydrogel forming composition and the corresponding simulated advanced age.

| Stability Time Points | Simulated Advanced Age |
|---|---|
| Time zero | 0 |
| 113 days | 1 year |
| 225 days | 2 years |
| 338 days | 3 years |

The gel times of the four hydrogel forming composition samples denoted in Table 1 were evaluated at each stability time point by: (i) hydrating the $PEG(SS)_2$-containing component and the rHSA-containing component, (ii) waiting for a period of two minutes, thirty minutes, or sixty minutes after hydration, (iii) dispensing the hydrated components into a vial containing a stir bar on a stir plate adjusted to 300 RPM, (iv) recording the initial time upon dispensing the components, and (v) recording the end time when gelation caused the stir bar to stop spinning. Results are shown in Table 3.

TABLE 3

Gel times for tested hydrogel forming compositions for samples aged for the indicated Stability Time Point (average of three replicate measurements).

| Time Point | Time After Hydration | Sample 1 Gel Time (see) | Sample 2 Gel Time (sec) | Sample 3 Gel Time (sec) | Sample 4 Gel Time (sec) |
|---|---|---|---|---|---|
| Time zero | 2 to 60 minutes | 1 to 4 | 1 to 2 | 1 to 2 | 1 to 2.3 |
| 113 days | 2 to 60 minutes | * | 1 to 1.3 | 1.3 to 2 | 1 to 1.7 |
| 225 days | 2 to 60 minutes | Not Tested | 2 to 2.67 | 5.3 to 13 | 2 |
| 338 days | 2 to 60 minutes | Not Tested | 1 to 1.7 | 9 to 14 | 1 to 1.7 |

* = two out of the three samples did not gel.

The dissolution times of the four rHSA-containing component samples denoted in Table 1 were evaluated at each stability time point by: (i) connecting the syringe containing the rHSA-containing component with the syringe containing DI water and Pluronic® L61, (ii) starting a timer, (iii) pushing the fluid back and forth into the powder syringe, and (iv) stopping the timer when the rHSA-containing component completely dissolved. Results are shown in Table 4.

TABLE 4

Dissolution times of rHSA-containing components for samples aged for the indicated Stability Time Point (average of three replicate measurements).

| Time Point | Sample 1 rHSA Dissolution Time (sec) | Sample 2 rHSA Dissolution Time (sec) | Sample 3 rHSA Dissolution Time (sec) | Sample 4 rHSA Dissolution Time (sec) |
|---|---|---|---|---|
| Time zero | 29 | 22 | 25 | 26 |
| 113 days | 14 | 39 | 21 | 25 |
| 225 days | Not Tested | 49.67 | 18 | 64.67 |
| 338 days | Not Tested | 59.3 | 135 | 72.7 |

The pHs of the four rHSA-containing component samples denoted in Table 1 were evaluated at each stability time point by: (i) dissolving the powder mixture with the syringe containing the DI water and Pluronic® L61 as described above for the dissolution time measurement, and (ii) measuring the pH of the solution using a calibrated Mettler Toledo FiveEasy pH Meter. Results are shown in Table 5.

TABLE 5 pHs of rHSA-containing components for samples aged for the indicated Stability Time Point (a verage of three replicate measurements).

| Time Point | Sample 1 rHSA pH | Sample 2 rHSA pH | Sample 3 rHSA pH | Group 4A rHSA pH |
|---|---|---|---|---|
| Time zero | 10.34 | 10.43 | 10.37 | 10.35 |
| 113 days | 10.33 | 10.64 | 10.44 | 10.52 |
| 225 days | Not Tested | 10.34 | 10.65 | 10.60 |
| 338 days | Not Tested | 10.38 | 10.22 | 10.35 |

The swelling rates of the hydrogel compositions formed from the four samples denoted in Table 1 were evaluated at each stability time point by: (i) forming the hydrogel composition by hydrating the $PEG(SS)_2$-containing component and the rHSA-containing component, dispensing the components through a mixing tip, and allowing them to gel; (ii) recording the weight of the hydrogel composition at time zero, (iii) incubating the hydrogel composition in a phosphate-buffered saline (PBS) solution at 37° C., (iv) removing the hydrogel composition from the PBS solution after two hours; and (v) recording the weight of the hydrogel composition. The percent swelling was calculated by percentage weight gain. Results are shown in Table 6.

TABLE 6

Swelling rates of tested hydrogel compositions at two hours for samples aged for the indicated Stability Time Point (average of three replicate measurements).

| Time Point | Sample 1 Swelling Rate | Sample 2 Swelling Rate | Sample 3 Swelling Rate | Sample 4 Swelling Rate |
|---|---|---|---|---|
| Time zero | 54.49% | 44.63% | 39.19% | 45.08% |
| 113 days | Did not gel | 45.77% | 65.68% | 66.75% |
| 225 days | Not tested | 30.31% | 78.77% | 45.90% |
| 338 days | Not tested | 30.01% | Not Tested | 40.02% |

Example 3

The following example describes the liquid burst pressure strength of hydrogel compositions according to certain embodiments.

Hydrogel compositions including $PEG(SS)_2$ and rHSA were generated according to Table 7. The rHSA-containing component included rHSA lyophilized with Pluronic® L61 and an antioxidant. Forty-five samples of three different hydrogel forming compositions were investigated. The percent mass by volume of rHSA varied from 10-30% between compositions, and the amount of $PEG(SS)_2$ also varied so that the NHS ester:amine ratio was kept constant for all three compositions at 2.21.

TABLE 7

Components of tested hydrogel forming compositions.

| Composition | $PEG(SS)_2$-Contaming Component | rHSA-Containing Component | % Mass by Volume of rHSA |
|---|---|---|---|
| 1 | $PEG(SS)_2$ | rHSA mixture | 10% |
| 2 | $PEG(SS)_2$ | rHSA mixture | 15% |
| 3 | $PEG(SS)_2$ | rHSA mixture | 30% |

The powdered $PEG(SS)_2$ and the rHSA-containing component were aliquoted into their own syringe and each was hydrated with a separate syringe containing 1 mL of water. The components were then dispensed through a mixing tip and allowed to gel. The adherence of the hydrogel composition was determined by a liquid burst pressure model based on ASTM F2392-04 (the Standard Test Method for Surgical Sealants). Results are shown in Table 8.

TABLE 8

Average liquid burst pressure strength of tested hydrogel compositions (average of forty-five replicate measurements).

| Composition | Average Liquid Burst Pressure Strength (mm Hg) |
|---|---|
| 1 | 25.92 |
| 2 | 111.83 |
| 3 | 208.97 |

Example 4

The following example describes the evaluation of inventive hydrogel compositions as a sealant for use during lung biopsy procedures in swine models to prevent pneumothorax complications.

Five hydrogel compositions were generated. $PEG(SS)_2$ was handled under a nitrogen environment. $PEG(SS)_2$ was aliquoted into a first syringe and stored in a sealed pouch under an atmosphere of nitrogen gas. The rHSA-containing component solution used to prepare, via lyophilization, the rHSA-containing component used for forming the hydrogel included rHSA with added sodium carbonate, PEG 8000, and Pluronic® L61, combined with RO water. The rHSA-containing component solution in the RO water was lyophilized, ground into a powder, aliquoted into a second syringe, and sealed in a foil pouch under a nitrogen environment.

A hydration kit (e.g., a double barrel syringe) was created using DI water in a first compartment of the double barrel syringe (for hydrating the $PEG(SS)_2$-containing component) and DI water in a second compartment of the double barrel syringe (for hydrating the lyophilized rHSA-containing component). The hydration kit was sealed in a foil pouch with connections to each syringe containing $PEG(SS)_2$ and the rHSA-containing component so that the powder mixtures could be hydrated with their respective solution at the point of use.

A total of ten swine subjects were evaluated. Five of the ten swine were designated as test subjects and were implanted with a hydrogel composition in the left lower lung lobe. To deliver the hydrogel composition, a coaxial technique was utilized with computed tomography (CT) guidance. The delivery device was inserted through the soft tissue until adjacent to the lung and pleural space (see FIG. 8A). The hydrogel composition was hydrated and deployed through the ported needle system of the delivery device into the subcutaneous tissue, pleural space, and the immediately adjacent area of the lung parenchyma (see FIG. 8B). CT imaging was used to confirm placement of the hydrogel.

Following successful implantation of the hydrogel composition, a lung biopsy was taken through use of a coaxial cannula within five minutes of implantation of the hydrogel composition. Briefly, the needle was adjusted as needed and advanced to the site of the biopsy and the ported needle delivery system was removed. A standard biopsy needle was inserted through the coaxial system, and a standard lung biopsy procedure was performed continuing to use CT guidance, utilizing 160 Bard Mission Biopsy Needles (see FIG. 8C).

A follow-up evaluation for two of the five test subjects was performed at 72 (±8) hours post-implantation of the hydrogel, and evaluation of the other three swine was performed at 144 (±8) hours post-implantation. During the follow-up evaluation, a CT scan was completed to assess for the presence of the hydrogel composition and the presence (or absence) of pneumothorax. After completing the CT scan, the animals were euthanized and a comprehensive necropsy was performed with target organs (i.e., the lung) removed for gross pathologic observation. The inner chest wall (e.g., the parietal pleura) was also examined.

The five control swine received lung biopsy procedures as described above but without implantation of the hydrogel composition. Follow-up evaluations (including a CT scan to assess for the presence (or absence) of pneumothorax) were performed at 48 (±8) hours post-lung biopsy. The animals were then euthanized after their CT scan (unless otherwise noted) and a comprehensive necropsy was performed with target organs removed for gross pathologic observation.

A summary of the study design is shown in Table 9.

TABLE 9

Summary of swine model study design.

| Cohort | Subject # | Sealant Lung Location | Follow Up Period |
|---|---|---|---|
| Test subject | 1 | Left lower lobe | 6 days |
| Test subject | 2 | Left lower lobe | 3 days |
| Test subject | 3 | Left lower lobe | 6 days |
| Test subject | 4 | Left lower lobe | 6 days |
| Test subject | 5 | Left lower lobe | 3 days |
| Control subject | 6 | Left lower lobe | 2 days |
| Control subject | 7 | Left lower lobe | 2 days |
| Control subject | 8 | Left lower lobe | 2 days |
| Control subject | 9 | Left lower lobe | 2 days |
| Control subject | 10 | Left lower lobe | 2 days |

Figure 9A:
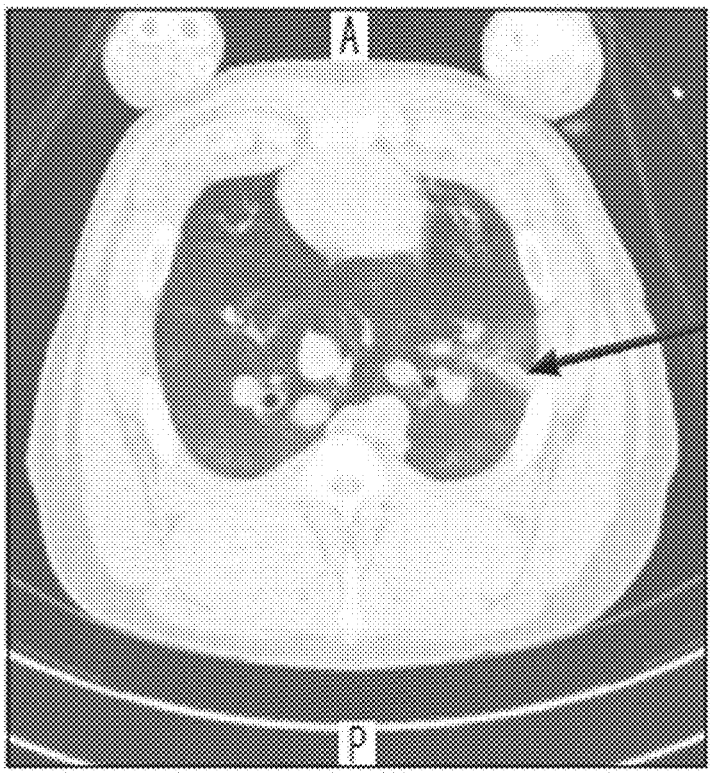
FIG. 9A shows, in accordance with certain embodiments, a CT scan of a test subject (Test Subject 5) three days after deployment of the hydrogel and subsequent lung biopsy procedure.

Each of the five test subjects were successfully implanted with the hydrogel composition prior to the lung biopsy procedure. Deployment of the hydrogel composition was successful and did not cause any immediate issues or concerns to the physician performing the procedure. No pneumothorax complications developed during the biopsy procedures or during the 20-30-minute monitoring period after the procedure. All five test subjects survived until their slated follow-up date at either day 3 or day 6. Furthermore, all five test subjects showed no signs of post-operative or delayed pneumothorax on their post CT scans (see FIG. 9A for Subject 5, as representative wherein the arrow indicates the site of the hydrogel). Necropsy revealed retained hydrogel material, as expected at day 3 or 6. The hydrogel compositions in the day 6 test subjects (i.e., samples 1, 3, and 4) demonstrated a decrease in hydrogel firmness, indicating resorption. All five test subjects showed minor irritation on the parietal pleura surrounding the needle insertion site, but nothing warranting major concern.

Figure 9B:
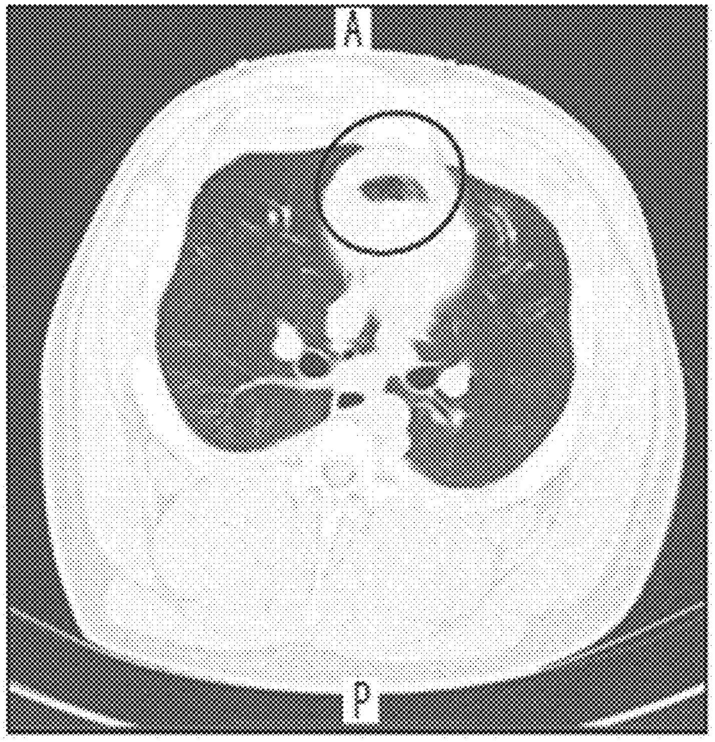
FIG. 9B shows, in accordance with certain embodiments, a CT scan of a control subject (Control Subject 9) immediately after a lung biopsy procedure, showing an air embolism.
Figure 9C:
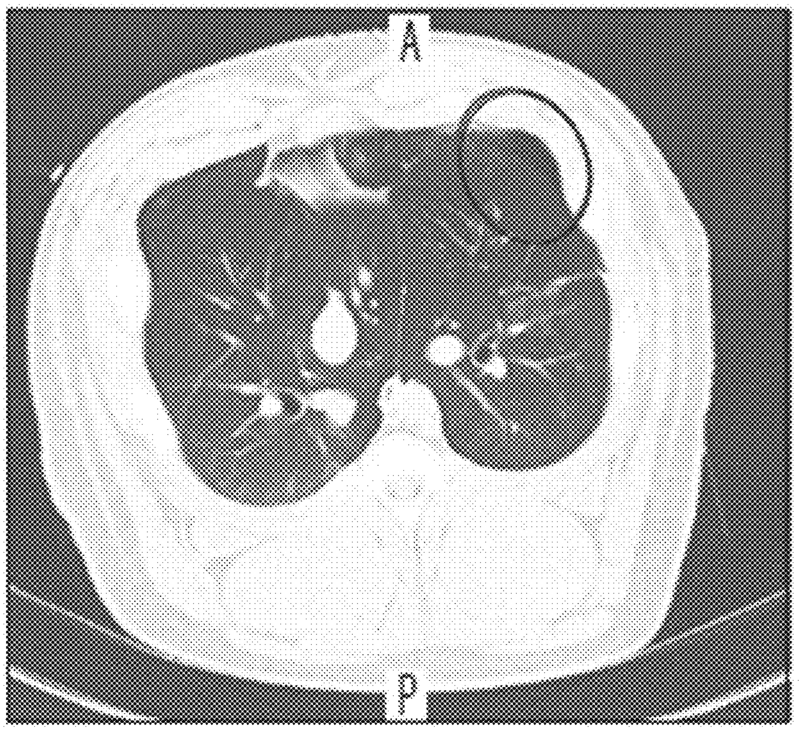
FIG. 9C shows, in accordance with certain embodiments, a CT scan of a control subject (Control Subject 10) immediately after a lung biopsy procedure, showing pneumothorax.
Figure 9D:
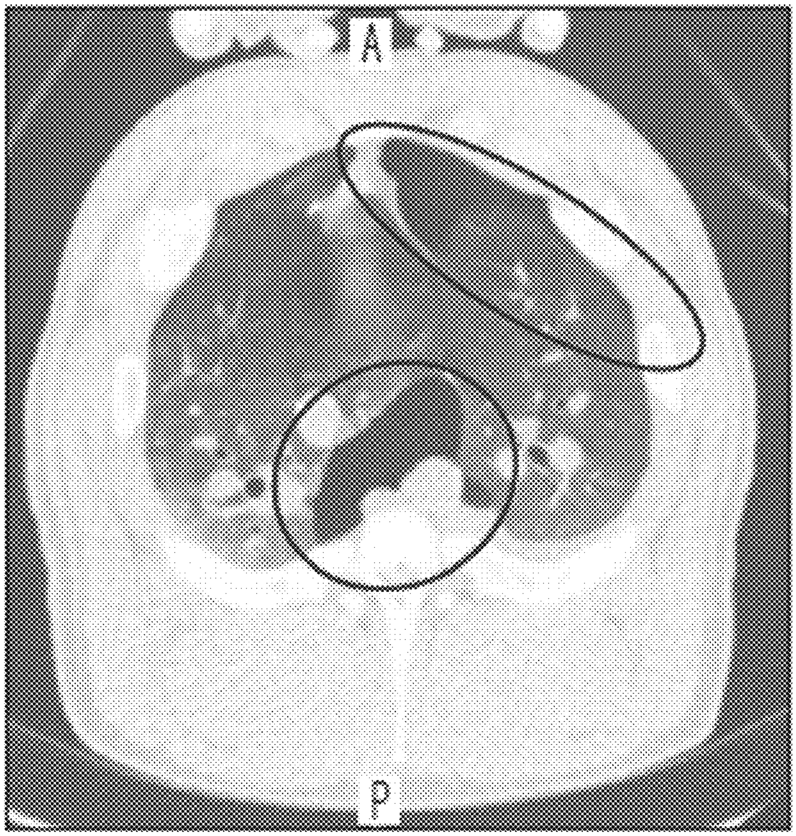
FIG. 9D shows, in accordance with certain embodiments, a CT scan of a control subject (Control Subject 6) two days after a lung biopsy procedure, showing pneumothorax.

The five control subjects received a lung biopsy without application of the hydrogel composition. Two of the five control subjects (i.e., Subjects 9 and 10) developed intraprocedural pneumothorax and a subsequent air embolism, as revealed by CT. FIG. 9B shows an example of an air embolism (circled) for Subject 9, and FIG. 9C shows an example of pneumothorax (circled) for Subject 10. Due to the severe nature of these complications, the two test subjects were terminated after completing the biopsy. The three remaining control subjects tolerated the lung biopsy, and CT scans at the time of follow up showed one swine with a large pneumothorax present (i.e., Subject 6, see FIG. 9D, wherein the circles indicate pneumothorax). The other two swine (i.e., Subjects 7 and 8) were clear and free of complications. Necropsy revealed nothing of note for any of the control subjects.

A summary of the test results are shown in Table 10. The results showed an improvement in the outcome of the lung biopsy procedure for the test subjects (pneumothorax rate of 0%) as compared to the control subjects (pneumothorax rate of 60%).

TABLE 10

Summary of test results for the evaluation of pneumothorax in test and control subjects.

| Subject # | Post Biopsy Pneumothorax | Follow Up Pneumothorax | Necropsy Notes |
|---|---|---|---|
| 1 | Negative | Negative | Minor irritation of parietal pleura |
| 2 | Negative | Negative | Minor irritation of parietal pleura |
| 3 | Negative | Negative | Very minor irritation of parietal pleura |
| 4 | Negative | Negative | Minor irritation of parietal pleura |
| 5 | Negative | Negative | Irritation of parietal pleura |
| 6 | Negative | Positive | Nothing of note |
| 7 | Negative | Negative | Nothing of note |
| 8 | Negative | Negative | Nothing of note |
| 9 | Positive | N/A | Nothing of note |
| 10 | Positive | N/A | Nothing of note |

Example 5

The following example describes the preparation and evaluation of various non-limiting hydrogel forming compositions.

Samples of recombinant human serum albumin (rHSA)-containing components for hydrogel forming compositions were generated according to Table 1. The solutions used to prepare, via lyophilization, the rHSA-containing components used for forming the hydrogel included rHSA obtained from InVitria (Junction City, KS), sodium hydroxide (added as dilute solutions having the amounts of NaOH listed in Table 11 below dissolved in 20 mL of deionized water), and PEG 8000 (referred to as "PEG" in Table 11), combined with deionized water according to the formulations shown in Table 11. The pH values of the resulting solutions were recorded using the same pH meter described in Example 2 and are also shown in Table 11.

TABLE 11

| Formulations for rHSA-containing components. | | | | |
|---|---|---|---|---|
| | Formulation A | Formulation B | Formulation C | Formulation D |
| rHSA (g) | 5 | 5 | 5 | 5 |
| Water (g) | 50 | 50 | 50 | 50 |
| PEG (g) | 0.7 | 0.7 | 0.7 | 0.7 |
| NaOH (g) | 0.025 | 0.05 | 0.1 | 0.2 |
| Total Mass of solids added (g) | 5.725 | 5.75 | 5.8 | 5.9 |
| % rHSA | 87.34% | 86.96% | 86.21% | 84.75% |
| % PEG | 12.23% | 12.17% | 12.07% | 11.86% |
| % NaOH | 0.437% | 0.870% | 1.724% | 3.390% |
| pH Result | 8.30 | 9.37 | 10.48 | 11.40 |

Samples of hydrogel forming compositions including a $PEG(SS)_2$-containing component and the rHSA-containing component formulations from Table 11 were generated. $PEG(SS)_2$ was obtained from Laysan Bio, Inc. (Arab, Alabama) and handled under a nitrogen or argon environment, and was prepared and used immediately after weighing. The rHSA-containing component solutions in the deionized water from Table 11 were lyophilized, ground into a powder, and used for subsequent experiments.

The gel time for the hydrogel forming compositions based on the formulations in Table 11 were measured according to the method described in Example 2, and the results are shown in Table 12. The rHSA-containing components were dissolved in a 0.9% NaCl saline hydration solution containing Pluronic® L61 to form solutions of 25 w/v % rHSA, and the resulting solutions were mixed with a solution of hydrated $PEG(SS)_2$ in an amount such that there was a 2.64:1 NHS ester:amine ratio.

TABLE 12

| Gel time of a 25% rHSA solution crosslinked with $PEG(SS)_2$ at a 2.64:1 NHS ester:amine ratio. Measurements are averages from triplicate experiments. | | | | |
|---|---|---|---|---|
| Time after Hydration | Formulation A 25% Concentration - Gel Time (s) | Formulation B 25% Concentration - Gel Time (s) | Formulation C 25% Concentration - Gel Time (s) | Formulation D 25% Concentration - Gel time (s) |
| 2 minutes | No gel formed | >30 seconds | 1.7 | 0.85 |
| 30 minutes | Not tested | No gel formed | 2.3 | 1.18 |
| 60 minutes | Not tested | Not tested | 2.34 | 1.45 |

The results in Table 12 indicated poor gelation performance using formulation A, and successful gel formation by formulations B, C, and D. It was observed that formulation C had adequate gelation timing for tissue sealant applications while also having sufficient pot life.

An additional formulation of rHSA-containing component, formulation E, was prepared by forming a solution according to the methods described for formulations A-D, but scaled up to 400 g and resulting in respective relative weight percentages of 1.612% NaOH, 11.999% PEG, and 86.389% rHSA. Swelling measurements of hydrogel forming compositions using formulation E with varying hydration solutions (deionized water, phosphate-buffered saline (PBS), and saline solution, respectively, each containing Pluronic® L61) for the rHSA-containing component were measured according to the method described in Example 2 and compared with a Progel™ comparative example. The hydrated rHSA-containing component solutions were mixed with a solution of hydrated $PEG(SS)_2$ in an amount such that there was a 2.64:1 NHS ester:amine ratio. The results are reported in Table 13.

TABLE 13

| Swelling results of Formulation E crosslinked with $PEG(SS)_2$ at a 2.64:1 molar ratio. Measurements are averages from triplicate experiments. | | | |
|---|---|---|---|
| | Swelling Rate at 2 Hours | Swelling Rate at 24 Hours | Swelling Rate at 48 Hours |
| Formulation E with Water | 37.77% | 46.81% | 66.81% |
| Progel | 85.94% | 226.55% | 187.06% |
| Formulation E with PBS | 38.32% | 46.78% | 54.37% |
| Formulation E with Saline | 39.25% | 45.56% | 56.60% |

The results in Table 13 demonstrate that adequate swelling characteristics can be achieved with the hydrogel forming compositions of this disclosure.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements);

etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A hydrogel forming composition for forming a hydrogel tissue sealant, comprising:

a first component comprising a crosslinking agent, wherein the crosslinking agent is a difunctionalized polyalkylene oxide-based component of the formula:

G-LM-PEG-LM-G;

Wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_a—O—C(O)—$ where d is an integer from 1 to 10, an amide containing diradical of the formula $—N(H)—C(O)—(CH_2)—C(O)—$ where d is an integer from 1 to 10, an amide containing diradical of the formula $—(CH_2)—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_a—O—C(O)—$, $—R—N(H)—C(O)—(CH_2)_a—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a second component comprising a protein that is capable of crosslinking with the crosslinking agent;

a crosslinking initiator in an amount selected to provide a desired gel time;

a surfactant; and one or more solvents in which the first component, the second component, the crosslinking initiator, and the surfactant are soluble or miscible, wherein upon dissolution of the first component, the second component, the crosslinking initiator, and the surfactant in the one or more solvents, crosslinking of the crosslinking agent and the protein occurs characterized by a gel time less than or equal to 5 seconds to form the hydrogel tissue sealant able to prevent or reduce a risk of pneumothorax during or after a lung biopsy procedure.

2. A hydrogel forming composition for forming a hydrogel tissue sealant, comprising:

a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_a—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_a—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a protein that is capable of crosslinking with the crosslinking agent;

a crosslinking initiator in an amount selected to provide a desired gel time;

a surfactant; and one or more solvents in which the crosslinking agent, the protein, the crosslinking initiator, and the surfactant are soluble or miscible;

wherein upon dissolution of the crosslinking agent, the protein, the crosslinking initiator, and the surfactant in the one or more solvents, crosslinking of the crosslinking agent and the protein occurs characterized by a gel time less than or equal to 5 seconds to form the hydrogel tissue sealant able to prevent or reduce a risk of pneumothorax during or after a lung biopsy procedure.

3. A hydrogel forming composition for forming a hydrogel tissue sealant, comprising:

a first component comprising a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a second component comprising a protein that is capable of crosslinking with the crosslinking agent and a crosslinking initiator in an amount selected to provide a desired gel time;

a surfactant; and one or more solvents in which the first component, the second component, and the surfactant are soluble or miscible;

wherein upon dissolution of the first component, the second component, and the surfactant in the one or more solvents, crosslinking of the crosslinking agent and the protein occurs characterized by a gel time less than or equal to 5 seconds to form the hydrogel tissue sealant able to prevent or reduce a risk of pneumothorax during or after a lung biopsy procedure.

4. A hydrogel forming composition for forming a hydrogel tissue sealant, comprising:

a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_d—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_d—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a protein that is capable of crosslinking with the crosslinking agent;

a surfactant;

a first solvent able to dissolve the crosslinking agent; and a second solvent able to dissolve the protein;

wherein when the protein is dissolved in the second solvent a pH of a solution of the protein in the second solvent is greater than or equal to 10.2 and less than or equal to 10.6; and wherein when the crosslinking agent is dissolved in the first solvent and combined with the solution of the protein in the second solvent and the surfactant crosslinking of the crosslinking agent and the protein occurs to form the hydrogel tissue sealant able to prevent or reduce a risk of pneumothorax during or after a lung biopsy procedure.

5. A hydrogel forming composition for forming a hydrogel tissue sealant, comprising:

a crosslinking agent, wherein the crosslinking agent is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_a—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_a—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a protein that is capable of crosslinking with the crosslinking agent;

a surfactant; and one or more solvents able to dissolve the crosslinking agent and the protein such that when the crosslinking agent and the protein are separately mixed with the one or more solvents, at least the protein is able to have a dissolution time at 25° C. of less than or equal to 30 seconds, wherein when the crosslinking agent, the protein, and the surfactant are all dissolved in the one or more solvents, upon mixing of the one or more solvents, crosslinking of the crosslinking agent and the protein occurs to form the hydrogel tissue sealant able to prevent or reduce a risk of pneumothorax during or after a ling biopsy procedure.

6. The composition of claim 1, wherein the crosslinking agent is a difunctionalized polyalkylene oxide-based component of the formula:

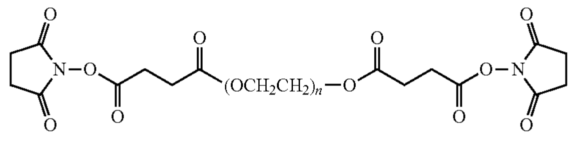

Polyethylene glycol disuccinimidyl succinate.

7. The composition of claim 1, wherein the protein is selected from the group of consisting of human serum albumin, recombinant human serum albumin, and animal sourced albumin.

8. The composition of claim 1, a wherein the crosslinking initiator comprises a base and/or a basic buffer comprising sodium carbonate.

9. A hydrogel forming composition for forming a hydrogel tissue sealant, comprising:

a first component comprising a crosslinking agent which is a difunctionalized polyalkylene oxide-based component of the formula:

G-LM-PEG-LM-G;

wherein:

PEG is polyethylene glycol;

each LM is a difunctional linking moiety independently selected from the group consisting of a carbonate diradical of the formula —C(O)—, a monoester diradical of the formula $—(CH_2)_b—C(O)—$ where b is an integer from 1 to 10, a diester radical of the formula $—C(O)—(CH_2)_c—C(O)—$ where c is an integer from 1 to 10 and where the aliphatic portion of the radical may be saturated or unsaturated, a dicarbonate diradical of the formula $—C(O)—O—(CH_2)_d—O—C(O)—$ where d is an integer from 1 to 10, an amide containing diradical of the formula $—N(H)—C(O)—(CH_2)_a—C(O)—$ where d is an integer from 1 to 10, an amide containing diradical of the formula $—(CH_2)_c—C(O)—N(H)—(CH_2)_d—$ where c is an integer from 1 to 10 and d is an integer from 1 to 10, and an oligomeric diradical represented by the formulas —R—C(O)—, $—R—C(O)—(CH_2)_c—C(O)—$, $—R—C(O)—O—(CH_2)_d—O—C(O)—$, $—R—N(H)—C(O)—(CH_2)_a—C(O)—$, or $—R—(CH_2)_c—C(O)—N(H)—(CH_2)_d—$ where c is an integer from 1 to 10, d is an integer from 1 to 10, and R is a polymer or copolymer having 1 to 10 monomeric lactide, glycolide, trimethylene carbonate, caprolactone or p-dioxanone fragments; and each G is a leaving group independently selected from the group consisting of N-oxysuccinimidyl, N-oxymaleimidyl, N-oxyphthalimidyl, nitrophenoxyl, N-oxyimidazolyl, and tresyl;

a protein that is capable of crosslinking with the crosslinking agent;

a crosslinking initiator;

a surfactant; and one or more solvents;

wherein the crosslinking initiator is present in an amount selected such that upon dissolution of the crosslinking agent, the protein, the crosslinking initiator, and the surfactant in the one or more solvents, crosslinking of the crosslinking agent and the protein occurs characterized by a gel time less than or equal to 5 seconds to form the hydrogel tissue sealant able to prevent or reduce a risk of pneumothorax during or after a lung biopsy procedure.

* * * * *